United States Patent
Li et al.

(10) Patent No.: US 11,491,123 B2
(45) Date of Patent: Nov. 8, 2022

(54) PHARMACEUTICAL COMPOSITIONS WITH ANTIFLAVIVIRAL ACTIVITY

(71) Applicants: HEALTH RESEARCH, INC., Menands, NY (US); THE UNITED STATES OF AMERICA, AS REPRESENTED BY THE SECRETARY, DEPARTMENT OF HEALTH AND HUMAN SERVICES, Bethesda, MD (US)

(72) Inventors: Hongmin Li, Glenmont, NY (US); Laura D. Kramer, Albany, NY (US); Zhong Li, Glenmont, NY (US); Ruili Huang, Rockville, MD (US); Menghang Xia, Potomac, MD (US)

(73) Assignees: HEALTH RESEARCH, INC., Menands, NY (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/312,316

(22) PCT Filed: Jun. 23, 2017

(86) PCT No.: PCT/US2017/039071
§ 371 (c)(1),
(2) Date: Dec. 21, 2018

(87) PCT Pub. No.: WO2017/223491
PCT Pub. Date: Dec. 28, 2017

(65) Prior Publication Data
US 2019/0160028 A1    May 30, 2019

Related U.S. Application Data

(60) Provisional application No. 62/461,492, filed on Feb. 21, 2017, provisional application No. 62/362,884, filed on Jul. 15, 2016, provisional application No. 62/353,887, filed on Jun. 23, 2016.

(51) Int. Cl.
| | |
|---|---|
| *A61K 31/167* | (2006.01) |
| *A61K 31/426* | (2006.01) |
| *A61K 31/609* | (2006.01) |
| *A61K 31/352* | (2006.01) |
| *A61K 31/409* | (2006.01) |
| *A61K 31/5415* | (2006.01) |
| *A61P 31/14* | (2006.01) |
| *C07C 235/64* | (2006.01) |

(52) U.S. Cl.
CPC .......... *A61K 31/167* (2013.01); *A61K 31/352* (2013.01); *A61K 31/409* (2013.01); *A61K 31/426* (2013.01); *A61K 31/5415* (2013.01); *A61K 31/609* (2013.01); *A61P 31/14* (2018.01); *C07C 235/64* (2013.01); *C12N 2770/24111* (2013.01); *Y02A 50/30* (2018.01)

(58) Field of Classification Search
CPC .. A61K 31/167; A61K 31/352; A61K 31/409; A61P 31/14
See application file for complete search history.

(56) References Cited

U.S. PATENT DOCUMENTS

| | | | |
|---|---|---|---|
| 2009/0304803 A1* | 12/2009 | Hasan | B82Y 5/00 424/497 |
| 2010/0009970 A1 | 1/2010 | Johansen et al. | |
| 2011/0000480 A1 | 1/2011 | Turner et al. | |
| 2011/0038890 A1 | 2/2011 | Raviv et al. | |
| 2011/0045024 A1 | 2/2011 | Dittmer et al. | |
| 2012/0125847 A1 | 5/2012 | Sehgal | |
| 2019/0016743 A1* | 1/2019 | Yen | A61P 35/00 |

FOREIGN PATENT DOCUMENTS

WO    2016077420 A1    5/2016

OTHER PUBLICATIONS

Jurgeit et al. Niclosamide is a proton carrier and targets acidic endosomes with broad antiviral effects. PLOS Pathogens. Oct. 2012, vol. 8, No. 10.*
Erythrosine. Alternative namings. Eletronic Resource: [https://pubchem.ncbi.nlm.nih.gov/compound/Erythrosine]. Retrieved on Sep. 30, 2019.*
Cheung et al. Antiviral activity of lanatoside C against dengue virus infection. (Antiviral Research, 111, 2014, 93-99).*
Cheung et al. (Antiviral Research, 111, 2014, 93-99).*
Chiu et al., International Journal of Molecular Medicine, 25, 231-236, 2010.*
Kabilan et al., Indian Journal of Pediatrics, vol. 71, Jul. 2004.*
Sambri et al.; Clinical Microbiology and Infection, vol. 19, No. 8, Aug. 2013.*
Li et al. Viral Proteases and their inhibitors. Chapter 7: Flavivirus NS2B/NS3 Protease: Structure, Function and Inhibition. 2017, pp. 163-188.*

(Continued)

*Primary Examiner* — Theodore R. Howell
(74) *Attorney, Agent, or Firm* — Heslin Rothenberg Farley & Mesiti P.C.

(57) ABSTRACT

Provided is a method of inhibiting viral replication, including contacting one or more cells that has been infected or contacted with a flavivirus with an effective amount of niclosamide, temoporfin, nitazoxanide, tizoxanide, erythrosin B, methylene blue. Contacting one or more cells that have been infected with a flavivirus may include administering the compound to a mammal, a human, or other subject. The flavivirus may be Dengue virus serotype 1, Dengue virus serotype 2, Dengue virus serotype 3, Dengue virus serotype 4, yellow fever virus, West Nile virus, Zika virus, Japanese encephalitis virus, tick-born encephalitis virus, Powassan virus, St. Louis encephalitis virus, or other flavivirus.

20 Claims, 36 Drawing Sheets

Specification includes a Sequence Listing.

(56) References Cited

OTHER PUBLICATIONS

Fang et al., "Identification of three antiviral inhibitors against Japanese encephalitis virus from library of pharmacologically active compounds 1280," PLoS One Nov. 4, 2013;8(11):e78425. PMID: 24348901. (Year: 2013).*

International Search Report and Written Opinion of the International Searching Authority for PCT/US2017/039071 dated Sep. 25, 2017.

Aubry, M., et al., "Inactivation of Zika virus in plasma with amotosalen and ultraviolet A illumination", Transfusion, vol. 56, pp. 33-40 (2016).

Barrows, N.J., et al., "A Screen of FDA-Approved Drugs for Inhibitors of Zika Virus Infection", Cell Host and Microbe, vol. 20, pp. 259-270 (2016).

Craig, R.A, et al., "Photosensitisers—the progression from photodynamic therapy to anti-infective surfaces", Expert Opinion on Drug Delivery, vol. 12, No. 1, pp. 85-101 (2015).

Garavito, G., et al., "The in vivo antimalarial activity of methylene blue combined with pyrimethamine, chloroquine and quinine", Mem Inst Oswaldo Cruz, Rio de Janiero, vol. 107, No. 6, pp. 820-823 (2012).

Imming, P., et al., "Drugs, their targets and the nature and number of drug targets", Nature Review|Drug Discovery, vol. 5, pp. 821-834 (2006).

Josefsen, L.B., et al., Unique Diagnostic and Therapeutic Roles of Porphyrins and Phthalocyanines in Photodynamic Therapy, Imaging and Theranostics, vol. 2, No. 9, pp. 916-966 (2012).

Jurgeit, A., et al., "Niclosamide Is a Proton Carrier and Targets Acidic Endosomes with Broad Antiviral Effects", PLOS Pathogens, vol. 8, Issue 10, e1002976, pp. 1-14 (2012).

Khater, H.F., et al., "Phototoxicity or Rose Bengal against the Camel Tick, *Hyalomma dromedarii*", International Journal of Veterinary Science, vol. 3, No. 2, pp. 78-86 (2014).

Lim, S.P., et al., "Ten years of dengue drug discovery: Progress and prospects", Antiviral Research, vol. 100, pp. 500-519 (2013).

Luo, D., et al., "The flavivirus NS2B-NS3 protease-helicase as a target for antiviral drug development", Antiviral Research, pp. 1-12 (2015).

Malone, R.W., et al., "Zika Virus: Medical Countermeasure Development Challenges", PLOS Neglected Tropical Diseases, pp. 1-26 (2016).

Marschner, S., et al., "Pathogen Reduction Technology Treatment of Platelets, Plasma and Whole Blood Using Riboflavin and UV Light", vol. 38, pp. 8-18 (2011).

Papin, J.F., et al., "Methylene blue photoinactivation abolishes West Nile virus infectivity in vivo", vol. 68, pp. 84-87 (2005).

Rajesh, S., et al., "Antimicrobial photodynamic therapy: An overview", J Indian Soc Periodontol. vol. 15, No. 4, pp. 323-327 (2011).

Rossignol, J., "Nitazoxanide: A first-in-class broad-spectrum antiviral agent", Antiviral Research, vol. 110, pp. 94-103 (2014).

Senge, M.O., et al., "Temoporfin (Foscan, 5, 10, 15, 20-Tetra(m-hydroxyphenyl)chlorin), a Second Generation Photosensitizer", Lead Structures for Applications in Photodynamic Therapy, vol. 87, pp. 1240-1296 (2011).

Shi, Z., et al., "Nitazoxanide inhibits the replication of Japanese encephalitis virus in cultured cells and in a mouse model", Virology Journal, vol. 11, No. 10, pp. 1-10 (2014).

Wang, Y., et al., "Antiviral activities of niclosamide and nitazoxanide against chikungunya virus entry and transmission", Antiviral Research, vol. 135, pp. 81-90 (2016).

Wu, H., et al., "Novel Dengue Virus NS2B/NS3 Protease Inhibitors", Antimicrobial Agents and Chemotherapy, vol. 59, No. 2, pp. 1100-1109 (2015).

Xu, M., et al., "Identification of small-molecule inhibitors of Zika virus infection and induced neural cell death via a drug repurposing screen", Nature Medicine, Advanced Online Publication, pp. 1-9 (2016).

Yung, C., et al., "Dengue Serotype-Specific Differences in Clinical Manifestation, Laboratory Parameters and Risk of Severe Disease in Adults, Singapore", Am. J. Trop. Med. Hyg., vol. 92, No. 5, pp. 999-1005 (2015).

\* cited by examiner

FIG. 1A

|    | 1 TBEV | 2 POWV | 3 YFV | 4 DENV2 | 5 DENV4 | 6 DENV1 | 7 DENV3 | 8 SLEV | 9 ZIKV | 10 WNV | 11 JEV |
|---|---|---|---|---|---|---|---|---|---|---|---|
| 1 TBEV | 100.00 | 74.43 | 40.56 | 44.24 | 42.94 | 44.38 | 45.54 | 39.33 | 43.00 | 39.33 | 37.04 |
| 2 POWV | 74.43 | 100.00 | 39.44 | 39.55 | 42.94 | 40.45 | 44.04 | 38.76 | 44.57 | 41.04 | 38.78 |
| 3 YFV | 40.56 | 39.00 | 100.00 | 50.41 | 50.83 | 57.73 | 54.04 | 53.33 | 53.33 | 53.33 | 54.14 |
| 4 DENV2 | 44.24 | 39.55 | 50.41 | 100.00 | 54.83 | 69.83 | 69.83 | 58.42 | 56.42 | 55.87 | 49.99 |
| 5 DENV4 | 42.94 | 42.94 | 50.83 | 54.83 | 100.00 | 64.83 | 75.00 | 56.68 | 56.00 | 55.73 | 53.85 |
| 6 DENV1 | 44.38 | 40.45 | 57.73 | 69.83 | 64.83 | 100.00 | 75.00 | 56.44 | 55.14 | 53.33 | 49.44 |
| 7 DENV3 | 45.54 | 44.04 | 54.04 | 69.83 | 75.00 | 75.00 | 100.00 | 56.44 | 55.14 | 53.33 | 49.44 |
| 8 SLEV | 39.33 | 38.76 | 53.33 | 58.42 | 56.68 | 56.44 | 56.44 | 100.00 | 58.14 | 58.33 | 53.85 |
| 9 ZIKV | 43.00 | 44.57 | 53.33 | 56.42 | 56.00 | 55.14 | 55.14 | 58.14 | 100.00 | 66.00 | 59.44 |
| 10 WNV | 39.33 | 41.04 | 53.33 | 55.87 | 55.73 | 57.73 | 53.33 | 58.33 | 66.00 | 100.00 | 72.78 |
| 11 JEV | 37.04 | 38.78 | 54.14 | 49.99 | 53.85 | 49.44 | 49.44 | 53.85 | 59.44 | 72.78 | 100.00 |

FIG. 1B

PHARMACEUTICAL COMPOSITIONS WITH ANTIFLAVIVIRAL ACTIVITY

CROSS REFERENCE TO RELATED APPLICATIONS

This application is a national stage filing under 35 U.S.C. § 371 of International Application No. PCT/US2017/039071, filed on Jun. 23, 2017, published as WO 2017223491 on Dec. 28, 2017, and claims priority under 35 U.S.C. § 119 to U.S. Provisional Application No. 62/353,887, filed Jun. 23, 2016, which is herein incorporated by reference in its entirety, and U.S. Provisional Application No. 62/362,884, filed Jul. 15, 2016, which is herein incorporated by reference in its entirety, and U.S. Provisional Application No. 62/461,492, filed Feb. 21, 2017, which is herein incorporated by reference in its entirety. The entire disclosures of each of the said applications are incorporated by reference in their entireties herein.

SEQUENCE LISTING

The instant application contains a Sequence Listing, created on Dec. 11, 2018; the file, in ASCII format, is designated H1353579.txt and is 21 KB in size. The file is hereby incorporated by reference in its entirety into the instant application.

FIELD OF THE INVENTION

The present invention relates to, inter alia, compositions possessing antiflaviviral qualities and uses as treatment for or prevention of flaviviral infection.

BACKGROUND OF THE INVENTION

The genus *Flavivirus* is includes many species of viruses, referred to herein as flaviviruses. Many flaviviruses cause serious and deadly human diseases, as well as serious diseases in non-human animals such as various species of cattle. For example, yellow fever virus (YFV), West Nile virus (WNV), Zika virus (ZIKV), Japanese encephalitis virus (JEV), Murray Valley encephalitis virus (MVEV), tick-borne encephalitis virus (TBEV), Powassan virus (POWV), St. Louis encephalitis virus (SLEV), and Dengue viruses (DENV) such as the closely related Dengue virus serotype 1 (DENV1), Dengue virus serotype 2 (DENV2), Dengue virus serotype 3 (DENV3), and Dengue virus serotype 4 (DENV4), are globally emerging pathogens. The World Health Organization (WHO) has estimated annual human cases of more than 390 million, 200,000, and 68,000 for DENV, YFV, and JEV, respectively. Approximately 3.9 billion people are at risk of DENV infection. Significant outbreaks of ZIKV, an emerging mosquito-borne flavivirus, initially occurred at Yap Island in 2007, French Polynesia in 2013, Easter Island in 2014, and most recently Brazil in 2015. Quickly, the virus emerged in and was imported to many new territories such as UK, Canada, USA, etc., presumably due to global travels. Recently it was also reported that ZIKV can be transmitted through sexual activities and blood transfusions. Importantly, increasing evidence suggests that ZIKV infections are linked to Guillain-Barré syndrome, as well as an increase in babies born with microcephaly. Infection with flaviviruses may occur through mosquito-borne transmission or transfusions of infected blood or transplantation of infected organs or tissues.

These associations strongly suggests that ZIKV infection during pregnancy might cause severe neurological damage in neonates. WHO has declared ZIKV as a global public health emergency. Although effective vaccines exist for YFV, JEV, and TBEV, there are currently no safe and effective vaccines for WNV, DENV, and ZIKV. Furthermore, due to the dangers and difficulties inherent in mass vaccination of large at-risk populations, it is desirable to be able to treat severe flavivirus (e.g., Zika virus, Dengue virus, Japanese encephalitis virus, West Nile virus, Murray Valley encephalitis virus, tick-borne encephalitis virus, Kyasanur Forest disease virus, Alfuy virus, Kunjin virus, yellow fever virus, St. Louis encephalitis virus, Japanese encephalitis virus, Spondweni virus, or Powassan virus, and all subtypes of the foregoing flavivirus species, including, for example, Alfuy virus and Kunjin virus) infections with antiviral therapeutics that could be administered to infected individuals who may not have received vaccinations.

Thus, pharmacological treatments for individuals infected with flaviviruses, including DENV1, DENV2, DENV3, DENV4, YFV, WNV, ZIKV, JEV, TBEV, POWV, and SLEV, and other species within the *Flavivirus* genus (i.e., flaviviruses) are needed. Also needed are compounds for the inhibition of flavivirus replication and assays for identifying such compounds, such as for elucidating molecular mechanisms responsible for 1 replication and ultimate infectious activity and for identifying improvements in interfering with such mechanisms.

SUMMARY OF THE INVENTION

In one aspect, the present disclosure relates to, inter alia, a method of inhibiting viral replication including contacting one or more cells that have been infected with a virus with an effective amount of a compound, wherein the compound is

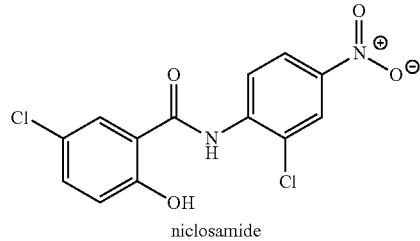 [SMILES: O=C(Nc1ccc([N+](=O)[O-])cc1Cl)c1cc(Cl)ccc1O]

niclosamide or a pharmaceutically acceptable salt thereof and the virus comprises a flavivirus. In an embodiment, contacting one or more cells that have been infected with a flavivirus includes administering the compound to a subject. In some examples, the subject may be a mammal, or may be a human, or other subject. In some embodiments, the virus may be Zika virus. In further embodiments, the cells may include tissue that has been removed from a mammal, or from a human, or from another organism or ex vivo or in vitro source of cells. In some embodiments, the flavivirus is selected from a group including Dengue virus serotype 1, Dengue virus serotype 2, Dengue virus serotype 3, Dengue virus serotype 4, yellow fever virus, West Nile virus, Zika virus, Japanese encephalitis virus, and any combination of two or more of the foregoing. All combinations of any one or more elements of any one or more the foregoing embodiments with any other one or more elements thereof are explicitly intended to be and are included within the present disclosure.

In another aspect, the present disclosure relates to, inter alia, a method of inhibiting viral replication including contacting one or more cells that have been infected with a virus with an effective amount of a compound, wherein the compound is selected from a group including

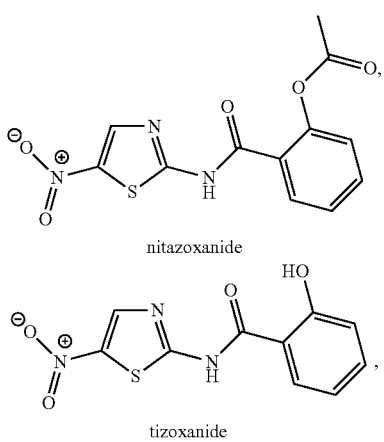

nitazoxanide tizoxanide pharmaceutically acceptable salts thereof, and any combination of two or more of the foregoing; and the virus includes Zika virus. In some embodiments, the compound may be nitazoxanide or a pharmaceutically acceptable salt thereof. In other embodiments, the compound may be tizoxanide or a pharmaceutically acceptable salt thereof. In further embodiments, contacting one or more cells that have been infected with a flavivirus includes administering the compound to a subject. A subject may be a mammal, a human, or another subject. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In yet another aspect, the present disclosure relates to, inter alia, a method of inhibiting viral replication including contacting one or more cells that have been infected with a virus with an effective amount of a compound, wherein the compound is

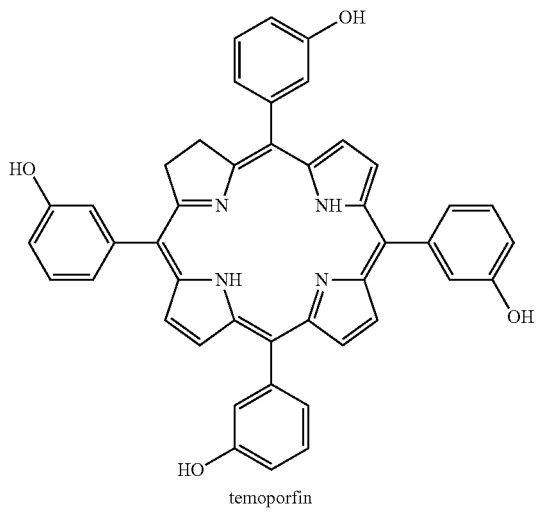 [SMILES: Oc1cccc(-c2c3nc(c(-c4cccc(O)c4)c4ccc([nH]4)c(-c4cccc(O)c4)c4nc(c(-c5cccc(O)c5)c5ccc2[nH]5)CC4)C=C3)c1]

temoporfin or a pharmaceutically acceptable salt thereof and the virus includes a flavivirus. In an embodiment, contacting one or more cells that have been infected with a flavivirus includes administering the compound to a subject. The subject may be a mammal, a human, or another subject. In another embodiment, the virus may be Dengue virus serotype 1, Dengue virus serotype 2, Dengue virus serotype 3, Dengue virus serotype 4, yellow fever virus, West Nile virus, Zika virus, Powassan virus, St. Louis encephalitis virus, Japanese encephalitis virus, Zika virus, and any combination of two or more of the foregoing. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In yet another aspect, the present disclosure relates to, inter alia, a method of inhibiting viral replication including contacting one or more cells that have been infected with a virus with an effective amount of a compound, wherein the compound may include

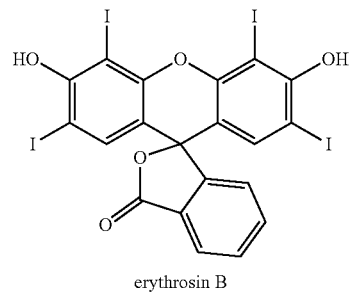 [SMILES: O=C1OC2(c3ccccc31)c1cc(I)c(O)c(I)c1Oc1c2cc(I)c(O)c1I]

erythrosin B or a pharmaceutically acceptable salt thereof and the virus includes a flavivirus. In an embodiment, contacting one or more cells that have been infected with a flavivirus may include administering the compound to a subject. The subject may be a mammal, a human, or other subject. In a further embodiment, the flavivirus may be selected from a group including Dengue virus serotype 1, Dengue virus serotype 2, Dengue virus serotype 3, Dengue virus serotype 4, Zika virus, and any combination of two or more of the foregoing. In a specific embodiment, the virus may be Zika virus. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In a still further aspect, the present disclosure relates to, inter alia, a method of inhibiting viral replication including contacting one or more cells that have been infected with a virus with an effective amount of a compound, wherein the compound is selected from a group including

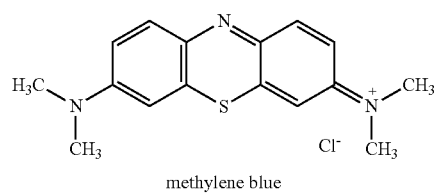

methylene blue a pharmaceutically acceptable salt thereof, and any combination of two or more of the foregoing, and the virus includes a flavivirus and the flavivirus is selected from a group consisting of Dengue virus serotype 1, Dengue virus serotype 2, Dengue virus serotype 3, Dengue virus serotype 4, Zika virus, and any combination of two or more of the foregoing. In a specific embodiment, the virus may include Zika virus. In an embodiment, contacting one or more cells that have been infected with a flavivirus comprises administering the compound to a subject. The subject may be a mammal, a human, or another subject. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In yet another aspect, the present disclosure relates to, inter alia, a method of inhibiting viral replication including contacting one or more cells that have been infected with a virus with an effective amount of a compound, wherein the compound is selected from a group including nitazoxanide, tizoxanide, niclosamide, temoporfin, erythrosine B, methylene blue, pharmaceutically acceptable salts thereof, and any combination of two or more of the foregoing, and the virus includes Zika virus. In an embodiment, contacting one or more cells that have been infected with a flavivirus comprises administering the compound to a subject. The subject may be a mammal, a human, or another subject. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In still a further aspect, the present disclosure relates to, inter alia, a method of inhibiting viral replication including contacting one or more cells that have been infected with a virus with an effective amount of a compound, wherein the compound is selected from a group including nuclosamide, temoporfin, erythrosine B, methylene blue, pharmaceutically acceptable salts thereof, and any combination of two or more of the foregoing, and the virus includes a flavivirus and the flavivirus is selected from a group including Dengue virus serotype 1, Dengue virus serotype 2, Dengue virus serotype 3, Dengue virus serotype 4, or any combination of two or more of the foregoing. In an embodiment, contacting one or more cells that have been infected with a flavivirus comprises administering the compound to a subject. The subject may be a mammal, a human, or another subject. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

In yet another aspect, the present disclosure relates to, inter alia, a method of inhibiting viral replication including contacting one or more cells that have been infected with a virus with an effective amount of a compound, wherein the compound is selected from a group including niclosamide, temoporfin, pharmaceutically acceptable salts thereof, and any combination of two or more of the foregoing, and the virus includes a flavivirus and the flavivirus is selected from a group including West Nile virus, Japanese encephalitis virus, yellow fever virus, and any combination of two or more of the foregoing. In an embodiment, contacting one or more cells that have been infected with a flavivirus comprises administering the compound to a subject. The subject may be a mammal, a human, or another subject. In further embodiments, the cells may include tissue that has been removed from a mammal, or from a human, or from another organism or ex vivo or in vitro source of cells. All combinations of any one or more elements of any one or more the foregoing embodiments with any other one or more elements thereof are explicitly intended to be and are included within the present disclosure.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which:

FIG. 1A shows the alignment of amino acid sequences of the NS3 proteins from flaviviruses DENV1, DENV2, DENV3, DENV4, YFV, WNV, ZIKV, JEV, TBEV, POWV, and SLEV.

FIG. 1B shows the amino acid sequence homologies between flaviviruses DENV1, DENV2, DENV3, DENV4, YFV, WNV, ZIKV, JEV, TBEV, POWV, and SLEV.

FIGS. 35B, 35D, and 35F are graphs showing NS3 expression (lower bands from FIGS. 35A, 35C, and 35E) normalized to the GAPDH loading control, and accumulated viral polyprotein precursor (PP) normalized to DMSO control.

DETAILED DESCRIPTION OF THE INVENTION

Figure 2A:
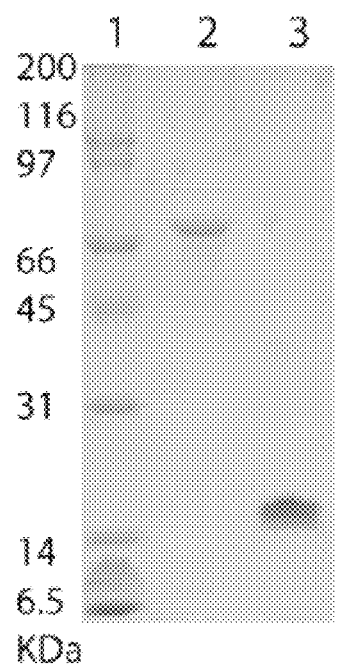
FIG. 2A shows a sodium dodecyl sulfate polyacrylamide gel electrophoresis (SDS PAGE) of His-tagged DENV2 NS2B protein (His-NS2B) and His-tagged maltose-binding protein (MBP) fused to DENV2 NS3 protein (His-MBP-NS3).

Aspects of an invention disclosed herein and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating some embodiments, are given by way of illustration only, and are not by way of limitation. Various substitutions, modifications, additions and/or arrangements within the spirit and/or scope of the underlying inventive concepts will be apparent to those skilled in the art from this disclosure.

The present disclosure relates to, inter alia, compositions and methods for inhibiting replication of flaviviruses, including treating subjects infected with flaviviruses, compounds for use in such methods, and methods for evaluating the effectiveness of compounds in inhibiting flaviviral replication. As used herein, the term "flavivirus" means all species of viruses in the *Flavivirus* genus according to the International Committee on Taxonomy of Viruses Master Species List 2016 v1.3, dated May 25, 2017, including Apoi virus, Aroa virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Sal Vieja virus, San Perlita virus, Saumarez Reef virus, Sepik virus, St. Louis encephalitis virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and Zika virus, and all recognized subtypes of the foregoing species (e.g., DENV1, DENV2, DENV3, DENV4, Alfuy virus and Kunjin virus).

*Flavivirus* genomic RNA is single-stranded and of positive (i.e., mRNA) polarity. The viral genome is approximately 11 kb in length, consisting of a 5' UTR, a single long open reading frame (ORF), and a 3' UTR. The single ORF encodes a polyprotein that is co- and post-translationally processed by viral and cellular proteases into individual functional proteins. Among the flaviviral proteins, NS3 is a multi-functional protein with activities of a serine protease, an RNA triphosphatase, a nucleoside triphosphatase, and a helicase. The viral protease is a complex with two components: the N-terminal 184 amino acids (aa) of viral NS3 protein and a hydrophobic core of about 40 aa in length within viral NS2B protein as an essential cofactor for flaviviral protease activity and replication.

Figure 1A:
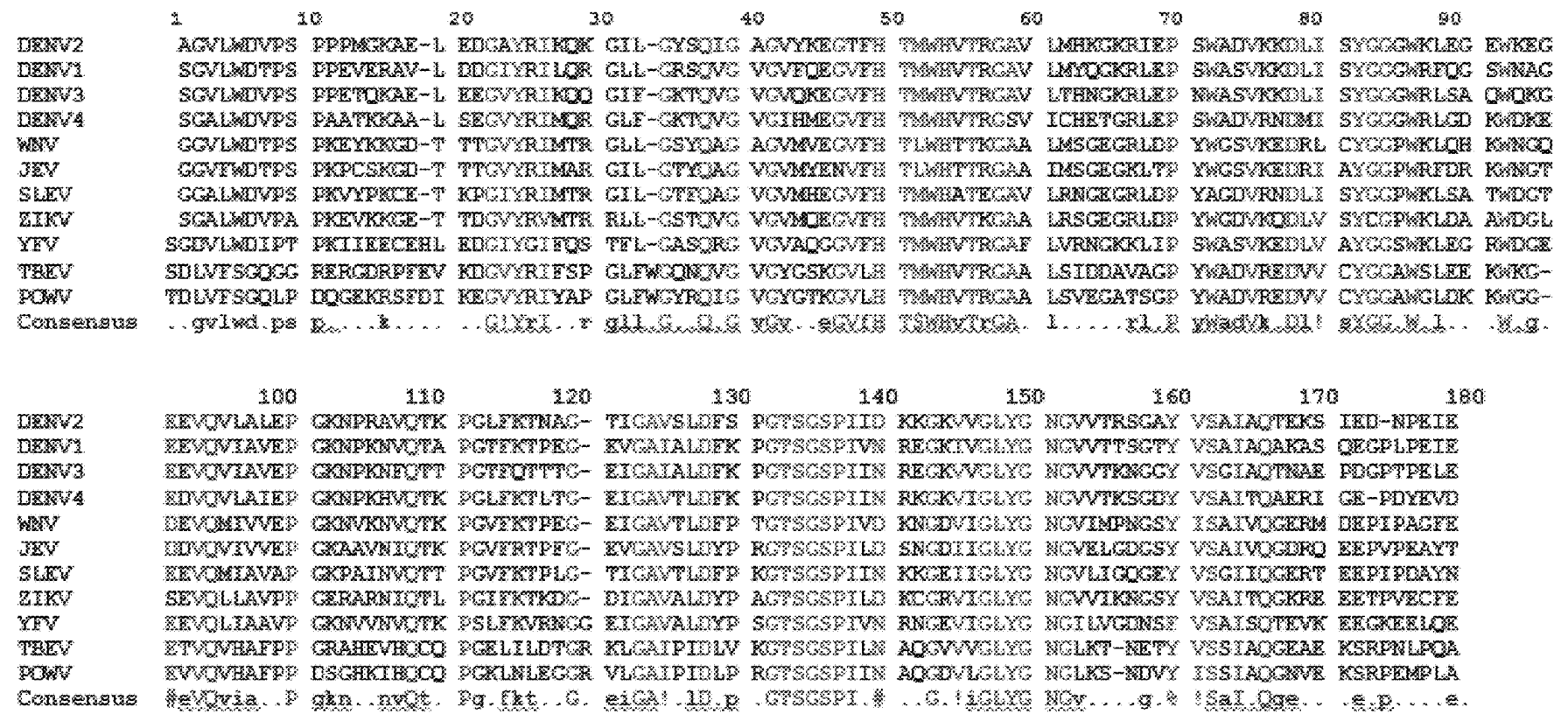

The flavivirus NS2B-NS3 protease is a highly conserved and replication-critical enzyme. See Noble et al., 2012, Journal of Virology 86, 438-446; Prusis, P. et al., 2008, Bioorganic & Medicinal Chemistry 16, 9369-9377; Chambers et al., 1991, J. Virol. 65, 6042-6050; Falgout et al., 1991, J Virol 65, 2467-2475; Lescar et al. 2008, Antiviral Res 80, 94-101. FIG. 1A shows the conservation of amino acid residues at positions along the NS3 proteins of various flaviviruses and their consensus sequence (SEQ ID NO:1 DENV2 NS3; SEQ ID NO:2 DENV1 NS3; SEQ ID NO:3 DENV3 NS3; SEQ ID NO:4 DENV4 NS3; SEQ ID NO:5 WNV NS3; SEQ ID NO:6 JEV NS3; SEQ ID NO:7 SLEV NS3; SEQ ID NO:8 ZIKV NS3; SEQ ID NO:9 YFV NS3; SEQ ID NO: 10 TBEV NS3; SEQ ID NO:11 POWV NS3. As shown in FIG. 1B, the NS3 proteins of flaviviruses show very high sequence homology, indicating high structural similarity among flaviviral NS3 proteins.

The NS2B/NS3 flaviviral protease works with host proteases to cleave the polyprotein precursor produced by the viral genome. Noble et al., (2008), Journal of Virology 86, 438-446; Prusis et al. (2008), Bioorganic & Medicinal Chemistry 16, 9369-9377; Chambers et al. (1991), J. Virol. 65, 6042-6050; Falgout et al. (1991), J Virol 65, 2467-2475; Lescar et al. (2008), Antiviral Res 80, 94-101. The flavivirus protease is a trypsin-like serine protease that preferentially cleaves protein substrates at sites immediately following two basic residues (K or R at positions P2 and P1). Crystal structures of the NS2B-NS3 proteases of flaviviruses in covalently-linked forms (e.g. NS2B-$G_4SG_4$linker-NS3) have been determined in both apo and inhibitor-bound forms. Aleshin et al. (2007), Protein Sci. 16, 795-806; Assenberg et al. (2009), J Virol 83, 12895-12906; Chandramouli et al. (2010), J Virol 84, 3059-306; Erbel et al. (2006), Nat. Struct. Mol. Biol. 13, 372-373; Hammamy et al. (2013), ChemMedChem 8, 231-241; Luo et al. (2010), J Biol Chem 285, 18817-18827; Luo et al. (2008), J Virol 82, 173-183; Luo et al. (2008), Embo J 27, 3209-3219; Noble et al. (2012), J Virol 86, 438-446; Robin et al. (2009), J Mol Biol 385, 1568-1577. In the absence of substrate or active site inhibitor, the N-terminal but not C-terminal portion of NS2B is bound to NS3; whereas the conformation of the C-terminal portion of NS2B varies considerably, presumably in the "open" inactive conformations. Upon inhibitor or substrate binding to the NS3 active site, the C-terminal portion of NS2B "wraps around" the NS3 core, closing the NS3 active site with the so-called active "closed" conformation. The conformation of the N-terminal portion of NS2B remains the same as that of apo form. NS2B binding and conformational change are required for NS3 function;

mutations that abrogate NS2B binding greatly reduce the proteolytic activity of the complex. Chappell et al. (2008) J Gen Virol 89, 1010-1014; Niyomrattanakit et al. (2004), J Virol 78, 13708-13716.

In addition, the conformational change of NS2B upon active site inhibitor binding has been verified by a number of NMR studies using the linked construct and by molecular dynamic studies. Su et al. (2009), PLoS Negl Trop Dis 3, e561; Su et al. (2009), FEBS J 276, 4244-4255; Ekonomiuk & Caflisch (2009), Protein Sci 18, 1003-1011; Kang et al. (2013), Antiviral Res 97, 137-144; Zhu et al. (2015), Biochem Biophys Res Commun 461, 677-680. Co-expression of unlinked NS2B-NS3 protease was developed, and NMR studies indicated that NS2B in the unlinked protease mainly adopted the "closed" conformation even in the absence of substrate analogs. Chen et al. (2014), FEBS Lett 588, 2206-2211; Kim et al. (2013), J Biol Chem 288, 12891-12900; Li et al (2014), FEBS Lett 588, 2794-2799; de la Cruz et al. (2011), J Am Chem Soc 133, 19205-19215; de la Cruz et al. (2014), FEBS J 281, 1517-1533.

For flavivirus protease, two regions of NS2B (N-terminal (Nter): amino acids (aa) 53-61 and C-terminal (Cter): aa 74-86) are critical for the protease function. Chappell et al. (2008), J Gen Virol 89, 1010-1014; Niyomrattanakit et al. (2004), J Virol 78, 13708-13716; Radichev et al. (2008), J Gen Virol 89, 636-641; Phong et al. (2011), Biosci Rep. It has also been demonstrated that NS2B Nter residues display similar conformations in all structures. Brecher et al. (2013), Virol Sin. 28, 326-336. In addition, the NS2B aa 49-66 only (Cter-deletion) peptide is sufficient to stabilize the NS3 conformation. Luo et al. (2008), J Virol 82, 173-183; Luo et al. (2010), J Biol Chem 285, 18817-18827. Moreover, unlike the active site which is flat and featureless, the NS3 pockets holding the NS2B Nter residues (such as key contact residues L51, V53, V59 and W61) are deep and hydrophobic Attempts to develop flavivirus protease inhibitors have focused on the NS3 active site but have not been very successful. As disclosed herein, rather than focusing on the active site, screens were used to identify compounds that orthosterically inhibit NS3 function. As disclosed herein, an HTS assay was used to identify orthosteric inhibitors to impair NS2B-NS3 interactions. Using this strategy, six candidate compounds were identified that can significantly inhibited the interactions between NS2B and NS3. These compounds not only inhibited the protease activity but also significantly reduce titers of ZIKV, DENV1, DENV2, DENV3, DENV4, WNV, YFV, POWV, and JEV. Given the high structural similarity of the NS2B/NS3 complex amongst flaviviruses, such as shown in FIGS. 1A and 1B, skilled artisans would appreciate that comparable results would likely be observed with other flaviviruses. Compounds are herein disclosed that can inhibited the growth of all flaviviruses tested with low nanomolar efficacy.

Using an HTS assay as disclosed herein, the NCGC Pharmaceutical collection that harbors about 2,800 drugs approved for administration to human subjects by the FDA of the United States or other countries was screened for potential inhibitors of flaviviral replication as potential medical treatments for flaviviral infection. The HTS identified 23 candidate inhibitors that abolished the NS2B-NS3 SLC signals with IC50 values lower than 15 µM (IC50, compound concentration required to inhibit 50% of a reaction), as shown in Table 1:

TABLE 1

Candidate inhibitors blocking NS2B-NS3 interactions.

| Compounds | SLC $IC_{50}$ (µM) | NS2B-MBP-NS3 protease $IC_{50}$ (µM) | $CC_{50}$ (µM) | $EC_{50}$ (µM) (DENV2) | Therapeutic index (TI) ($CC_{50}/EC_{50}$) |
|---|---|---|---|---|---|
| Ataluren | 0.1 | 21.6 | >100 | <2 | >50 |
| Frentizole | 0.38 | | | | |
| Niclosamide | 0.7 | 12.3 | >100 | 0.55 | >182 |
| Nitazoxanide | 3.4 | 15.9 | >100 | <10 | >10 |
| Amlenanox | 4.7 | | | | |
| Tenonitrozole | 4.9 | | | | |
| Axitinib | 5.3 | | | | |
| Ipriflavone | 5.3 | | | | |
| Methylene blue | 5.5 | 41.6 | >100 | <2 | >50 |
| Genistein | 7.2 | | | | |
| Pifexole | 7.5 | | | | |
| 2-(2H-Benzo-triazol-2-yl)-4-methylphenol | 7.8 | | | | |
| Resveratrol | 9 | | | | |
| Carbocyanine | 10.1 | | | | |
| Temoporfin | 11.2 | 0.76 | 40.7 | 0.073 | 558 |
| Zolimidine | 12.1 | | | | |
| Isosulfan blue | 12.2 | | | | |
| Fanetizole | 12.4 | | | | |
| 4-Aminoazobenzene | 12.6 | | | | |
| Phenazopyridine hydrochloride | 13.2 | | | | |
| Toluidine blue | 14.3 | | | | |
| Padimate | 14.4 | | | | |
| Erythrosin B | 15 | 1.9 | >100 | <10 | >10 |

The 23 compounds were then subjected to protease inhibition assay. Several compounds effectively inhibited NS2B-NS3 protease activity with IC50 values ranging from 0.76 µM to 41.6 µM (Table 1). Coupled with low toxicity to cells at doses with high antiflaviviral activity, these compounds showed high therapeutic indices as potential compounds for inhibition of interaction of flaviviral NS2B with flaviviral NS3, of flaviviral NS2B/NS3 protease activity, and flaviviral replication and treatment of subjects with flaviviral infection, such as with ZIKV, DENV1, DENV2, DENV3, DENV4, WNV, YFV, JEV, TBEV, POWV or SLEV. Approval of these compounds for other medical uses at known dosage concentrations within effective ranges for purposes disclosed herein indicates their clinical suitability as antiflaviviral medication.

Accordingly, in one aspect, disclosed herein is a method of inhibiting viral replication including contacting one or more cells that have been infected with a flavivirus with an effective amount of a compound which may include

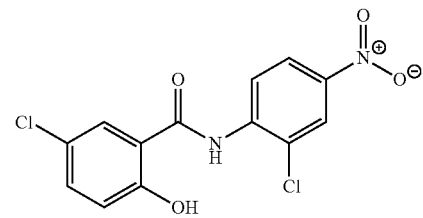

niclosamide (5-chloro-N-(2-chloro-4-nitrophenyl)-2-hyroxybenzamide

-continued

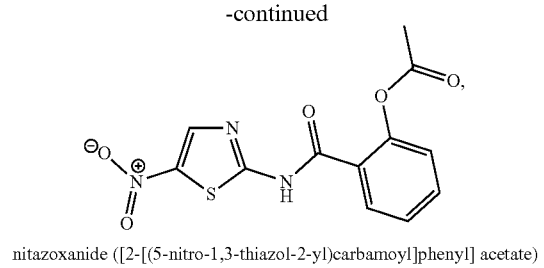

nitazoxanide ([2-[(5-nitro-1,3-thiazol-2-yl)carbamoyl]phenyl] acetate)

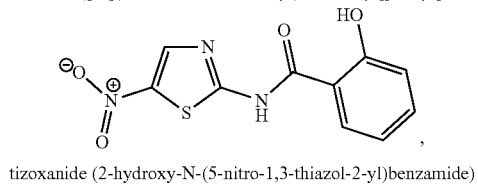

tizoxanide (2-hydroxy-N-(5-nitro-1,3-thiazol-2-yl)benzamide)

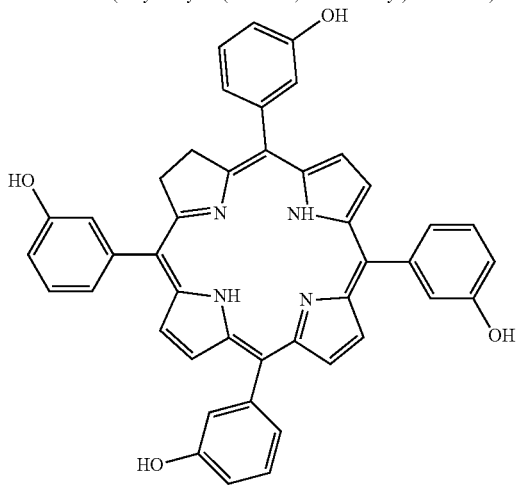

temoporfin (3-[10,15,20-tris(3-hydroxyphenyl)-2,3,22,24-tetrahydroporphyrin-5-yl]phenol)

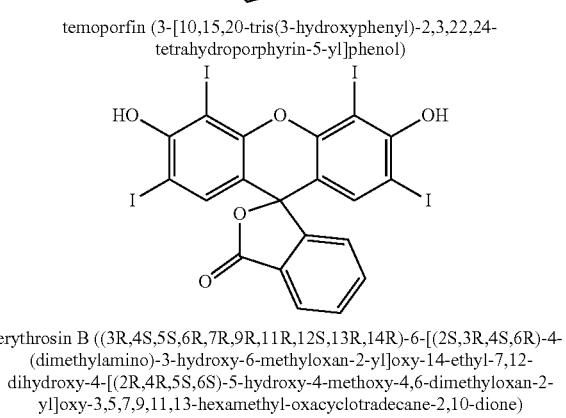

erythrosin B ((3R,4S,5S,6R,7R,9R,11R,12S,13R,14R)-6-[(2S,3R,4S,6R)-4-(dimethylamino)-3-hydroxy-6-methyloxan-2-yl]oxy-14-ethyl-7,12-dihydroxy-4-[(2R,4R,5S,6S)-5-hydroxy-4-methoxy-4,6-dimethyloxan-2-yl]oxy-3,5,7,9,11,13-hexamethyl-oxacyclotradecane-2,10-dione)

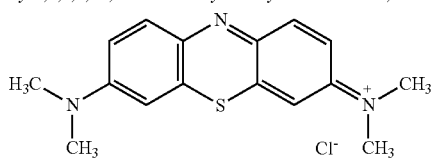

methylene blue ([7-(dimethylamino)phenothiazin-3-ylidene]-dimethylazanium;chloride), and pharmaceutically acceptable salts thereof.

The foregoing compounds may possess one or more centers of chirality. Various examples of each of such compounds may differ from one another by nature of their stereochemistry at one or more chiral center. A given compound may therefore exist in a stereochemically pure state, consisting of a single stereoisomer, or include a racemic mixture of different enantiomers that possess different stereochemistry at one or more chiral center from each other. Notwitstanding any chemical identities disclosed in the foregoing paragraphs, also included within the present disclosure are compounds which may include a racemic mixture of various stereoisomers of the foregoing compounds or may include isolates of a given stereoisomer of a given compound, identical to or different from any particular stereoisomer specifically identified herein.

Optionally, contacting one or more cells that have been infected with a flavivirus may include administering the compound to a subject, which may be a mammal, a human, or another subject. The flavivirus may be DENV1, DENV2, DENV3, DENV4, YFV, WNV, ZIKV, POWV, SLEV, TBEV, or JEV, or any other flavivirus. For example, the compound may be temoporfin or a pharmaceutically acceptable salt thereof and the flavivirus may be DENV1, the compound may be temoporfin or a pharmaceutically acceptable salt thereof and the flavivirus may be DENV2, the compound may be temoporfin or a pharmaceutically acceptable salt thereof and the flavivirus may be DENV3, the compound may be temoporfin or a pharmaceutically acceptable salt thereof and the flavivirus may be DENV4, the compound may be temoporfin or a pharmaceutically acceptable salt thereof and the flavivirus may be YFV, the compound may be temoporfin or a pharmaceutically acceptable salt thereof and the flavivirus may be WNV, the compound may be temoporfin or a pharmaceutically acceptable salt thereof and the flavivirus may be ZIKV, the compound may be temoporfin or a pharmaceutically acceptable salt thereof and the flavivirus may be POWV, the compound may be temoporfin or a pharmaceutically acceptable salt thereof and the flavivirus may be SLEV, the compound may be temoporfin or a pharmaceutically acceptable salt thereof and the flavivirus may be TBEV, or the compound may be temoporfin or a pharmaceutically acceptable salt thereof and the flavivirus may be JEV.

In another example, the compound may be niclosamide or a pharmaceutically acceptable salt thereof and the flavivirus may be DENV1, the compound may be niclosamide or a pharmaceutically acceptable salt thereof and the flavivirus may be DENV2, the compound may be niclosamide or a pharmaceutically acceptable salt thereof and the flavivirus may be DENV3, the compound may be niclosamide or a pharmaceutically acceptable salt thereof and the flavivirus may be DENV4, the compound may be niclosamide or a pharmaceutically acceptable salt thereof and the flavivirus may be YFV, the compound may be niclosamide or a pharmaceutically acceptable salt thereof and the flavivirus may be WNV, the compound may be niclosamide or a pharmaceutically acceptable salt thereof and the flavivirus may be ZIKV, the compound may be niclosamide or a pharmaceutically acceptable salt thereof and the flavivirus may be POWV, the compound may be niclosamide or a pharmaceutically acceptable salt thereof and the flavivirus may be SLEV, the compound may be niclosamide or a pharmaceutically acceptable salt thereof and the flavivirus may be TBEV, or the compound may be niclosamide or a pharmaceutically acceptable salt thereof and the flavivirus may be JEV.

In yet another example, the compound may be nitazoxanide or a pharmaceutically acceptable salt thereof and the flavivirus may be DENV1, the compound may be nitazoxanide or a pharmaceutically acceptable salt thereof and the flavivirus may be DENV2, the compound may be nitazoxanide or a pharmaceutically acceptable salt thereof and the flavivirus may be DENV3, the compound may be nitazoxanide or a pharmaceutically acceptable salt thereof and the flavivirus may be DENV4, the compound may be nitazoxanide or a pharmaceutically acceptable salt thereof and the flavivirus may be YFV, the compound may be nitazoxanide or a pharmaceutically acceptable salt thereof and the flavivirus may be WNV, the compound may be nitazoxanide or a pharmaceutically acceptable salt thereof and the flavivirus may be ZIKV, the compound may be nitazoxanide or a pharmaceutically acceptable salt thereof and the flavivirus may be POWV, the compound may be nitazoxanide or a pharmaceutically acceptable salt thereof and the flavivirus may be SLEV, the compound may be nitazoxanide or a pharmaceutically acceptable salt thereof and the flavivirus may be TBEV, or the compound may be nitazoxanide or a pharmaceutically acceptable salt thereof and the flavivirus may be JEV.

Nitazoxanide may be metabolized in vivo to a metabolie tizoxanide. Some effects of nitazoxanide may result from metabolism of nitazoxanide to tizoxanide and activity of tizoxanide. Thus, in a still further example, the compound may be tizoxanide or a pharmaceutically acceptable salt thereof and the flavivirus may be DENV1, the compound may be tizoxanide or a pharmaceutically acceptable salt thereof and the flavivirus may be DENV2, the compound may be tizoxanide or a pharmaceutically acceptable salt thereof and the flavivirus may be DENV3, the compound may be tizoxanide or a pharmaceutically acceptable salt thereof and the flavivirus may be DENV4, the compound may be tizoxanide or a pharmaceutically acceptable salt thereof and the flavivirus may be YFV, the compound may be tizoxanide or a pharmaceutically acceptable salt thereof and the flavivirus may be WNV, the compound may be tizoxanide or a pharmaceutically acceptable salt thereof and the flavivirus may be ZIKV, the compound may be tizoxanide or a pharmaceutically acceptable salt thereof and the flavivirus may be POWV, the compound may be tizoxanide or a pharmaceutically acceptable salt thereof and the flavivirus may be SLEV, the compound may be tizoxanide or a pharmaceutically acceptable salt thereof and the flavivirus may be TBEV, or the compound may be tizoxanide or a pharmaceutically acceptable salt thereof and the flavivirus may be JEV.

In another example, the compound may be erythrosin B or a pharmaceutically acceptable salt thereof and the flavivirus may be DENV1, the compound may be erythrosin B or a pharmaceutically acceptable salt thereof and the flavivirus may be DENV2, the compound may be erythrosin B or a pharmaceutically acceptable salt thereof and the flavivirus may be DENV3, the compound may be erythrosin B or a pharmaceutically acceptable salt thereof and the flavivirus may be DENV4, the compound may be erythrosin B or a pharmaceutically acceptable salt thereof and the flavivirus may be YFV, the compound may be erythrosin B or a pharmaceutically acceptable salt thereof and the flavivirus may be WNV, the compound may be erythrosin B or a pharmaceutically acceptable salt thereof and the flavivirus may be ZIKV, the compound may be erythrosin B or a pharmaceutically acceptable salt thereof and the flavivirus may be POWV, the compound may be erythrosin B or a pharmaceutically acceptable salt thereof and the flavivirus may be SLEV, the compound may be erythrosin B or a pharmaceutically acceptable salt thereof and the flavivirus may be TBEV, or the compound may be erythrosin B or a pharmaceutically acceptable salt thereof and the flavivirus may be JEV.

In yet another example, the compound may be methylene blue or a pharmaceutically acceptable salt thereof and the flavivirus may be DENV1, the compound may be methylene blue or a pharmaceutically acceptable salt thereof and the flavivirus may be DENV2, the compound may be methylene blue or a pharmaceutically acceptable salt thereof and the flavivirus may be DENV3, the compound may be methylene blue or a pharmaceutically acceptable salt thereof and the flavivirus may be DENV4, the compound may be methylene blue or a pharmaceutically acceptable salt thereof and the flavivirus may be YFV, the compound may be methylene blue or a pharmaceutically acceptable salt thereof and the flavivirus may be WNV, the compound may be methylene blue or a pharmaceutically acceptable salt thereof and the flavivirus may be ZIKV, the compound may be methylene blue or a pharmaceutically acceptable salt thereof and the flavivirus may be POWV, the compound may be methylene blue or a pharmaceutically acceptable salt thereof and the flavivirus may be SLEV, the compound may be methylene blue or a pharmaceutically acceptable salt thereof and the flavivirus may be TBEV, or the compound may be methylene blue or a pharmaceutically acceptable salt thereof and the flavivirus may be JEV.

In all of the foregoing examples, any of the compounds identified may be administered before confirmation of the presence or infection of any of DENV1, DENV2, DENV3, DENV4, YFV, WNV, ZIKV, POWV, SLEV, TBEV, JEV, or any other flavivirus in a cell or cells or sample from a subject, including a human subject or other mammalian subject, with the effect of preventing infection. For example, a sample or subject may be suspected of having been exposed to a flavivirus and administration of one or more of the foregoing drugs may be applied so as to prevent replication of the virus or viruses should contact otherwise sufficient to cause viral replication or infection of the cells have been present. It should be noted that, notwithstanding an apparent mechanism of action of the foregoing drugs in preventing viral replication, preventing or reversing infection, spread, illness, etc., as disclosed herein, the present disclosure is not limited to preventing viral replication, preventing or reversing infection, spread, illness, etc., according to any particular mechanism of action, including any apparent mechanism of action disclosed herein. Any or all of the foregoing drugs may prevent flaviviral replication, prevent or reverse infection, spread, illness, etc., by any mechanism of action and still be included within the present disclosure, even if not by a mechanism of action disclosed herein. Antiflaviviral effects of temoporfin, niclosamide, tizoxanide, nitazoxanide, erythrosin B, or methylene blue may orruce by any mechanism, and identification of potential mechanism(s) of action identified herein in no way excludes mechanisms of action by which these compounds may exert antiflavivral effects, other than or including any mechanism disclosed herein, from falling within the scope of subject matter disclosed herein, without limitation as to any mechanism for such antiflaviviral effects not explicitly identified mechanistically.

Also provided herein is a pharmaceutical composition comprising a compound disclosed above, or a pharmaceutically acceptable salt form thereof, and a pharmaceutically acceptable carrier or diluent. While it may be possible for erythrosine B, temoporfin, niclosamide, nitazoxanide, tizoxanide, methylene blue, or pharmaceutically acceptable salts thereof to be administered as the raw chemical, it may be preferable to present them as a pharmaceutical composition. According to a further aspect, the present invention provides a pharmaceutical composition comprising erythrosine B, temoporfin, niclosamide, nitazoxanide, tizoxanide, methylene blue, or pharmaceutically acceptable salts thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

Any of the foregoing compounds may be used in accordance with the present disclosure to treat a subject, such as a human subject, infected with a flavivirus, such as one of the types of flaviviruses identified in the above paragraphs. For example, an amount of an anti-flavivirus therapeutic of the present disclosure, or a pharmaceutically acceptable salt of the compound, optionally in combination with a pharmaceutically acceptable excipient, carrier, or additive, sufficient to effectively treat a flaviviral infection may be administered to such subject. Use of any one or more of the foregoing compounds to treat infection with any one or more flaviviruses, including those specifically identified above, is explicitly contemplated and hereby included in the present disclosure.

In a further aspect, any of the foregoing compounds may be used in accordance with the present disclosure to prevent infection of a subject, such as a human subject, or other mammalian subject, with a flavivirus, such as one of the types of flaviviruses identified in the above paragraphs. For example, an amount of an anti-flavivirus therapeutic of the present disclosure, or a pharmaceutically acceptable salt of the compound, optionally in combination with a pharmaceutically acceptable excipient, carrier, or additive, sufficient to prevent flaviviral infection, may be administered to such subject. Use of any one or more of the foregoing compounds to prevent infection with any one or more flaviviruses, including those specifically identified above, is explicitly contemplated and hereby included in the present disclosure.

In another aspect, any of the foregoing compounds may be used in accordance with the present disclosure to prevent replication of a flavivirus, such as one of the types of flaviviruses identified in the above paragraphs. For example, such a flavivirus or a cell infected with such a flavivirus may be contacted with an amount of an anti-flavivirus compound of the present disclosure, or a pharmaceutically acceptable salt of the compound, optionally in combination with a pharmaceutically acceptable excipient, carrier, or additive, sufficient to prevent flaviviral replication, to prevent flaviviral replication. Use of any one or more of the foregoing compounds to prevent replication of one or more flaviviruses, including those specifically identified above, is explicitly contemplated and hereby included in the present disclosure.

In yet another aspect, any of the foregoing compounds may be used in accordance with the present disclosure to prevent protease activity of a flavivirus, such as one of the types of flaviviruses identified in the above paragraphs. For example, such a flavivirus or a cell infected with such a flavivirus may be contacted with an amount of an anti-flavivirus compound of the present disclosure, or a pharmaceutically acceptable salt of the compound, optionally in combination with a pharmaceutically acceptable excipient, carrier, or additive, sufficient to prevent protease activity of a flavivirus, such as NS2B/NS3 protease activity, to prevent protease activity of a flavivirus. Use of any one or more of the foregoing compounds to prevent protease activity of one or more flaviviruses, including those specifically identified above, is explicitly contemplated and hereby included in the present disclosure.

Formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association erythrosine B, temoporfin, niclosamide, nitazoxanide, tizoxanide, methylene blue, or pharmaceutically acceptable salts thereof ("active ingredient") with a carrier which constitutes one or more accessory ingredients. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

In certain embodiments, the active compounds may be incorporated with excipients and used in the form of ingestible tablets, buccal tablets, troches, capsules, elixirs, suspensions, syrups, wafers, and the like. Tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

A tablet may be made by compression or molding, optionally with one or more accessory ingredients. Compressed tablets may be prepared by compressing in a suitable machine an active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. Tablets may optionally be coated or scored and may be formulated so as to provide sustained, delayed or controlled release of an active ingredient therein.

Formulations for parenteral administration include aqueous and non-aqueous sterile injection solutions which may contain anti-oxidants, buffers, bacteriostats and solutes which render a formulation isotonic with the blood of the intended recipient. Formulations for parenteral administration also may include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The anti-flavivirus compound or anti-flavivirus compound derivative may comprise different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The anti-flavivirus compound or anti-flavivirus compound derivative may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice.

As used herein, the term "effective amount" means that amount of a drug or pharmaceutical agent that will elicit the biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of the anti-flavivirus compound of the present invention, as well as salts, solvates, and physiological functional derivatives thereof, may be administered as the raw chemical. Additionally, the active ingredient may be presented as a pharmaceutical composition.

Pharmaceutical compositions of the present invention comprise an effective amount of one or more anti-flavivirus compound or anti-flavivirus compound derivative, or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one anti-flavivirus compound or anti-flavivirus compound derivative, or additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition may be combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of pharmaceutical lipid vehicle compositions that include the anti-flavivirus compound or anti-flavivirus compound derivative, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the anti-flavivirus compound or anti-flavivirus compound derivative, may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

For example, a compound or compounds disclosed herein may be administered to a subject, such as a mammal, human, or other subject, to contact a cell or cells to prevent replication of a flavivirus, including stereoisomers, racemic mixtures, pharmaceutically acceptable salts, or in complex with an excipient(s) or pharmaceutically acceptable carrier(s) or otherwise formulated for such administration in accordance with the examples detailed in the foregoing paragraphs, in accordance with the present disclosure. All combinations of the foregoing are explicitly intended to be and are included as aspects in accordance with the present disclosure.

The actual dosage amount of a composition of the present invention administered to a subject (e.g., an animal or human patient) can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In preferred embodiments of the present invention, the anti-flavivirus compound or anti-flavivirus compound derivative are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the anti-flavivirus compound or anti-flavivirus compound derivative may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments of the invention, the anti-flavivirus compound or anti-flavivirus compound derivative may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described. Likewise, the delivery of drugs using intranasal microparticle resins and lysophosphatidylglycerol compounds are also well-known in the pharmaceutical arts. Likewise, transmucosal drug delivery in the form of a polytetrafluoroetheylene support matrix may be adopted for use in accordance with the present disclosure.

The term aerosol refers to a colloidal system of finely divided solid of liquid particles dispersed in a liquefied or pressurized gas propellant. An aerosol of the present invention for inhalation may consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In addition, compounds according to the present invention may be administered alone or in combination with other agents, including other compounds of the present invention.

Certain compounds according to the present invention may be effective for enhancing the biological activity of certain agents according to the present invention by reducing the metabolism, catabolism or inactivation of other compounds and as such, are co-administered for this intended effect.

EXAMPLES

The following examples are presented to further describe techniques in accordance with the method disclosed herein, but should not be read as limiting, because variations still within the scope of embodiments of the present invention will be apparent to those skilled in the art.

Compounds were obtained from various vendors. Temoporfin was purchased from Caymen Chemicals (Ann Arbor, Mich.); Niclosamide, nitazoxanide, methylene blue, and erythrosin B were from Sigma-Aldrich (St. Louis, Mo.).

Primers used are disclosed in Table 2:

TABLE 2

| Primers used | |
|---|---|
| MBP-NS3-F | SEQ ID NO: 12<br>CAGACTAATGCCGGATCCCATATGGCTGGAGTATTGTGGGATGTC |
| MBP-NS3-R | SEQ ID NO: 13<br>GTCGTGAAACAGTACGTGATCTTAAGGGTCACTTTCGAAAAATATCATCTTCGATCTCTG |
| NLuc-NS2B-F | SEQ ID NO: 14<br>GATATACCATGGGCAGCAGCCATCATCATCATCATCACGAAGACGCCAAAAACATAAAG |
| NS3_F | SEQ ID NO: 15<br>ccatatggctagcGCTGGAGTATTGTGGGATGTCC |
| NS3_R | SEQ ID NO: 16<br>gctcgaattcggatccCTATCCCTTTCGAAAAATATCATCTTC |
| NLuc-NS2B-R | SEQ ID NO: 17<br>CGGCGCTAGCCATATGGCTGCCGCGCGGCACCAGGCCGCTTCCATCCTTGTCAATCAAGG |
| NLuc-E66stop-F | SEQ ID NO: 18<br>GTCAAATGGGAAGATCAGGCATAAATATCAGGAAGCAGTCCAATC |
| NLuc-E66stop-R | SEQ ID NO: 19<br>GATTGGACTGCTTCCTGATATTTATGCCTGATCTTCCCATTTGAC |
| NS2B-NLuc-F | SEQ ID NO: 20<br>GGTGGTAGCGGCGGCGGTGGGGAAGACGCCAAAAACATAAAG |
| NS2B-NLuc-R | SEQ ID NO: 21<br>GTCGACGGAGCTCGAATTCTCATCCATCCTTGTCAATCAAGGCG |
| E66stop-NLuc-F | SEQ ID NO: 22<br>CGCCGATGTCAAATGGGAAGGCGGTGGTAGCGGTGGTGAAGACGCCAAAAACATAAAG |
| E66stop-NLuc-R | SEQ ID NO: 23<br>GTCGACGGAGCTCGAATTCTCATCCATCCTTGTCAATCAAGGCG |
| Cluc398-F | SEQ ID NO: 24<br>GTTCTGTTCCAGGGTCCACTGGGATCCTCCGGTTATGTAAACAATCCGGAAG |
| Cluc398-R | SEQ ID NO: 25<br>GGGACATCCCACAATACTCCAGCCACGGCGATCTTTCCGCCCTTC |

TABLE 2-continued Primers used

| | |
|---|---|
| GCN-F | SEQ ID NO: 26<br>GAAGGGCGGAAAGATCGCCGTGGCTGGAGTATTG<br>TGGGATGTCCC |
| GCN-R | SEQ ID NO: 27<br>GTCACGATGCGGCCGCTCGAGTCACTTTCGAAAA<br>ATATCATCTTCGATCT |
| GNC-F | SEQ ID NO: 28<br>CAATCCAGAGATCGAAGATGATATTTTTTCCGGT<br>TATGTAAACAATCCGG |
| GNC-R | SEQ ID NO: 29<br>CCGGGAGCTGCATGTGTCAGAGG |

His-NS2B and His-MBP-NS3 of DENV2 were synthesized as follows. His-NS2B (aa 48-95) was constructed based on an in-house covalently-linked N-terminal His-NS2B-NS3 fusion protein cloned between NheI and EcoR1 sites of the pET28a vector (EMD Biosciences) by introducing a stop codon after Leu95 of the DENV2 NS2B. For cloning of the DENV2 MBP-NS3 protease, an overlapping PCR strategy was used. DNA fragment of NS3 was amplified with pairs of primers of CAGACTAATGCCGGATCC-CATATGGCTGGAGTATTGTGGGATGTC (forward) and GTCGTGAAACAGTACGTGATCTTAAGGGT-CACTTTCGAAAAATATCATCTTCGAT CTCTG (reverse). The PCR product representing the NS3 residues 1-185 was used as a mega primer for PCR with an in-house His-MBP-Bcl10 constructed in pDEST-His-MBP vector (Addgene). Addition of MBP tag greatly enhanced the solubility of NS3, allowing purification of soluble MBP-NS3 directly from cell lysate supernatant.

Details of the constructs for HTS assay were as follows: (1) The N-terminal fragment (aa 1-416) of firefly luciferase (Nluc) was first cloned into the His-NS2B construct between His-tag and NS2B by PCR mutagenesis approach with pair of primers GATATACCATGGGCAGCAGCCATCATCAT-CATCATCACGAAGACGCCAAAAACA TAAAG (forward) and CGGCGCTAGCCATATGGCTGCCG-CGCGGCACCAGGCCGCTTCCATCCTTGTCAATCAA-GG (reverse); (2) A stop codon was introduced after the NS2B residue Glu66; The construct was named s Nluc-NS2BE66. (3) The C-terminal fragment (aa 398-550) of firefly luciferase (CLuc398) was amplified using pair of primers GTTCTGTTCCAGGGTCCACTGG-GATCCTCCGGTTATGTAAACAATCCGGAAG (forward Cluc) and GGGACATCCCACAATACTCCAGC-CACGGCGATCTTTCCGCCCTTC (reverse, NS3 portion was italicized and Cluc portion was underlined); NS3 was amplified with pair of primers GAAGGGCGGAAA-GATCGCCGTGGCTGGAGTATTGTGGGATGTCCC (forward) and GTCACGATGCGGCCGCTCGAGT-CACTTTCGAAAAATATCATCTTCGATCT (reverse NS3); Then Cluc398 and NS3 fusion was amplified using above PCR products as template with primers forward Cluc and reverse NS3. The PCR product was then used as a mega primer for PCR with pGEX-6P-1 vector (GE HealthCare) as a template to generate GST-Cluc398-NS3, named as GCN.

Figure 2B:
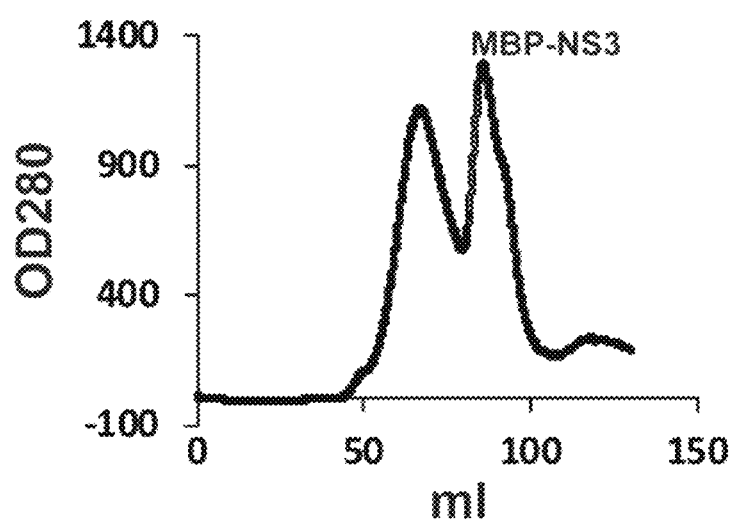
FIG. 2B and FIG. 2C show gel filtration profiles for purification of MBP-NS3 and HIS-NS2B proteins, respectively, using a 16/60 Superdex S200 column with an AKTA purifier.
Figure 2C:
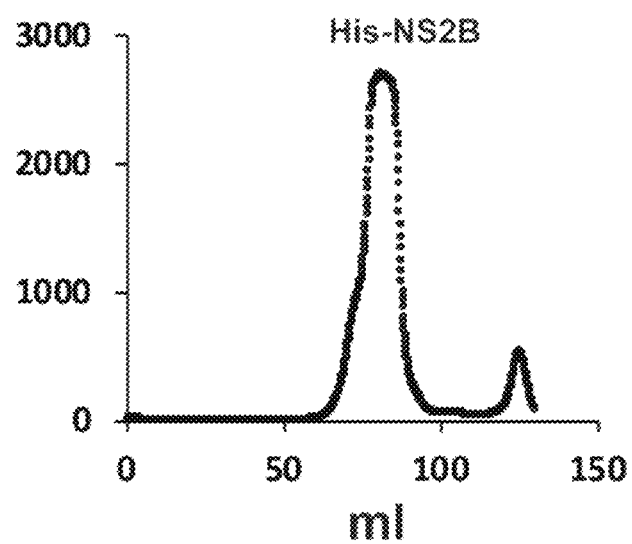

All proteins were expressed in *Escherichia coli* strain Rosetta 2(DE3) (EMD Biosciences) and purified through a nickel-nitrilotriacetic acid column (Qiagen), followed by a gel filtration 16/60 Superdex 200 column (GE HealthCare). FIG. 2A shows SDS-PAGE analysis of purified His-MBP-NS3 (lane 2) and His-NS2B (Lane 3). Lane 1 shows Bio-Rad broad range molecular weight (MW) standard. FIGS. 2B and 2C show gel filtration profiles for purification of MBS-NS3 and His-NS2B, respectively, using a 16/60 Superdex S200 column with an AKTA purifier.

Figure 3A:
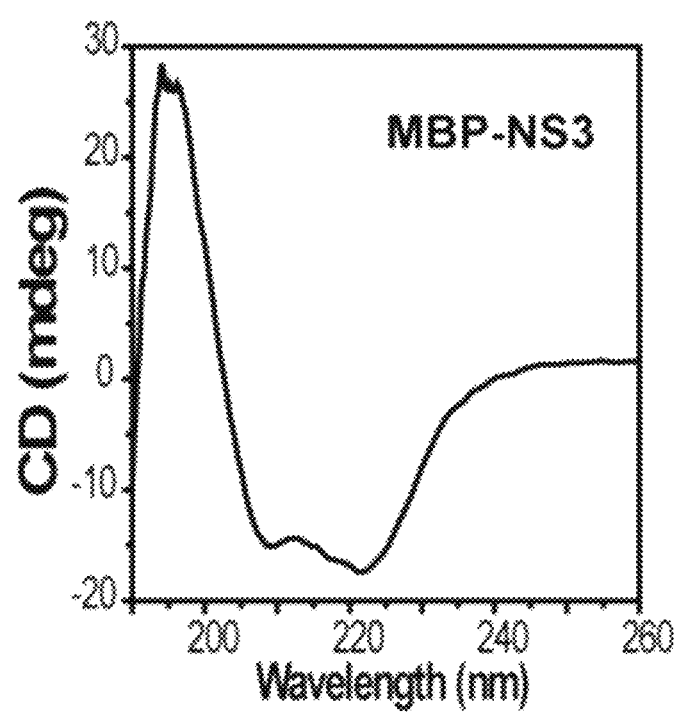
FIG. 3A is a plot of a circular dichroism analysis of purified His-MBP-NS3.
Figure 3B:
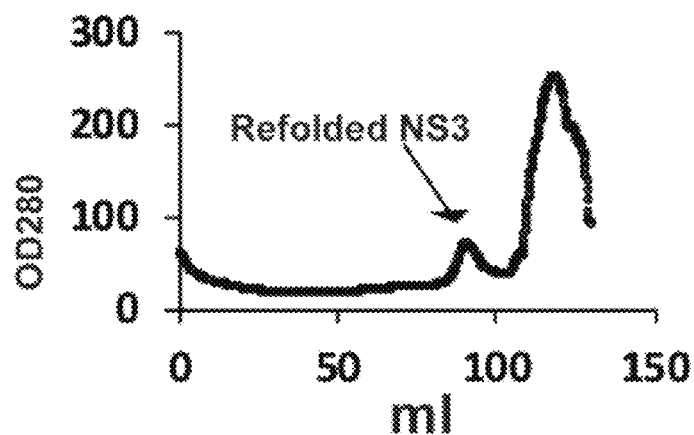
FIG. 3B shows a gel filtration profile for purification of refolded His-NS3 using a 16/60 Superdex S200 column with an AKTA purifier.
Figure 3C:
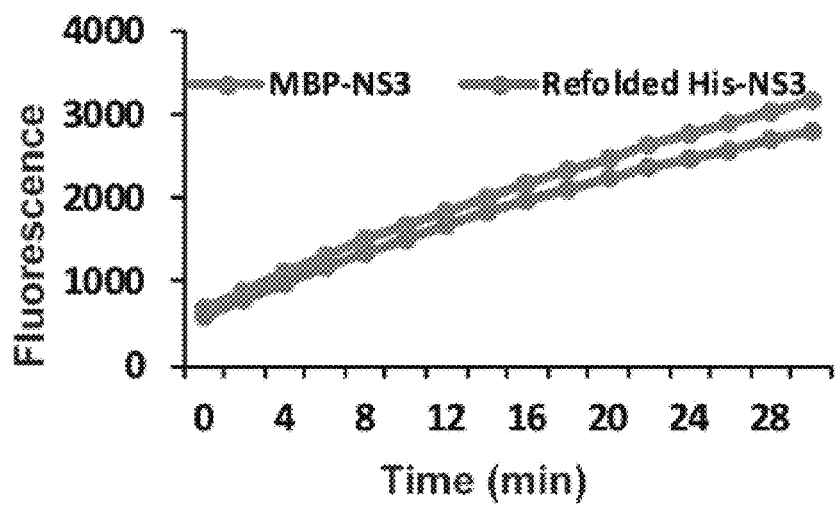
FIG. 3C shows transactivation of MBP-NS3 and refolded His-NS2B.
Figure 4:
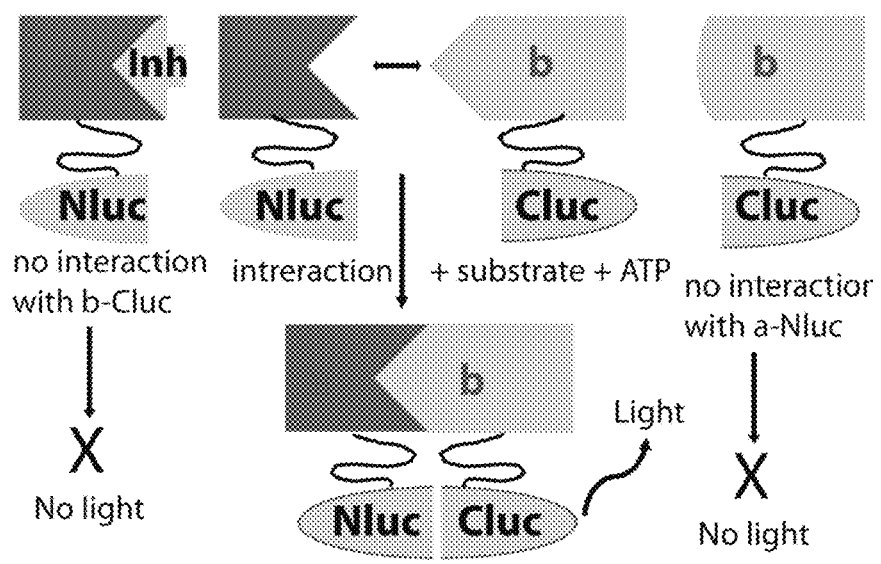
FIG. 4 is a diagrammatic representation of a split luciferase complementation (SLC)-based high throughput screening (HTS) assay to identify orthosteric inhibitors abolishing the interactions between flaviviral protease components NS2B and NS3 in accordance with the present disclosure.

Circular dichroism (CD) spectra of the His-MBP-NS3 at 1 mg/ml in PBS buffer were measured on a J-720 Jasco spectropolarimeter (Japan Spectroscopic Co.) equipped with a temperature-controlled cell holder. Static measurements were recorded at 20° C. For the far-UV (190-260 nm), CD spectra were measured at a bandwidth of 1 nm using a quartz cell of path length 0.2 mm; and for the near-UV (250-350 nm) using a 1-cm quartz cell. Data from four scans were averaged using the J-720 operating software. Far-UV CD spectra were smoothed by using the Jasco noise reduction routine. The extent of secondary structure of the MTases was calculated from the CD spectra in the far-UV spectral range, using the CDPro program suite. Sreerama & Woody (2000), Anal Biochem 287, 252-260. As shown in FIG. 3A, CD analysis indicated that the purified MBP-NS3 is correctly folded, displaying a typical CD spectrum of an αβ protein. FIG. 3B shows a gel filtration profile for purification of re-folded NS3, as described above. FIG. 3C shows transactivation of MBP-NS3 and refolded His-NS3, by His-NS2B. Both MBP-NS3 and His-NS3 were at 150 nM and NS2B was at 1 μM. The Abz substrate at 200 μM was used. Data were recorded using a Biotek Flx800 fluorescence reader. Both soluble MBP-NS3 fusion protein and refolded NS3 can be trans-activated by soluble His-NS2B, and have similar activities To explore whether orthosteric inhibitors abolishing the NS2B-NS3 interactions can inhibit the protease function, an SLC-based NS2B-NS3 interaction assay was developed. The principle of SLC and its application in identification of protein-protein interaction inhibitors is illustrated in FIG. 4. Firefly luciferase (FLuc) is composed of 550 amino acids (aa), which can be split into two fragments: the N-terminal fragment (NLuc) consisting of aa 1-416 and the C-terminal fragment (Cluc) composed of aa 398-550 for SLC assay of protein-protein interactions. Luker et al. (2004), Proc Natl Acad Sci USA 101, 12288-12293. Assuming a (FIG. 4, left) and b (FIG. 4, right) molecules are binding pairs, a-b interactions will bring the NLuc fused to a molecule and the CLuc fused to b molecule together to reconstitute a fully active FLuc. When luciferase substrate is added, the reconstituted FLuc will catalyze the reaction, generating light (FIG. 4, center). However, when non-interacting protein c fused to Cluc is mixed with a-NLuc, interaction will not occur; and SLC will not occur, leading to no light (FIG. 4, left and right). When the b-binding site on a molecule is occupied by a small molecule (e.g. Inh) (or b competitor), interaction will not occur between molecules a and b, resulting in inactive Luc fragments and no light.

Figure 5:
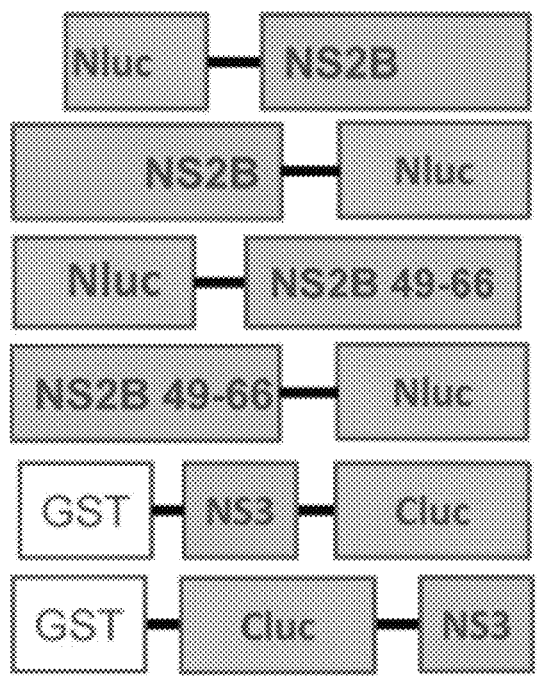
FIG. 5 is a diagrammatic representation of several fusion proteins used in an SLC HTS assay in accordance with the present disclosure.

As shown in FIG. 5, several fusion proteins were synthesized, including Nluc416 (aa 1-416 of FLuc)-NS2B (named as Nluc-NS2B) and GST-NS3-Cluc398 (aa 398-550 of FLuc) (named as GNC). As the positions of Fluc fragments were important, NS2B-NLuc and GST-Cluc-NS3 (GCN) were also synthesized. In addition, because NS2B aa 49-66 is enough to stabilize and bind NS328,29, Nluc-NS2B (49-66) (named as Nluc-E66stop) and NS2B (49-66)-Nluc (named as E66stop-Nluc) were synthesized.

An SLC assay using the 96-well plate on a Veritas microplate luminometer, as follows. GCN protein (200 nM final concentration) was dispensed into test buffer (lx Phosphate buffered saline (PBS), 0.05% Chaps, 0.1% BSA, 0.5% DMSO) with compounds at various concentrations from the NCGC pharmaceutical collection, and incubated for 30 min.

Then the Nluc-NS2BE66 was added to the mixture to a final concentration of 200 nM. The D-luciferin substrate dissolved in substrate buffer composing of 1×PBS, 2 mM MgCl$_2$, 4 mM EGTA, 4 mM ATP, 1 mM DTT was added to a final concentration of 5 μg/ml. The reaction mixture was incubated to 2 hours at room temperature and read using a ViewLux Plate Reader. Data were processed as reported according to standard protocols. Inglese et al. (2006), Proc Natl Acad Sci USA 103, 11473-11478.

Figure 6:
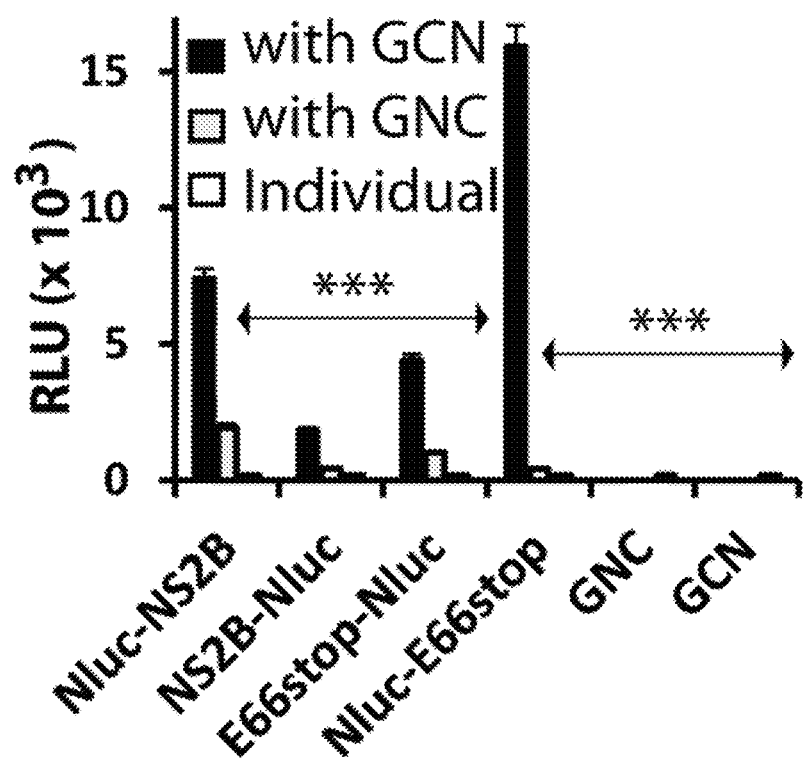
FIG. 6 is a graph depicting results of an SLC assay using various constructs illustrated in accordance with the present disclosure. (Unless otherwise indicated herein, levels of statistical significance are indicated in Figures as follows: *=p<0.05; =p<0.01; *=p<0.001.)
Figure 7:
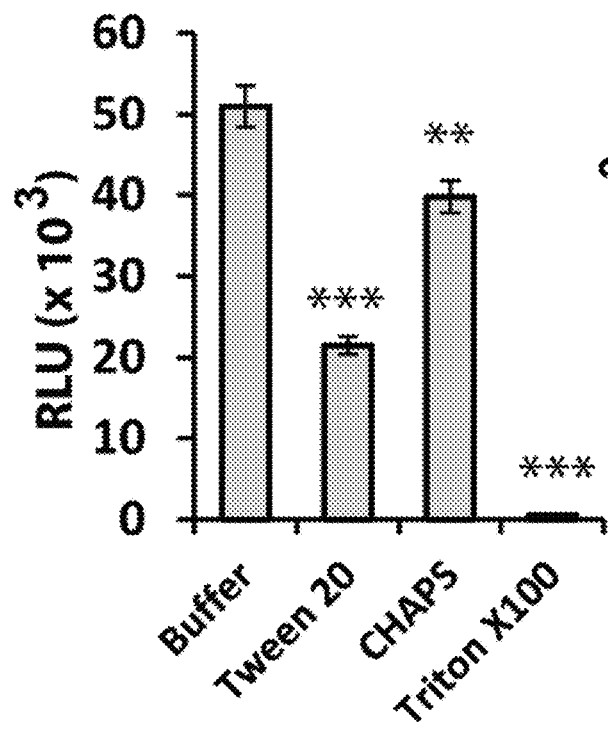
FIG. 7 is a graph depicting results of an SLC assay using an Nluc-E66stop/GCN construct pair in the presence of various detergents in accordance with the present disclosure.
Figure 8:
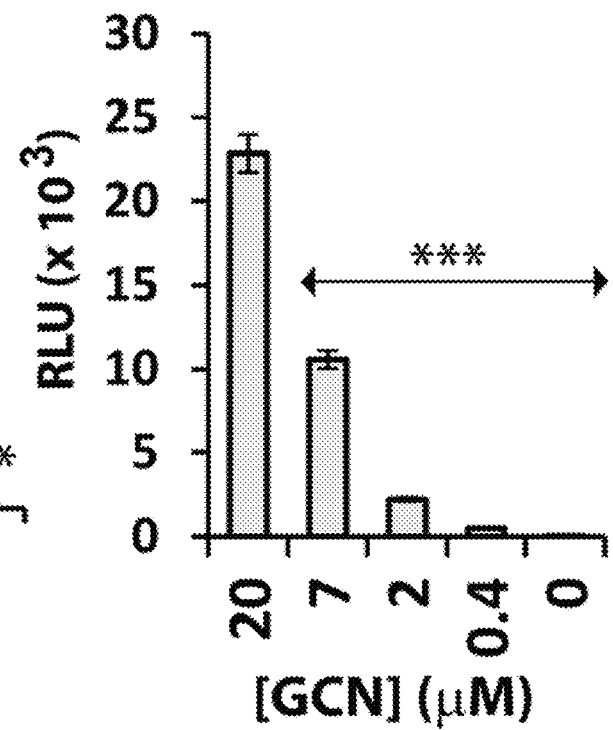
FIG. 8 is a graph depicting results of an SLC assay using an Nluc-E66stop/GCN construct pair with the GCN construct present at different doses in accordance with the present disclosure.

Individual construct did not give any luminescent light (RLU), as shown in FIG. 6. The positions of Fluc fragment indeed mattered. As shown in FIG. 6, the signals for GCN paired with NLuc fused with any NS2B fragment constructs (black) were much stronger than those for GNC counter pairs (grey). Among these pairs, Nluc-E66stop/GCN gave the strongest signal. These results are consistent with the fact that the N-terminal portion of NS2B (aa 49-66) is sufficient to bind and stabilize NS3. Because the Nluc-E66stop/GCN pair gave the best SLC signal, this pair was chosen to perform all later experiments. Assay conditions were optimized by varying detergent. As shown in FIG. 8, CHAPS is compatible with the SLC assay whereas Triton X100 is not. Under these optimized condition, SLC signal was dose dependent, as shown in FIG. 8.

Figure 9:
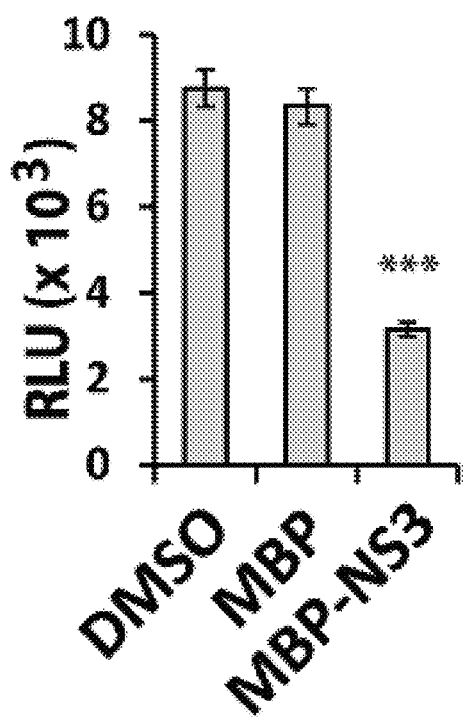
FIG. 9 is a graph showing results from a control experiment indicating that the presence of the C-terminal of luciferase is necessary for SLC signal in the HTS assay.
Figure 10:
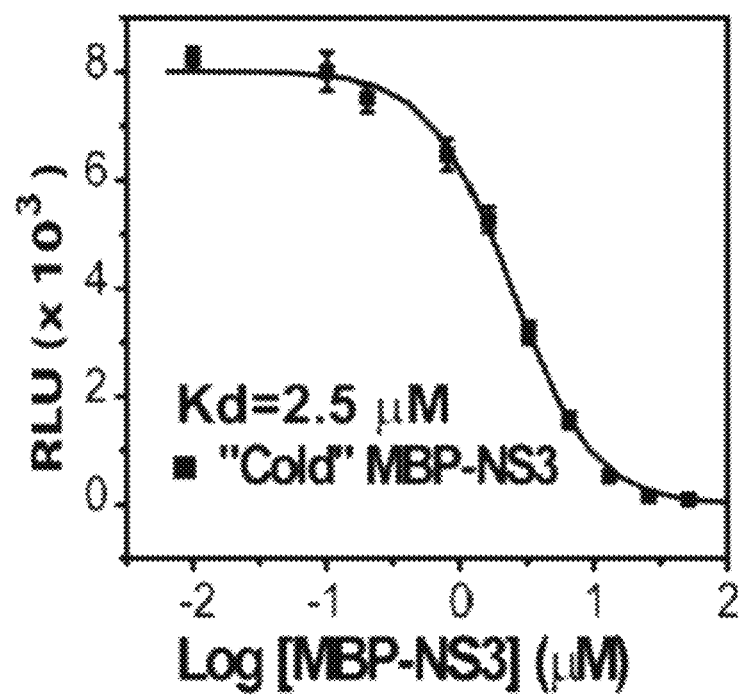
FIG. 10 is a graph showing dose response inhibition of the SLC signals by peptide pairing lacking the C-terminal of luciferase.
Figure 11:
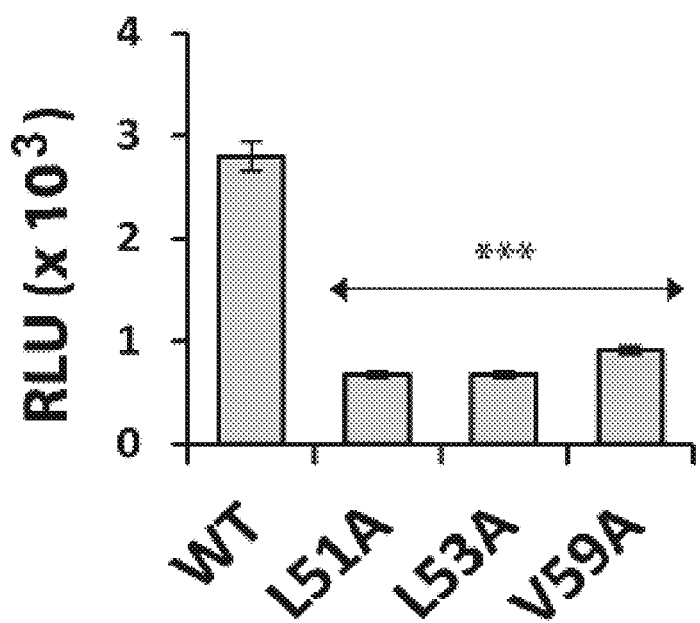
FIG. 11 is a graph from a control experiment showing that NS2B mutations greatly reduced SLC signal.

Specificity of the HTS assay was determined by using "cold" MB-NS3 (e.g. MBP-NS3 alone not fused with Cluc) as a competitor to compete GCN in an SLC-based NS2B-NS3 interaction assay. As shown in FIG. 9, "cold" MBP-NS3 greatly reduced the SLC signals from the Nluc-E66stop/GCN interactions, whereas MBP fusion tag did not have any inhibition, indicating the specificity of the assay to requiring the complete complement of luciferase peptide. As shown in FIG. 10, dose response inhibition of the SLC signals from Nluc-E66stop and GCN (80 nM each) by "cold" MBP-NS3 varied from 52 to 0.1 μM. The reaction was dose-dependent with affinity determined as 2.5 μM for the MBP-NS3 and Nluc-E66stop NS2B interactions. To test whether NS2B mutations reduced SLC, GCN was paired with equal molar of Nluc-E66stop or Nluc-E66stop mutants (L53A and V59A). Mutations of NS2B residues L51, L53 and V59 of the Nluc E66stop construct significantly reduced the SLC as shown in FIG. 11. These residues were known to be essential for the protease function. Chappell et al. (2008), J Gen Virol 89, 1010-101. Overall these results indicated that the SLC signal from Nluc-E66stop/GCN pair is specific to the interactions between NS2B and NS3.

Figure 12:
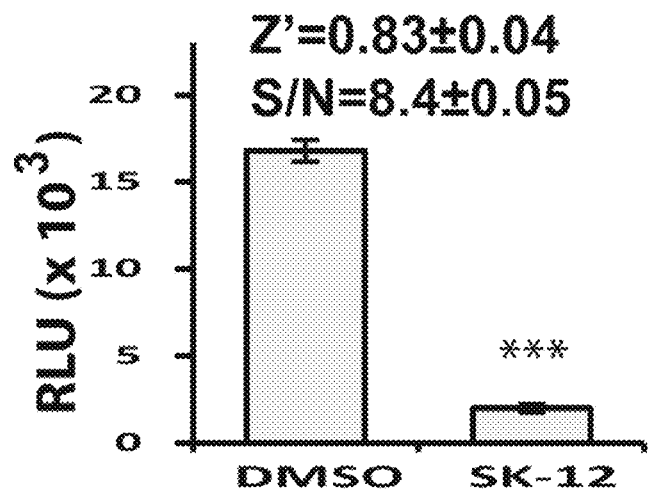
FIG. 12 is a graph demonstrating effectiveness of an SLC HTS assay using a positive control known to block NS2B-NS3 interactions.
Figure 13:
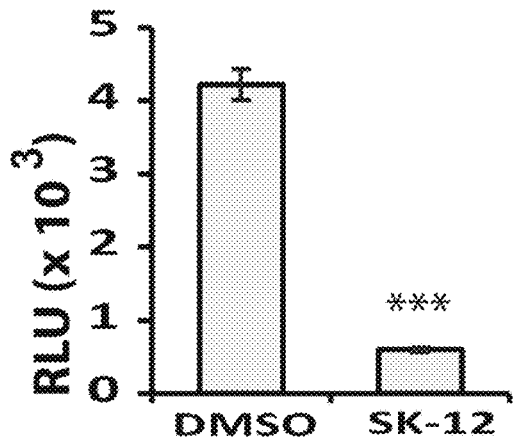
FIG. 13 is a graph demonstrating the sensitivity of the SLC assay disclosed herein when NS2B and NS3 are co-expressed in cells in vitro and treated with a positive control inhibitor of NS2B-NS3 interactions.

It was previously reported that a small molecule SK-12 is an orthosteric inhibitor blocking NS2B-NS3 interactions. Pambudi et al. (2013), Biochem Biophys Res Commun 440, 393-398. Using SK-12 as a control, SK-12 at 40 μM concentration significantly inhibited SLC of Nluc-E66-stop/GCN, as shown in FIG. 12. Nluc-E66stop and GCN at 100 nM were used with DMSO or SK-12 (40 μM). n=8. An SLC assay performed in accordance with the present disclosure is very robust, with signal/noise (S/N) ratios (DMSO vs SK-12) being 8.4 folds at a very low concentration of 100 nM for each component and a Z' score of 0.83 that is better than the gold standard (Z' score of 0.5) for an HTS assay. Furthermore, as shown in FIG. 13, when Nluc-E66stop and GCN were co-expressed in *E. coli* cells, addition of Sk-12 significantly suppressed the SLC signal. Plasmids of Nluc-E66stop and GCN were co-transformed into *E. coli* BL21 (DE3). Cells were grow to OD$_{600}$ of 0.6 and were induced by IPTG. Cells were continuously grew for 2 hours, collected and resuspended in luciferase assay buffer. 100 μl of cells were dispensed into 96-well plate, incubated with 1% DMSO or Sk-12 (40 μM) for 2 hours, then mixed with substrate luciferin. N=3. These data demonstrate that an SLC assay as disclosed herein can be used as an HTS assay to screen inhibitors for NS2B-NS3 interactions.

Figure 14:
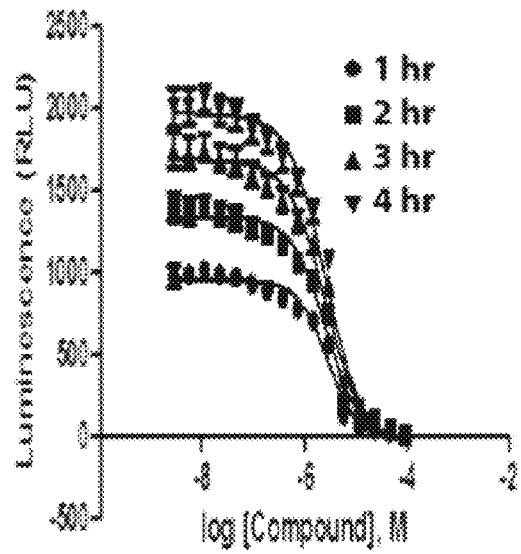
FIG. 14 is a graph showing a dose response inhibition of the SLC signals from Nluc-E66stop and GCN by a positive control inhibitor in 1,536-well format.

An SLC assay was successfully transferred from a 96-well plate format to a 1,536-well format, with a total volume of 10 μl and was very robust. IC$_{50}$ values calculated using data collected at 1, 2, 3, and 4 hours post sample mixings were constant (as shown in FIG. 14), and Z' score was about 0.78. Overall these data established that an SLC screen performed in accordance with the present disclosure is an effective screen for inhibitors of interaction between NS2B-NS3 proteins.

An SLC HTS screen a was subsequently performed, in accordance with the present disclosure, against the NIH Chemical Genomics Center (NCGC) Pharmaceutical Collection (NPC library), which harbors about 2,800 clinically-used (and in clinical trials) drugs, using a quantitative HTS (qHTS) platform. Inglese et al. (2006), Proc Natl Acad Sci USA 103, 11473-11478; Bi et al. (2015), Anal Bioanal Chem 407, 5343-5351. A qHTS approach was chosen because it has been shown to greatly reduce not only false positives but also false negatives, compared to screening libraries at one fixed concentration. An additional benefit of a qHTS approach is that compound potencies and efficacies (IC50 or EC50) may be immediately available after the primary screen.

Figure 15:
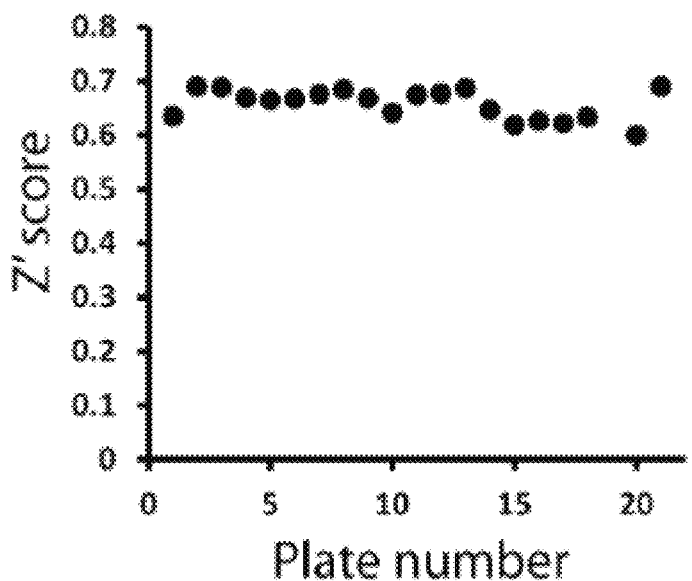
FIG. 15 is a graph of Z' score distribution for all plates used in an SLC HTS.

Compounds were prepared at 8 different concentrations (5-fold dilution) in 8 different plates (i.e., one plate, one concentration for each compound). The final concentration of the compounds in the 10-μL assay volume ranged from 0.3 nM to 23 μM. During a primary screen, control inhibitor was used as a positive control and was tested in each plate to evaluate the plate-to-plate consistency. A total of 20 plates were used for 2,800 compounds. A pilot HTS assay displayed high quality with a Z' score averaged 0.7 (between plates), as shown in FIG. 15, and an S/N ratio of 8.1. Concentration-response curves for control inhibitor were consistent from plate t0 plate.

Upon completion of screening, automated data normalization and curve fitting were performed by using the NCATS in-house software package. 124 compounds were found to have IC$_{50}$ less than 20 μM. Selected active compounds were re-tested in 11 point titrations with concentration ranging from 390 μM to 23 μM (3-fold dilution) in an SLC assay using in accordance with the above disclosure except that 11 point titrations were within one 1,536-well plate. Twenty-three compounds were confirmed to have IC$_{50}$ less than 15 μM and three less than 1 μM.

Figure 16:
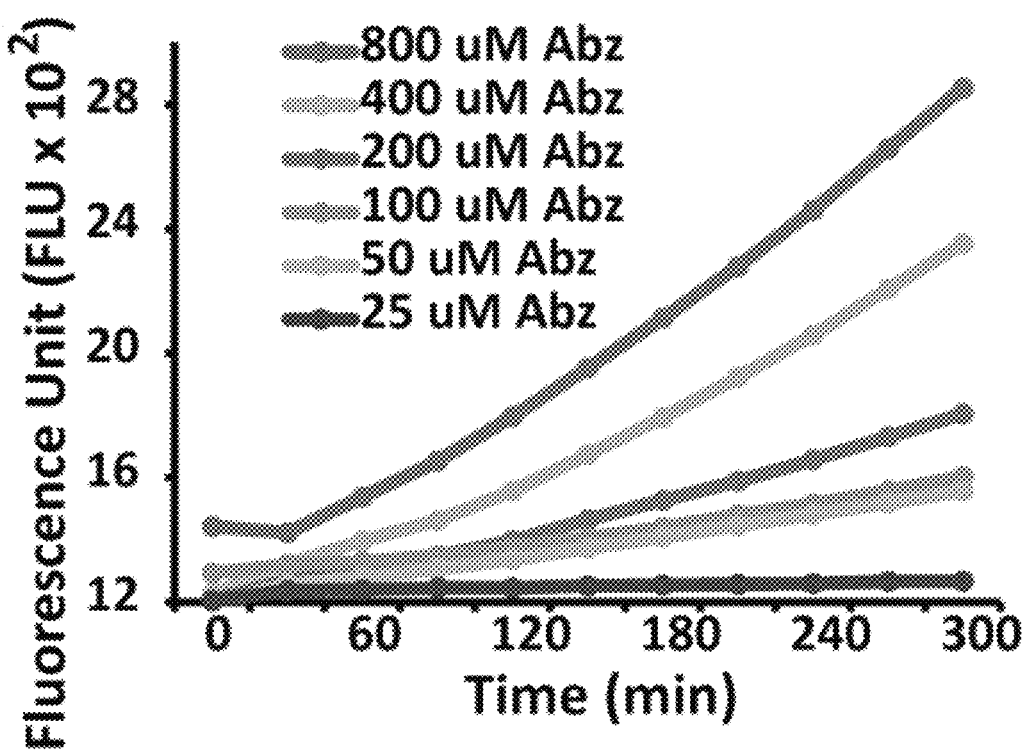
FIG. 16 is a graph depicting results of an NS2B/NS3 protease assay at different doses of fluorophore blue-shifted o-Aminobenzoic acid (Abz) in accordance with the present disclosure.
Figure 17:
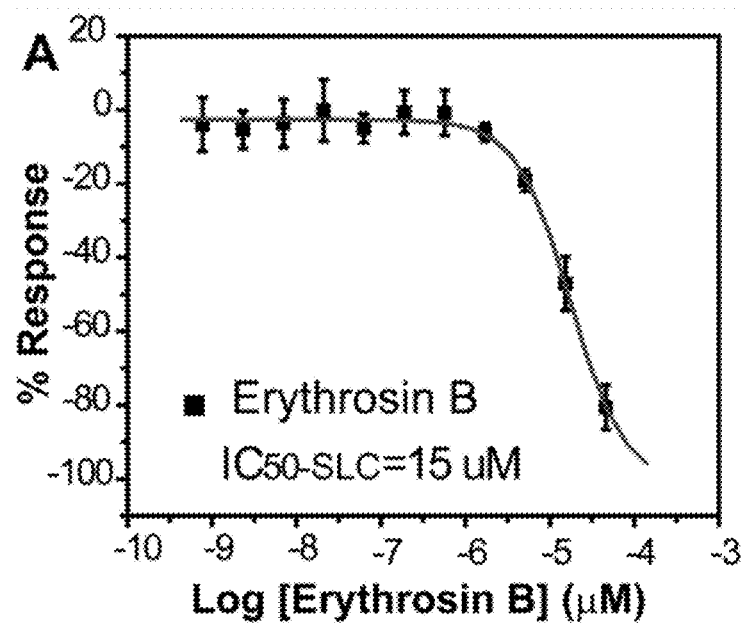
FIG. 17 is a graph illustrating dose-dependent inhibition of SLC upon binding of NLuc-NS2B$_{49-66}$ to GST-CLuc-NS3 by erythrosin B.
Figure 18:
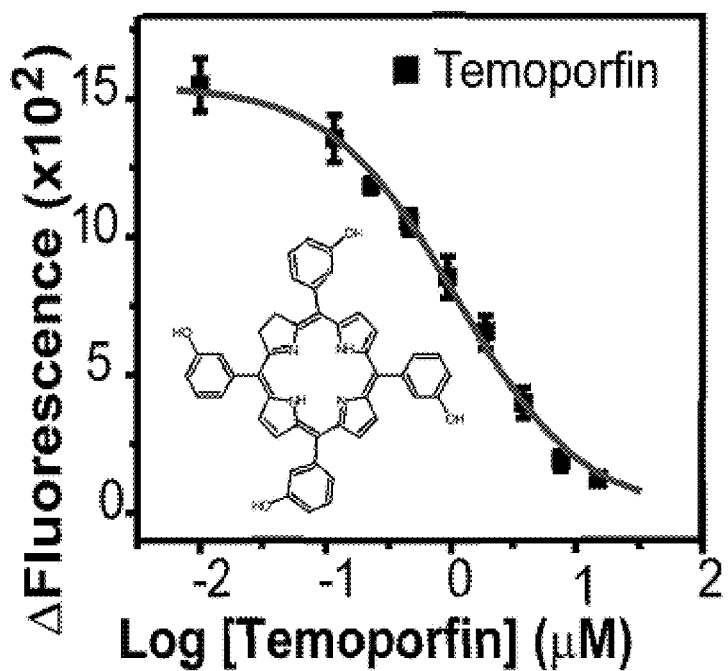
FIG. 18 is a graph showing an $IC_{50}$ curve fitting of temoporfin's anti-NS2B/NS3 protease activity in accordance with the present disclosure.
Figure 19:
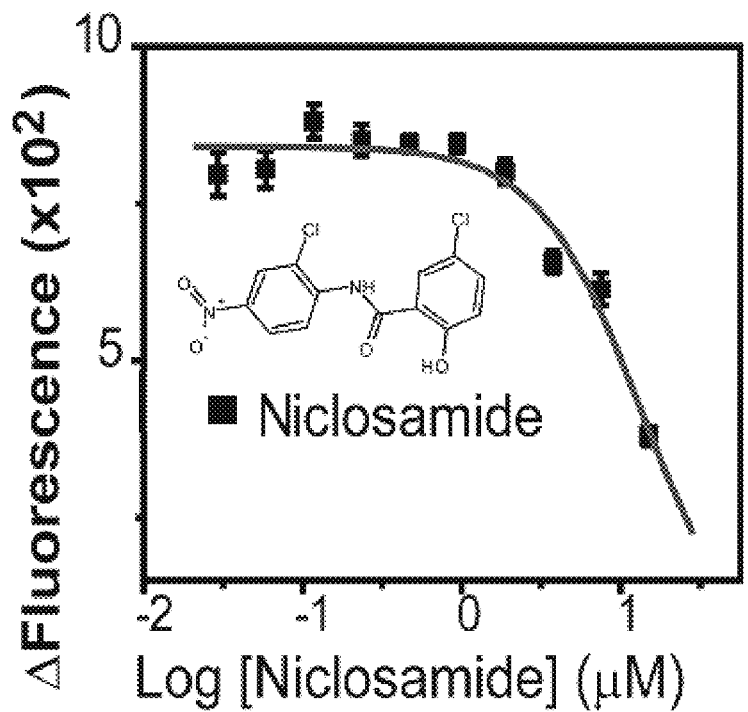
FIG. 19 is a graph showing an $IC_{50}$ curve fitting of niclosamide's anti-NS2B/NS3 protease activity in accordance with the present disclosure.
Figure 20:
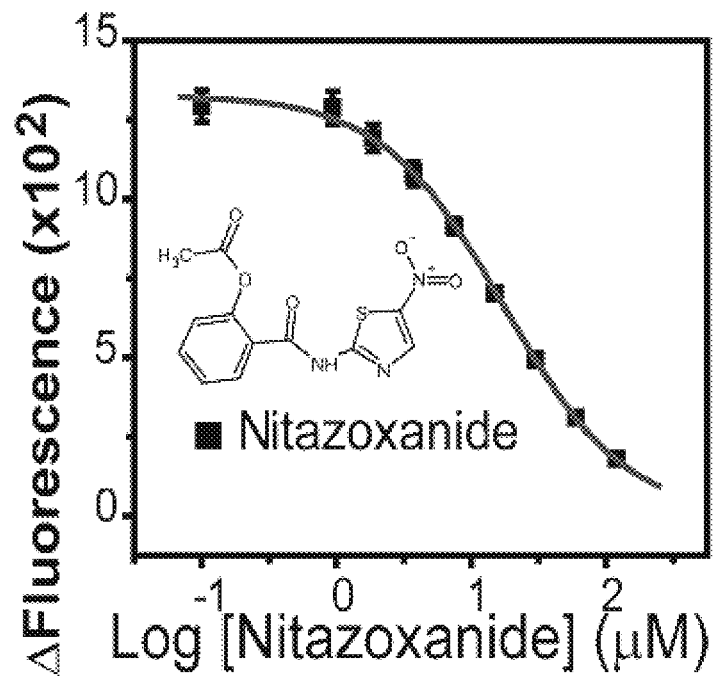
FIG. 20 is a graph showing an $IC_{50}$ curve fitting of nitazoxanide's anti-NS2B/NS3 protease activity in accordance with the present disclosure.
Figure 21:
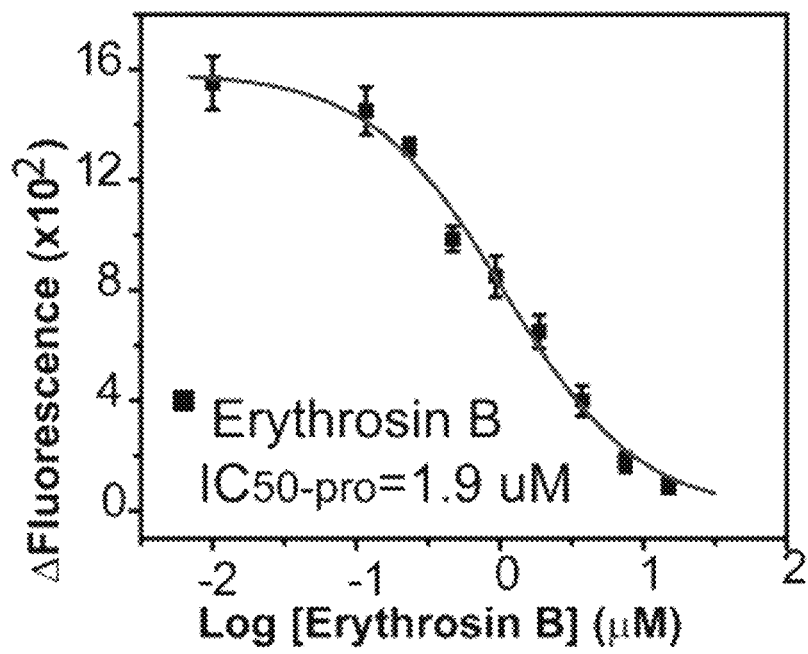
FIG. 21 is a graph showing dose-response inhibition of His-NS2B/His-MBP-NS3 protease activities by erythrosin B.
Figure 22:
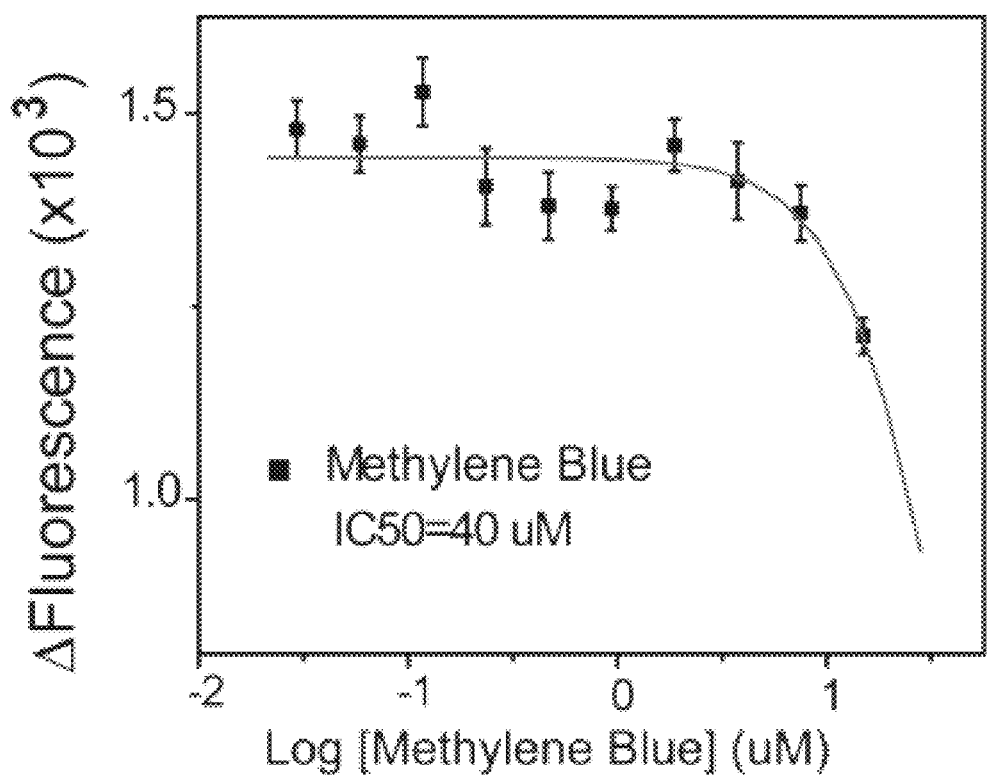
FIG. 22 is a graph showing dose-response inhibitions of the DENV2 His-NS2B/His-MBP-NS3 protease activities by methylene blue.

A protease inhibition assay was also used to confirm anti-protease activity of compounds identified as having high anti-NS2B-NS3-interaction activity. DENV2 NS3-MBP fusion protein (50 nM) was mixed with candidate compounds (at various concentrations, or DMSO control) in reaction buffer (20 mM Tris pH 8.0, 100 mM NaCl, 5% Glycerol, and 0.05% CHAPS) and incubated at 40 C for 30 minutes. Then the DENV2 His-NS2B was added at 1 μM final concentration. To overcome interference caused by compound auto-fluorescence, two sets of substrates were prepared: blue-shifted o-Aminobenzoic acid (Abz)-RRRR-↓SAG-3-nitrotyrosine (ex/em: 320/420 nm), and red-shifted 5-Carboxytetramethylrhodamine (TAMRA)-RRRRL-↓SAG-QXL570 substrates (ex/em: 540/570 nm), in which nitrotyrosine and QXL570 are the quenchers of fluorophores Abz and TAMRA, respectively. Peptide substrate was added to the mixture at a concentration 50 μM or 10 μM, respectively, and substrate cleavage was monitored over time at 37° C. in a BioTek Flx800 at excitation/emission wavelengths of 360 nm/420 nm (Abz substrate) or 520 nm/575 nm (TAMRA substrate). The rate of increase in RFU over time was calculated in the linear range and normalized as a percent of the DMSO control. As shown in FIG. 16, protease digestion releases fluorophore from its quencher, leading to fluorescence increase. Using this assay, erythrosin B moderately inhibited the interactions between $NS2B_{49-66}$ and NS3 with $IC_{50-SLC}$ of 15 µM ($IC_{50}$, compound concentration required to inhibit enzymatic activity by 50%). FIG. 17 shows dose-dependent inhibition of SLC upon binding of NLuc-$NS2B_{49-66}$ to GST-CLuc-NS3 by erythrosin B.

Using this assay, compounds identified as inhibiting NS2B-NS3 interaction in accordance with the SLC HTS assay as disclosed herein were tested for activity as flavivirus protease inhibitors. Several were confirmed to inhibit His-NS2B/His-MBP-NS3 hetero protease complex activity with $IC_{50}$ values ranging from 0.76 M to 41.6 µM, as shown in Table 1. FIGS. 18-22 show $IC_{50}$ curve fittings of protease inhibitory experimental data for temoporfin, niclosamide, nitazoxanide, erythrosine B, and methylene blue, respectively.

Figure 23A:
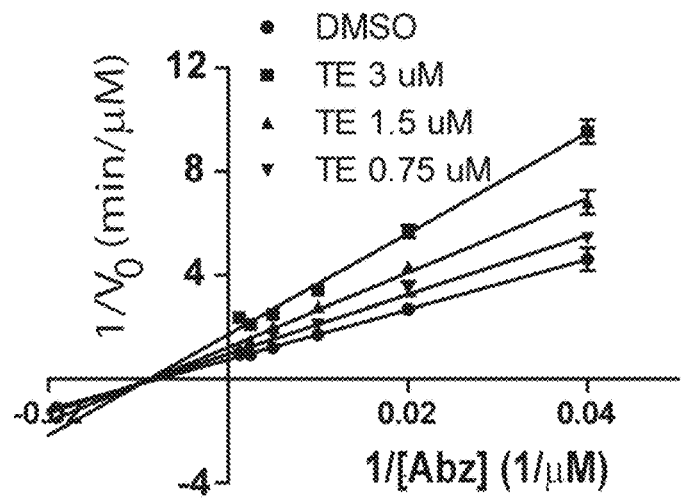
FIG. 23A, FIG. 23B, FIG. 23C, and FIG. 23D are Lineweaver-Burk plots of kinetics data for temoporfin's, niclosamide's, nitazoxanide's, and erythrosin B's anti-NS2B/NS3 protease activity, respectively, in accordance with the present disclosure.
Figure 23B:
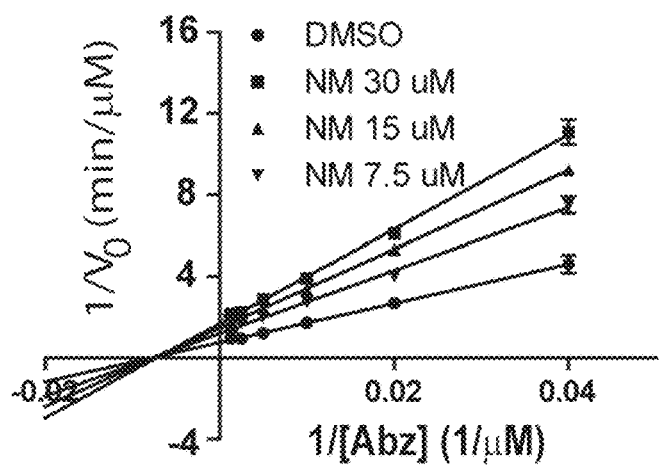
Figure 23C:
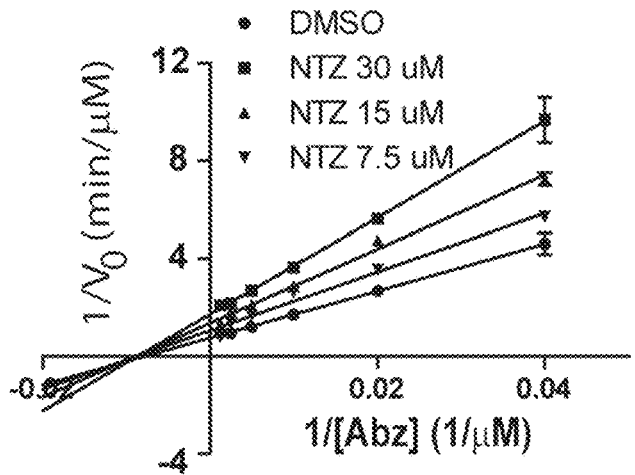
Figure 23D:
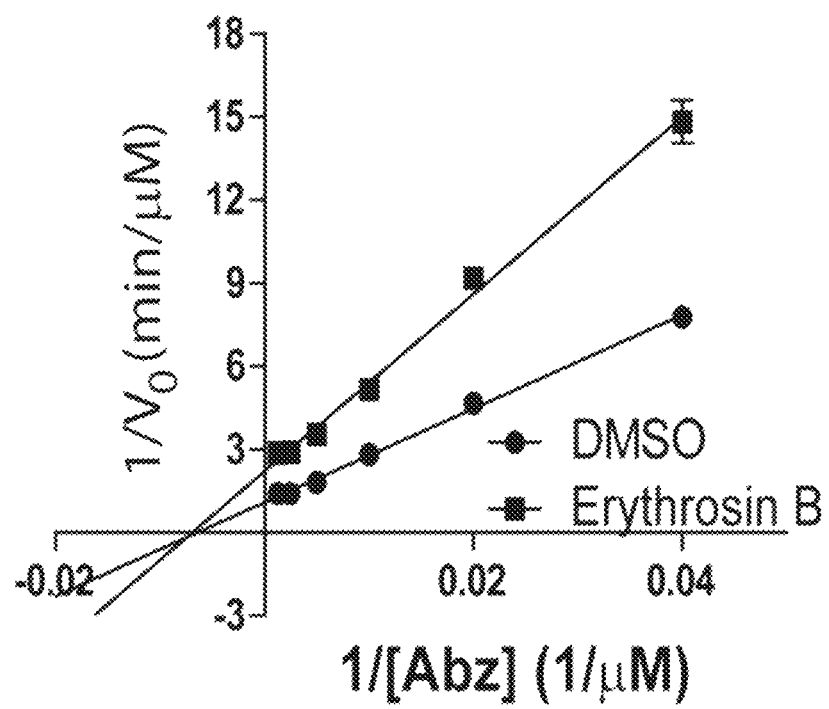
Figure 24A:
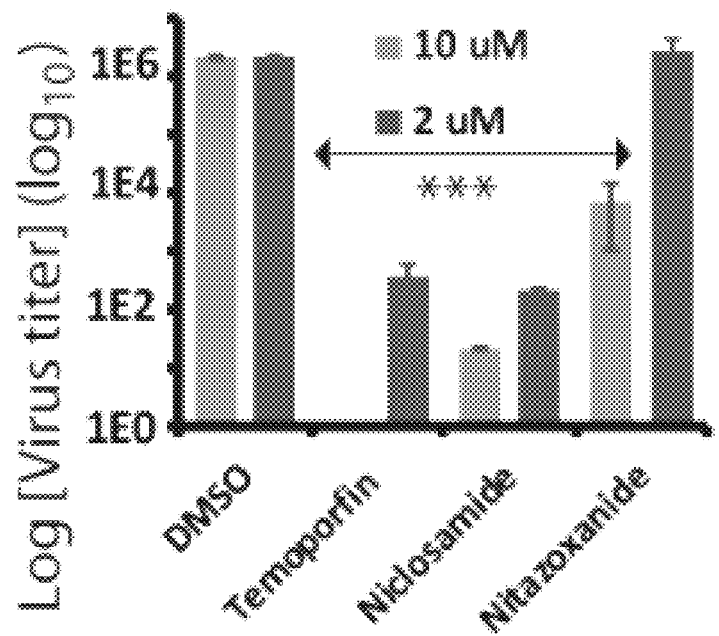
FIG. 24A is a graph showing inhibition of DENV2 in viral reduction assay in A549 cells by temoporfin (TE), niclosamide (NM), and nitazoxanide (NTZ) at 10 µM and 2 µM concentrationsin accordance with the present disclosure.
Figure 24B:
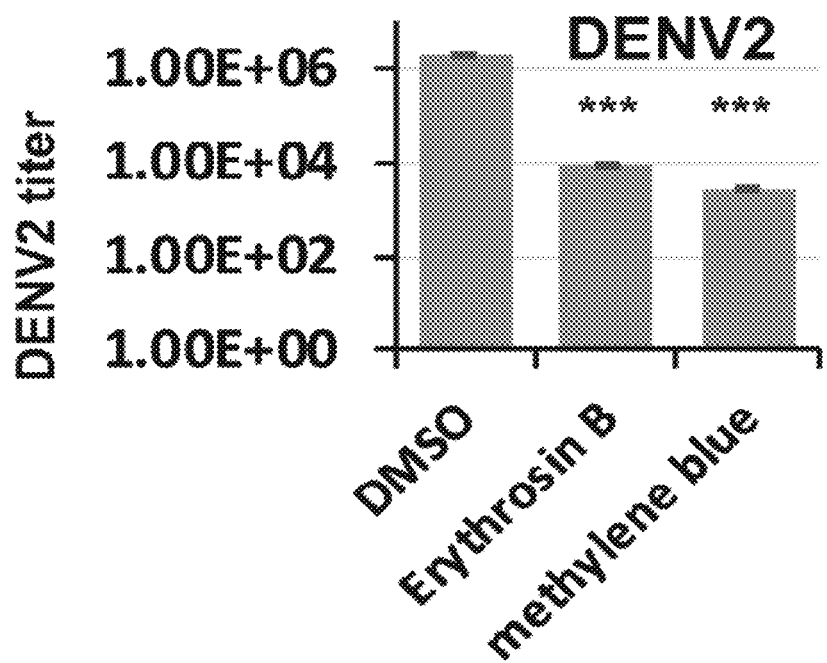
FIG. 24B is a graph showing inhibition of DENV2 in viral reduction assay in A549 cells by erythrosin B (10 uM) and methylene blue (2 uM) in accordance with the present disclosure.

To determine whether compounds inhibited the Dengue virus NS2B/NS3 protease by means of an orthosteric mechanism, enzymatic activity of NS2B-NS3 protease in the presence or absence of inhibitory compounds with varying concentrations of the Abz substrate were measured. Lineweaver-Burk plot of kinetics experimental data for temoporfin (FIG. 23A), niclosamide (FIG. 23B), nitazoxanide (FIG. 23C), and erythrosin B (FIG. 23D) inhibition of the His-NS2B/His-MBP-NS3 hetero protease complex. When compound temoporfin was present at 1.5 µM concentration, the $V_{max}$ of the His-NS2B/MBP-NS3 hetero protease complex composed of 50 nM MBP-NS3 and 1 µM His-NS2B was significantly reduced to 57% of the DMSO control. Conversely, the Km of the DMSO control was similar to the Km of the temoporfin inhibited sample. The $V_{max}$ values for the DENV2 His-NS2B/MBP-NS3 heterocomplex were significantly reduced in the presence of these drugs at various concentrations, compared to that of the DMSO control. Conversely, the $K_m$ values did not change. The lowered $V_{max}$ but similar $K_m$ values of the His-NS2B/MBP-NS3 heterocomplex indicate non-competitive inhibition according to classical Michaelis-Menten enzyme kinetics. These results are consistent with the proposed mechanism, which posits that these compounds do not compete with the protein substrate at the active site, but instead inhibit protease activity by orthosterically abolishing the binding of NS2B to NS3. These results indicate that compounds shown to inhibit flaviviral NS2B/NS3 protease activity may do so at least partly because of their inhibitory effect on NS2B/NS3 binding as demonstrated an SLC HTS screen in accordance with the present disclosure.

To determine if compounds were effective against the replication of actual flavivirus, A549 cells were infected with flavivirus in the presence of two different concentrations of each compound or a DMSO control, and the virus produced was tittered 48 hours post-infection. A viral titer reduction assay was used to determine the compounds' effect on selected flaviviruses, including DENV2, ZIKV (Puerto Rico strain PRVABC59), WNV, JEV, and YFV. Approximately $2\times10^5$ human A549 cells in 500 µl of media were seeded into each well of a 24 well plate. At 24-30 hours after seeding, dilutions at 2× the desired concentration of the compound were made in 2% DMSO media and 250 µl was added to wells in triplicate. Immediately following, 250 µl of media containing flavivirus at a concentration to yield a MOI 0.1 PFU/cell, was added to the wells. After 42 hours incubation at 37° C., culture media was collected, and stored at −80° C. for later quantification using a plaque assay. For the plaque assay, Vero cell monolayers in 6-well plates were seeded 3-4 days prior to infection to achieve a confluent monolayer. Depending on the virus, three to eight, 10-fold serial dilutions of the harvested samples were made, and three to five dilutions of the virus were tested. 100 µl of the dilution were inoculated into each of 2 wells, rocked gently to distribute virus, and incubated for 1 hour at 37° C. Cells were then overlaid with a nutrient medium containing 0.6% oxoid agar. The agar was allowed to solidify and the plates were then incubated at 37° C. A second overlay containing 2% neutral red was added after the plaques began to appear on day 2, and then incubated overnight. Plaques were counted daily for 1-3 days until no significant increase was seen.

Figure 25:
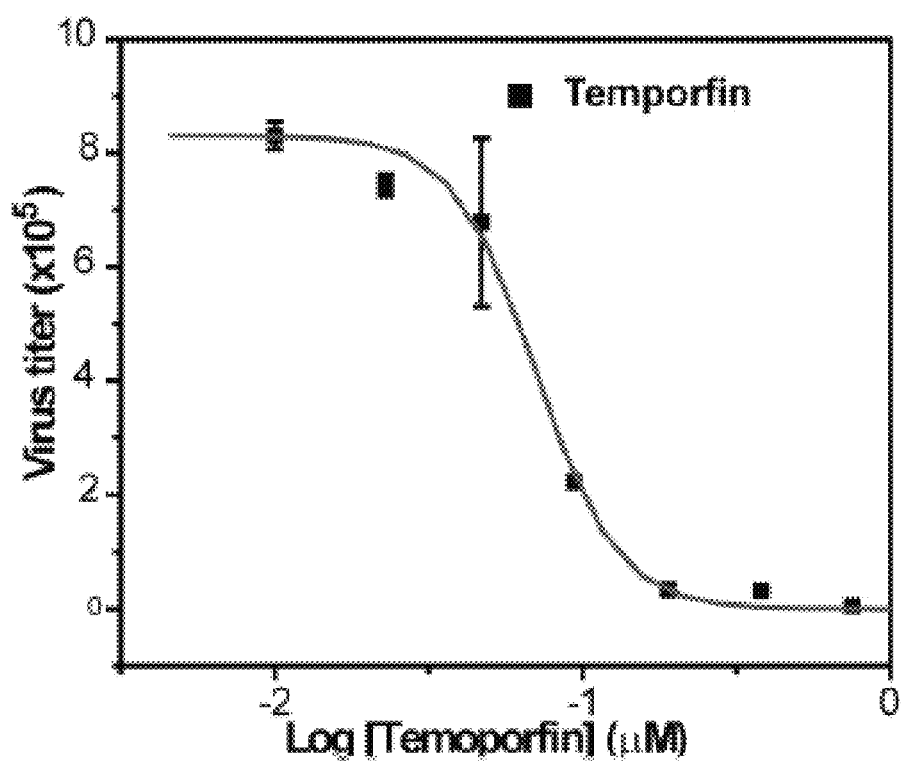
FIG. 25 is a graph showing dose-response inhibition of DENV2 in a viral reduction assay by temoporfin in accordance with the present disclosure.
Figure 26:
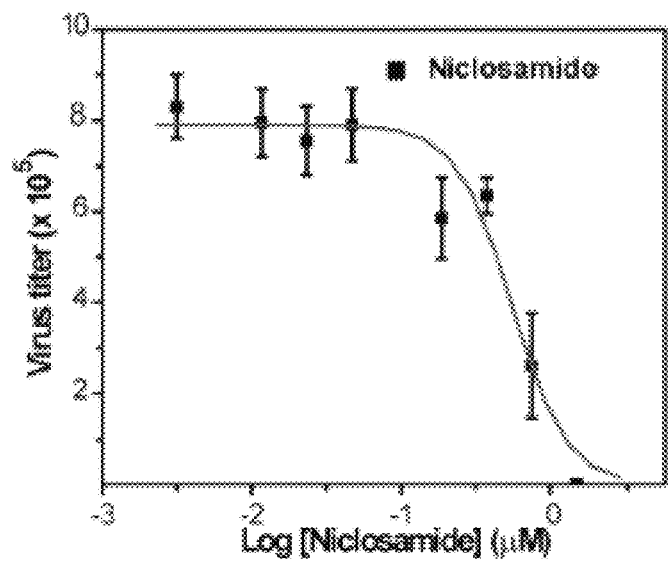
FIG. 26 is a graph showing dose-response inhibition of DENV2 in a viral reduction assay by niclosamide in accordance with the present disclosure.

The effective concentration $EC_{50}$ (the concentration of inhibitor required to reduce virus growth by 50%) was determined by nonlinear regression fitting of a dose-response curve using an ORIGIN software package. Viral production was significantly reduced in the presence of several compounds at concentrations of 2 µM and higher. Effects for inhibiting DENV2 are shown in FIGS. 24-27A and Tables 1 and 3. FIGS. 25 and 26 show dose response inhibition of DENV2 by temoporfin and niclosamide, respectively.

TABLE 3

Broad spectrum anti-flavivirus activities

| Compound | $IC_{50-pro}$ (µM) | $CC_{50}$ (µM) | Virus | $EC_{50}$ (µM) | $EC_{90}$ (µM) | TI[#] |
|---|---|---|---|---|---|---|
| temoporfin | 1.1 ± 0.1 | 40.7 ± 0.7 | ZIKV | 0.024 ± 0.003 | 0.13 | 1,696 |
| | | | ZIKV* | 0.022 ± 0.002 | 0.12 | 1,850 |
| | | | DENV2 | 0.020 ± 0.003 | 0.11 | 2,035 |
| | | | WNV* | 0.010 ± 0.001 | 0.030 | 4,070 |
| | | | JEV* | 0.011 ± 0.001 | 0.025 | 3,700 |
| | | | YFV* | 0.006 ± 0.001 | 0.015 | 6,783 |
| | | | SLEV* | 0.008 ± 0.001 | 0.025 | 5087 |
| | | | POWV* | 0.010 ± 0.001 | 0.032 | 4070 |
| niclosamide | 12.3 ± 0.6 | 4.8 ± 1.0 | ZIKV | 0.48 ± 0.06 | 1.9 | 10 |
| | | | DENV2 | 0.55 ± 0.05 | 2.3 | 9 |
| | | | WNV | 0.54 ± 0.17 | 2.3 | 9 |
| | | | JEV | 1.02 ± 0.08 | 2.4 | 3.8 |
| | | | YFV | 0.84 ± 0.02 | 1.9 | 5.7 |
| nitazoxanide | 15.9 ± 0.9 | 77 ± 7.2 | ZIKV | 1.48 ± 0.18 | 4.0 | 52 |
| | | 60[1] | JEV | 0.39 | | 154 |

TABLE 3-continued

Broad spectrum anti-flavivirus activities

| Compound | $IC_{50\text{-}pro}$* (µM) | $CC_{50}$* (µM) | Virus | $EC_{50}$* (µM) | $EC_{90}$* (µM) | TI# |
|---|---|---|---|---|---|---|
| Erythrosin B | 1.9 ± 0.6 | >100 | ZIKV | 0.62 ± 0.09 | 2.0 | 161 |
| Methylene blue | 40 | 1.9 | ZIKV* | 0.28 | | 6.8 |
| | | | WNV | 0.1 | | 19 |

*Experiment was performed without ambient light (in dark).
*IC50, compound concentration required to inhibit 50% of a reaction or binding; CC50: the concentration of compound at which 50% cells are viable; EC50 and EC90: the effective concentration of a drug at which virus production is reduced by 50% or 90%, respectively.
TI: Therapeutic index defined as CC50/EC50.

Figure 27A:
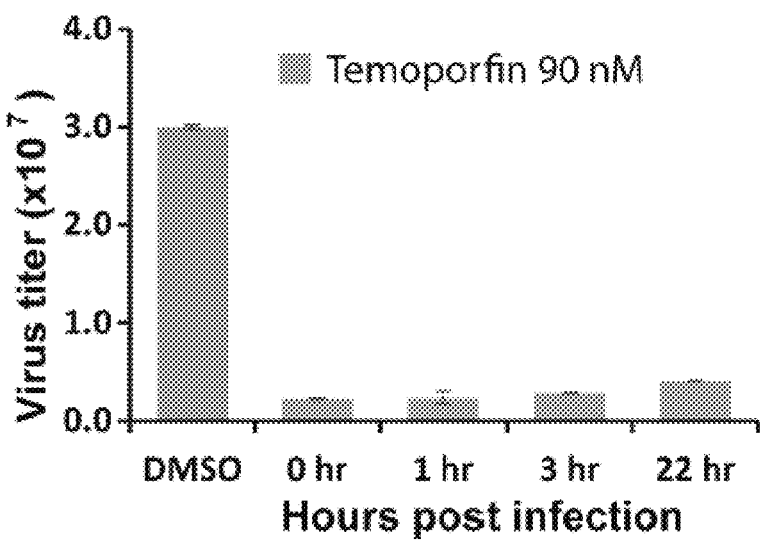
FIG. 27A is a graph showing inhibition of DENV2 in a viral reduction assay by temoporfin administered at different time points postinfection in accordance with the present disclosure.

A time-of-addition experiment was performed to characterize the mode of action of inhibition for temoporfin performed similarly to an antiviral assay disclosed above. A549 cells were infected with ZIKV. Temoporfin (90 nM) (~$EC_{80}$) was added to infected cells at various time points post infection without exposure to ambient light, and viral titers were quantified at 48 h postinfection. As shown in FIG. 27A, virus reductions were calculated as 92.3%, 92%, 90.5%, and 86.5% for addition of temoporfin at 0, 1, 3, and 22 hours postinfection, respectively. Temoporfin addition at 22 hours postinfection was almost as equally effective as that at time 0 postinfection. These results demonstrate that temoporfin is a potent inhibitor for ZIKV not only at an early stage of viral infection but also at late stage of replication.

Figure 27B:
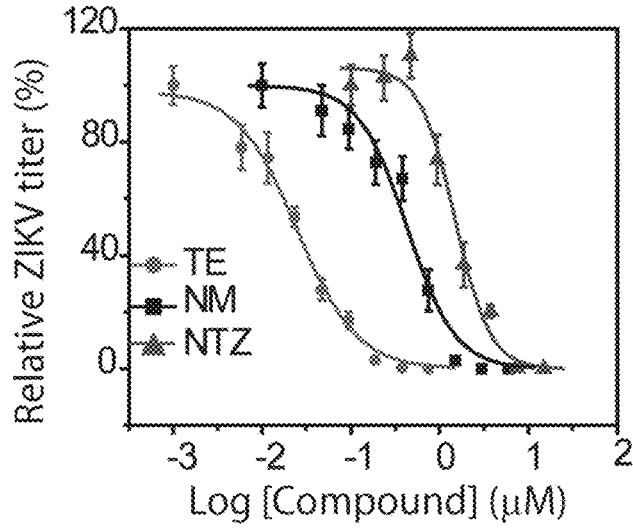
FIG. 27B is a graph showing dose-dependent inhibition of ZIKV by drugs in A549 cells by tizoxanide, niclosamide, and nitazoxanide, in a viral plaque reduction assayin accordance with the present disclosure.
Figure 27C:
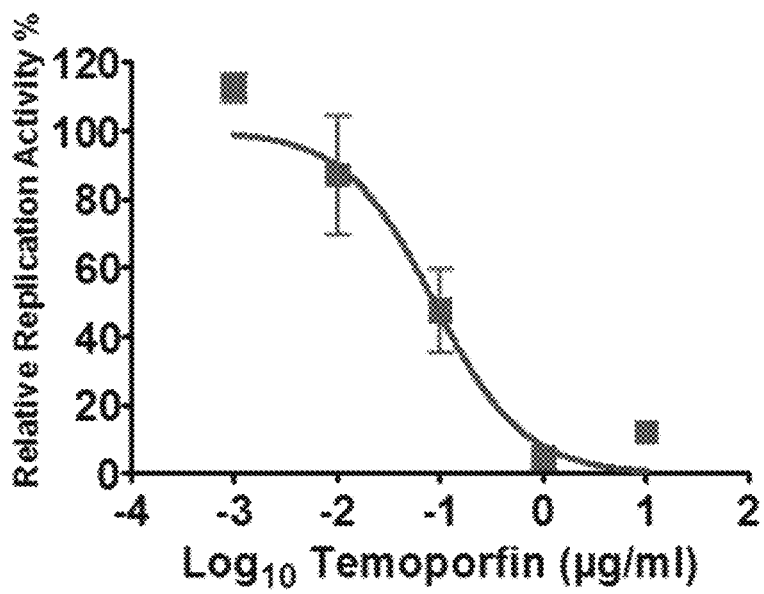
FIG. 27C is a graph showing dose-dependent inhibition of ZIKV strain GZO1 in Vero cells as assessed by RT-qPCR measurement of viral DNA (EC50 value of temoporfin=0.1 µg/ml).
Figure 27D:
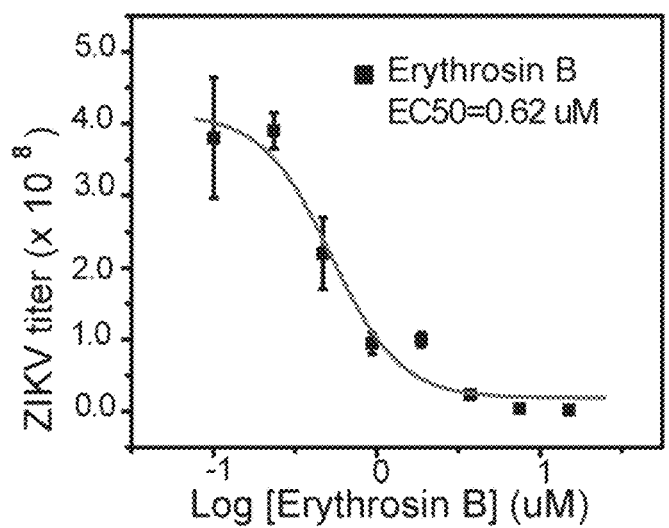
FIG. 27D is a graph showing dose-dependent inhibition of ZIKV by erythrosin B in A549 cells as assessed with a viral plaque reduction assay in accordance with the present disclosure.
Figure 27E:
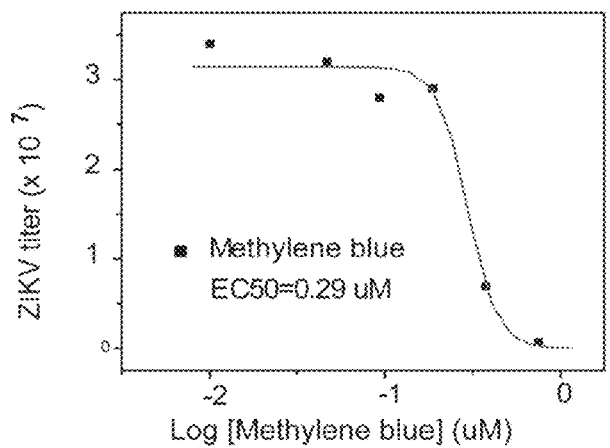
FIG. 27E is a graph showing dose-dependent inhibition of ZIKV by methylene blue in A549 cells as assessed with a viral plaque reduction assay in accordance with the present disclosure.
Figure 27F:
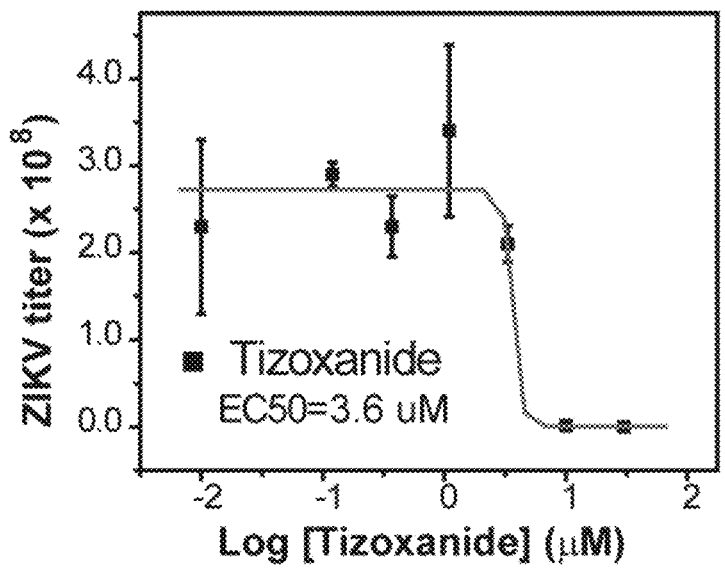
FIG. 27F is a graph showing dose-dependent inhibition of ZIKV by tizoxanide in A549 cells as assessed with a viral plaque reduction assay in accordance with the present disclosure.
Figure 28A:
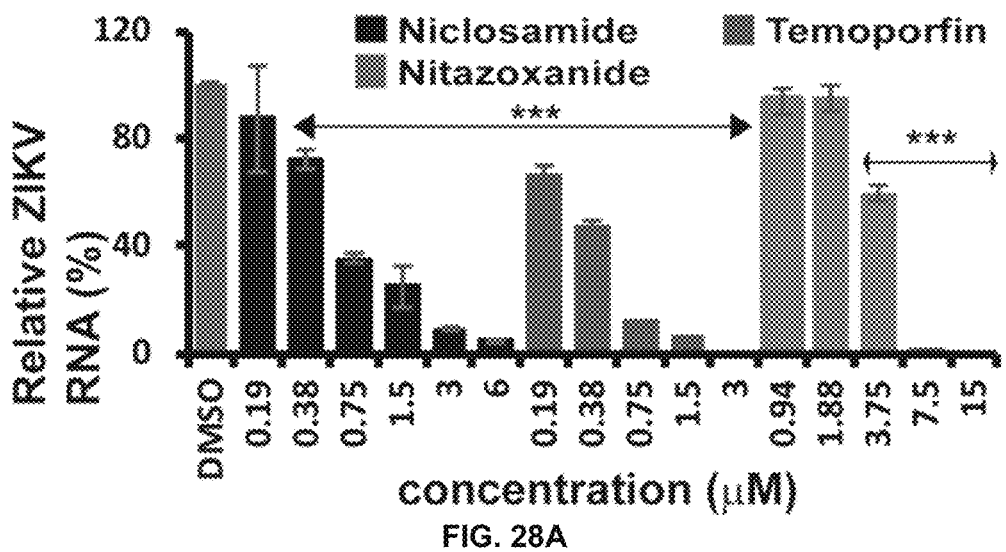
FIG. 28A is a graph showing dose-dependent inhibition of viral RNA from ZIKV-infected A549 cells by temoporfin, niclosamide, and nitazoxanide as assessed by qRT-PCR analysis in accordance with the present disclosure.

Antiviral effects of compounds was also tested against Zika virus. Dose-dependent inhibition of the Zika virus the Puerto Rico strain PRVABC59 by drugs in A549 cells is shown in FIGS. 27B (temoporfin, niclosamide, and nitazoxanide), 27D (erythrosin B), 27E (methylene blue), and 27F (tizoxanide, a metabolite of nitazoxanide), and against Zika virus Venezuela strain GZO1 in FIG. 27C (temoporfin).

qRT-PCR and immunofluorescence assays (IFA) were performed to further characterize the compounds' anti-viral effects. 50 µl of cell supernatant samples were extracted on Applied Biosystems MagMAX Express-96 Deep Well Magnetic Particle Processor. TaqMan gene expression qRT-PCR assays were performed with 5 ul of the extracted RNA using the TaqMan One-step RT-PCR Master Mix Reagents Kit (PE Biosystems) on Applied Biosystems 7500 Real-time PCR System. TaqMan primers for ZIKV are CCGCTGCC-CAACACAAG and CCACTAAYGTTCTTTTGCAGACAT with ZIKV probe Cy5-AGCCTACCT/TAO/TGACAAGCAGTCAGACACTCAA-IAbRQSp. Samples were analyzed by relative quantification using the 2-ΔΔCT ("delta-delta Ct") compared with the endogenous control. qRT-PCR results are shown in FIGS. 28A (temoporfin, niclosamide, and nitazoxanide) and 28C (erythrosin B).

Figure 28B:
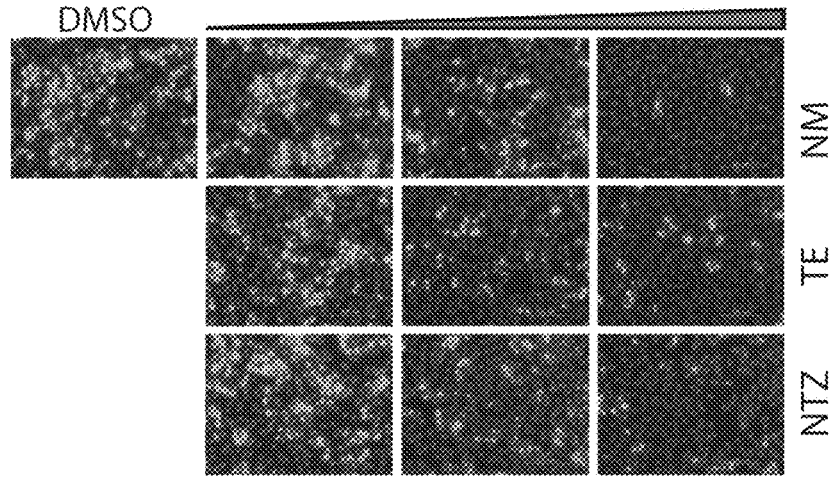
FIG. 28B shows immunofluorescence assay of inhibition of viral protein expression by temoporfin (0.06 µM, 0.56 µM, and 5 µM), niclosamide (0.19 µM, 0.57 µM, and 1.67 µM), and nitazoxanide (0.06 µM, 0.56 µM, and 5 µM), using pan-flavivirus anti-E 4G2 antibody (green) in accordance with the present disclosure. Cell nuclei are stained in blue.
Figure 28C:
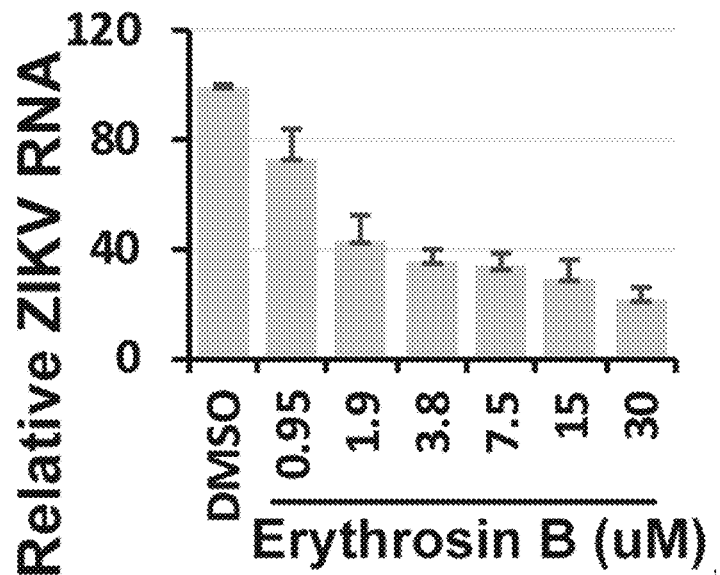
FIG. 28C is a graph showing dose-dependent inhibition of viral RNA from ZIKV-infected A549 cells by erythrosin B in accordance with the present disclosure.
Figure 28D:
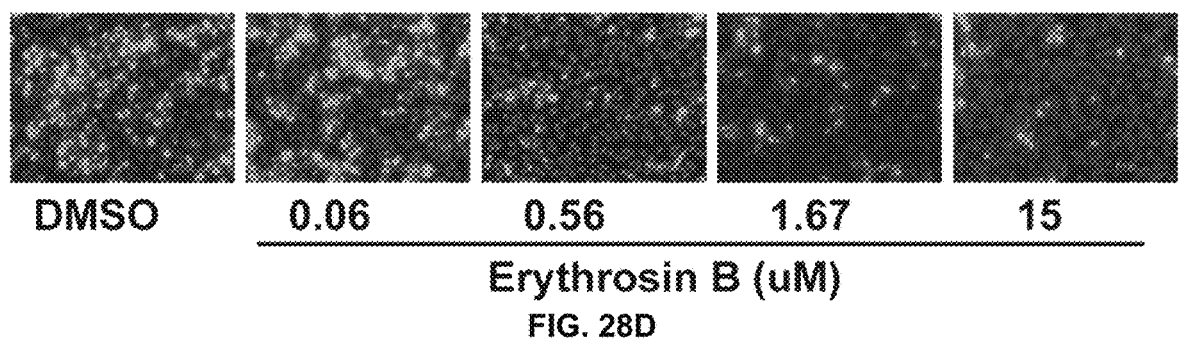
FIG. 28D shows immunofluorescence assay of inhibition of viral protein expression by erythrosin B, using pan-flavivirus anti-E 4G2 antibody (green) in accordance with the present disclosure. Cell nuclei are stained in blue.
Figure 28E:
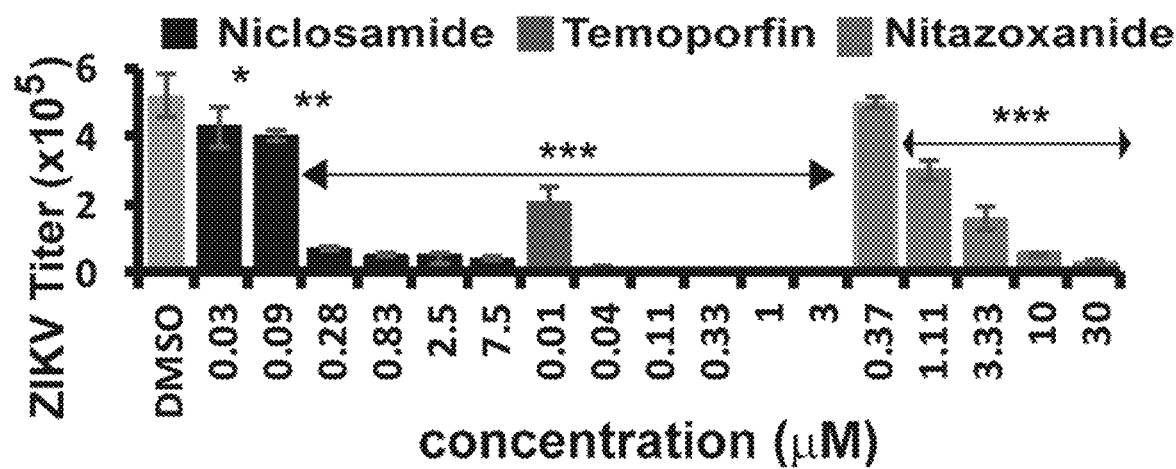
FIG. 28E is a graph showing dose-dependent inhibition of ZIKV by niclosamide, temoporfin, and nitazoxanide in human placental epithelial cells (HPECs) in accordance with the present disclosure.
Figure 28F:
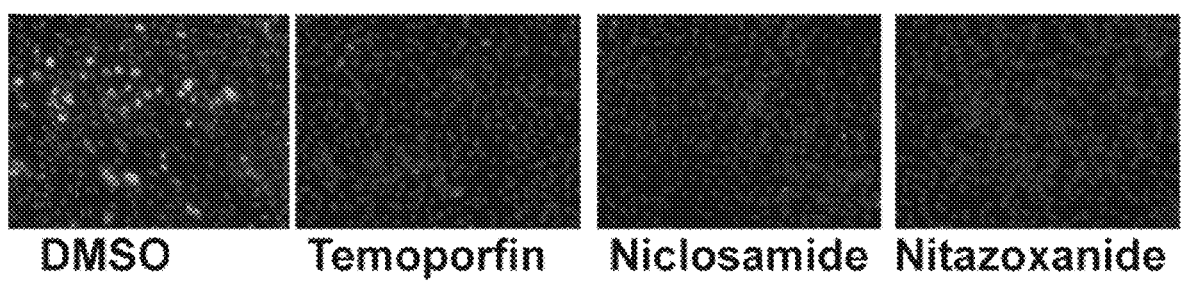
FIG. 28F shows immunofluorescence assay of inhibition of viral protein expression for ZIKV-infected HPECs by niclosamide (0.19 µM), temoporfin (0.06 µM), and nitazoxanide (10 µM) using pan-flavivirus anti-E 4G2 antibody (green) in accordance with the present disclosure. Cell nuclei are stained in blue.
Figure 28G:
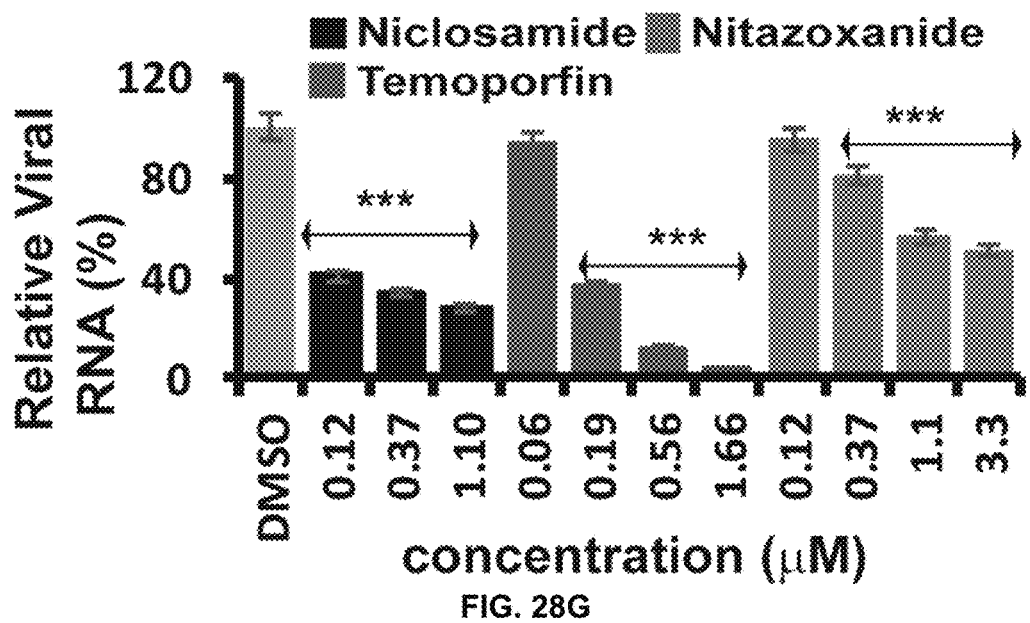
FIG. 28G is a graph showing dose-dependent inhibition of viral RNA of ZIKV-infected HPECs by niclosamide, temoporfin, and nitazoxanide as assessed by qRT-PCR analysis in accordance with the present disclosure.
Figure 28H:
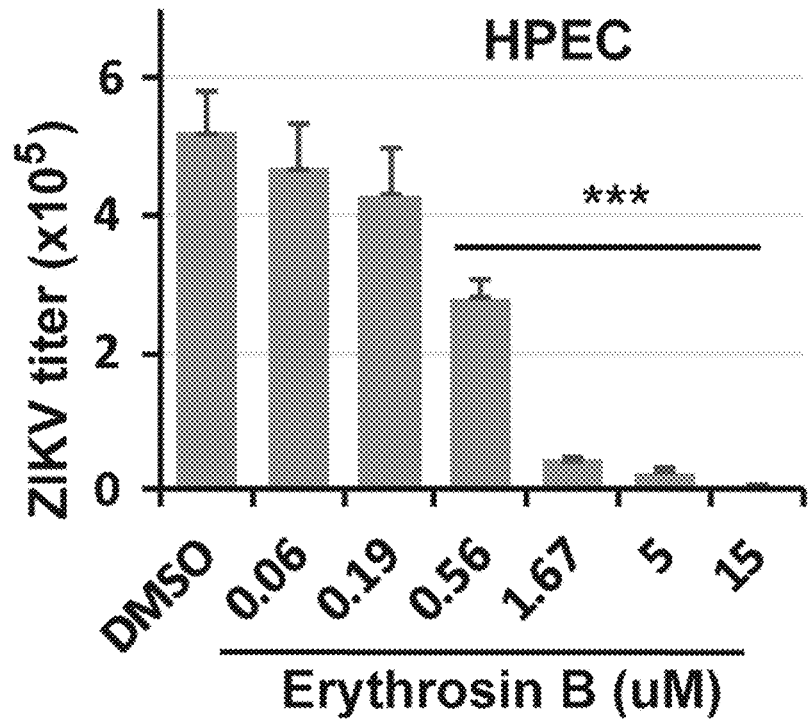
FIG. 28H is a graph showing dose-dependent inhibition of ZIKV by erythrosin B in HPECs (***, p<0.01) as assessed by viral plaque reduction assay in accordance with the present disclosure.
Figure 28I:
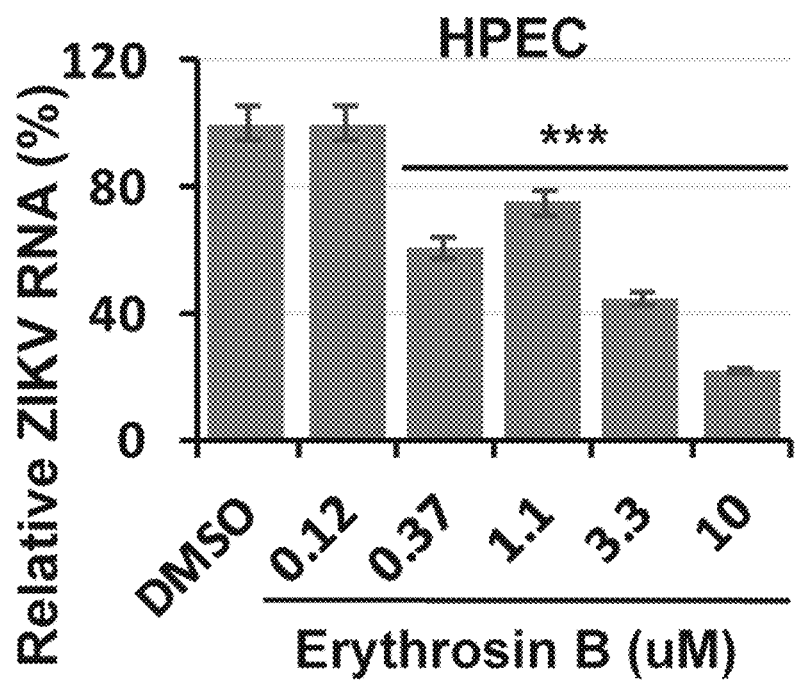
FIG. 28I is a graph showing dose-dependent inhibition of viral RNA of ZIKV-infected HPECs by erythrosin B as assessed by qRT-PCR analysis in accordance with the present disclosure.
Figure 28J:
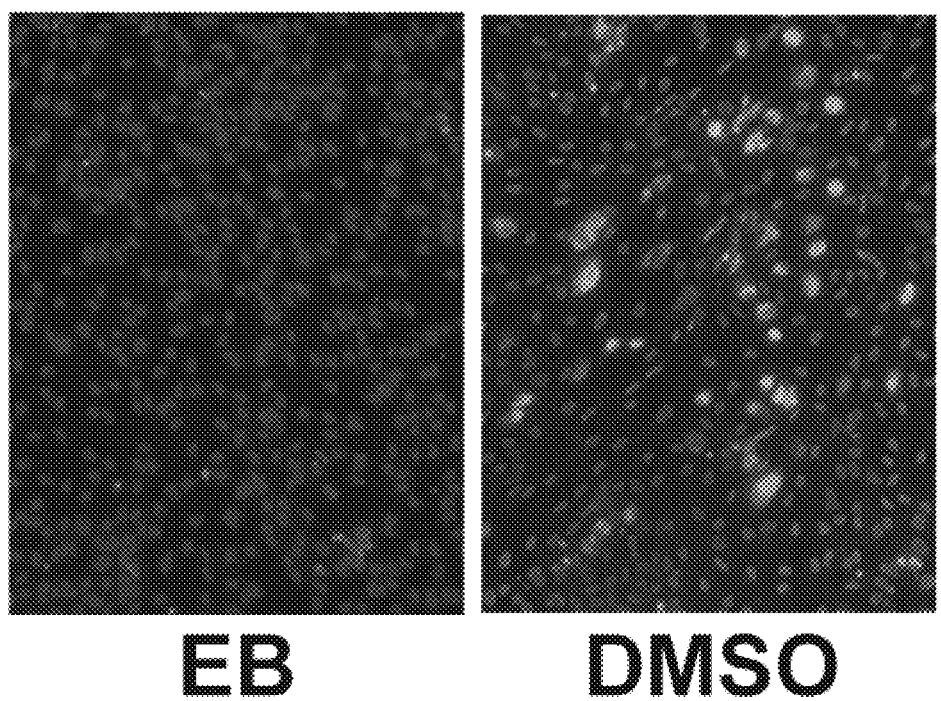
FIG. 28J shows immunofluorescence assay of inhibition of viral protein expression for ZIKV-infected HPECs by 0.12 µM erythrosin B using pan-flavivirus anti-E 4G2 antibody (green) in accordance with the present disclosure. Cell nuclei are stained in blue.
Figure 28K:
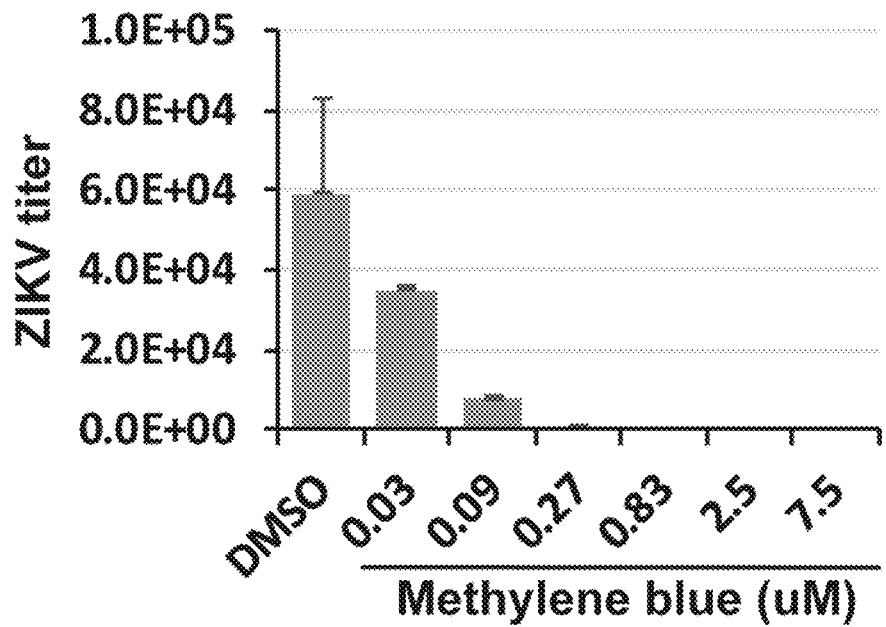
FIG. 28K is a graph showing dose response inhibition of ZIKV in HPECs by methylene blue as assessed by viral plaque reduction assay in accordance with the present disclosure.

For IFA, ZIKV-infected cells treated with DMSO or drugs were grown in 96-well black imaging plates (Corning). At 48-hr post-infection, growth medium was removed. The cells were washed once with PBS and fixed on ice in 100% pre-chilled (−20° C.) methanol for 15 min. The fixed cells were incubated for 1 hr with blocking and permeabilisation buffer containing 0.5% Triton X-100, 0.2 µg/ml EDTA and 1% BSA in PBS. The cells were then treated with a mouse monoclonal pan anti-E antibody 4G2 (ΔTCC) (green) overnight and washed three times with PBST buffer (1×PBS with 0.2% Tween 20). The cells were then incubated with the DyLight® 488 goat anti-mouse IgG (ImmunoReagents, Inc.) for 1 hr in blocking buffer, after which the cells were washed three times with PBST. Nuclear staining dye Hoechst (blue) was added and incubated for 5 min. Fluorescence images were recorded under a fluorescence microscope equipped with an Olympus DP71 imaging system. IFA results are shown in FIG. 28B (temoporfin at 0.06 µM, 0.56 µM, and 5 µM, niclosamide at 0.19 µM, 0.57 µM, and 1.67 µM, and nitazoxanide at 0.06 µM, 0.56 µM, and 5 µM) and 28D (erythrosin B). Additions of these drugs greatly reduced both viral RNA copy numbers and viral antigen expression in a dose-dependent manner.

Because ZIKV causes microcephaly in newborns after infecting fetus and placenta cells during pregnancy, ZIKV inhibition by these compounds was tested in human placental epithelial cells (HPECs) that derived from the inner surface of the amnion and have physiology relevant to fetal development and neurogenesis. Human primary placental epithelial cells (HPECs) derived from the inner surface of the amnion were purchased from Cell Applications, Inc., and cultured according to manufacturer's manual. FIG. 28E-28K show results on viral titer assessed by viral plaque reduction assay (FIG. 28E), IFA (FIG. 28F), and qRT-PCR (FIG. 28G) for niclosamide, temoporfin, and nitazoxanide, viral titer assessed by viral plaque reduction assay (FIG. 28H) and qRT-PCR assay (FIG. 28I), and IFA (FIG. 28J) for erythrosin B (0.12 m), and viral titer assessed by plaque reduction assay (FIG. 28K) for methylene blue in HPECs. All compounds effectively inhibited ZIKV in HPECs. Protein expression and viral RNA replication were also drastically decreased. Overall, these experiments demonstrate that these compounds are effective antivirals in placental cells relevant to ZIKV infection.

Because ZIKV also targets hNPCs and neurons, drug efficacy in human primary cells related to neurons was further evaluated. Pluripotent stem cell (iPSC) line HDF9 and iPSC-derived hNPC were induced. Human hNPC, derived from iPSC generated using the STEMCCA Cre-Excisable Constitutive Polycistronic (OKSM) lentivirus, was purchased from EMD Millipore, and cultured according to manufacturer's manual. Published human iPS cell line IPSC-HDF9 was cultured and maintained on pre-coated matrigel (BD Biosciences) plates and fed every 24 hours using mTSeR medium (STEMCELL Technologies). Cell lines were passaged at a 1:6 ratio after 70-80% confluency using Dispase (STEMCELL Technologies) and a cell scraper for gentle dissociation. Cells were manually picked, washed with DMEM, and re-plated onto matrigel-coated plates when necessary to ensure high-quality undifferentiated colonies. Undifferentiated iPSCs were counted with a hemocytometer and replated on matrigel at 200,000 cells per 24-well plate or 20,000 cells per 96-well plate before infection with ZIKV.

Figure 28L:
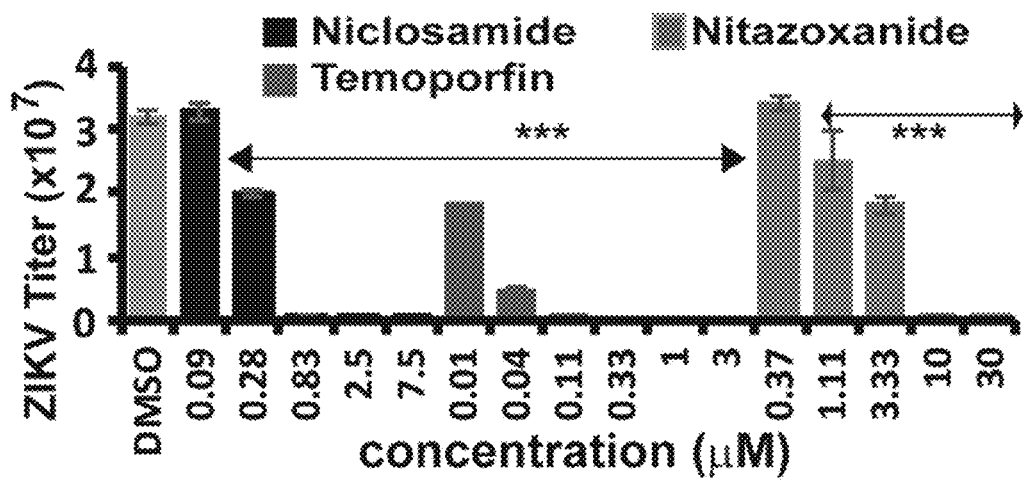
FIG. 28L is a graph showing dose-dependent inhibition of ZIKV by niclosamide, temoporfin, and nitazoxanide in induced pluripotent stem cell (iPSC) line HDF9-derived human neural progenitor cells (hNPCs) in accordance with the present disclosure.
Figure 28M:
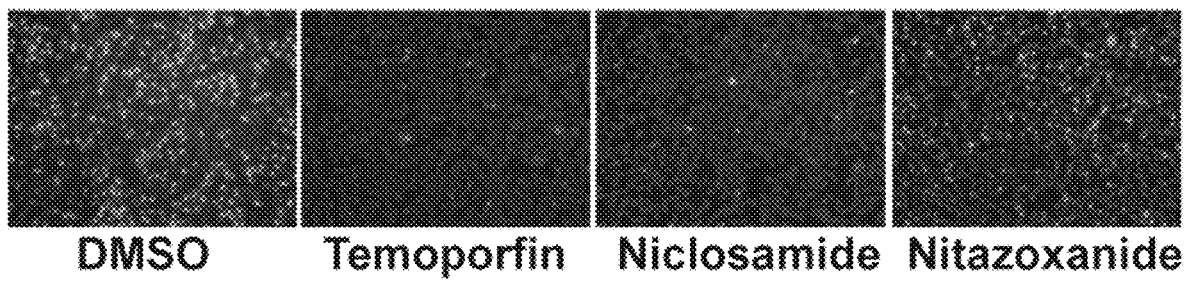
FIG. 28M shows immunofluorescence assay of inhibition of viral protein expression for ZIKV-infected hNPCs by temoporfin (1.0 µM), niclosamide (0.83 µM) and nitazoxanide (3.3 µM) using pan-flavivirus anti-E 4G2 antibody (green) in accordance with the present disclosure.
Figure 28N:
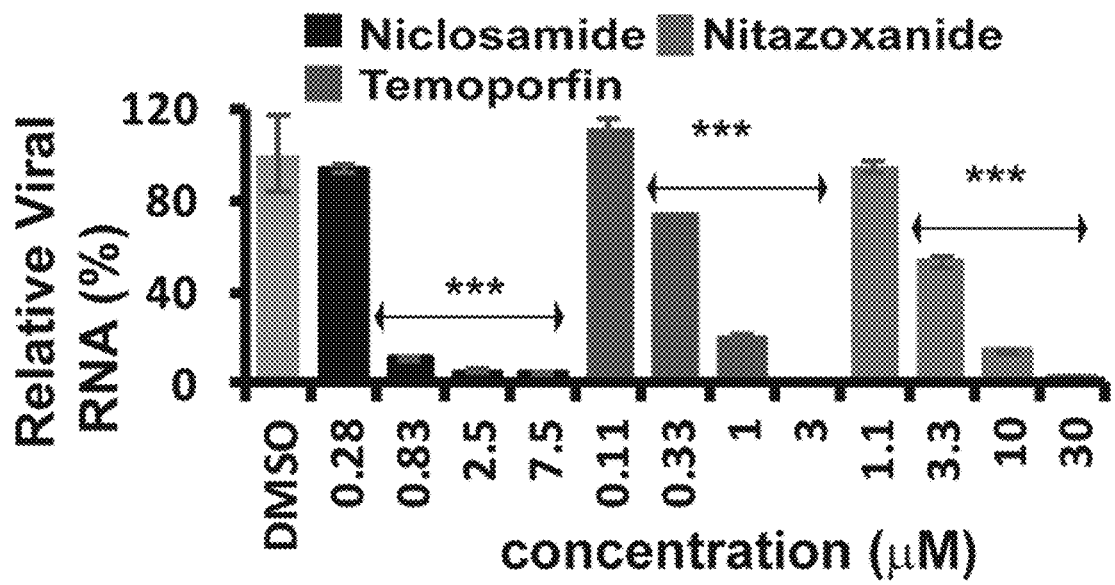
FIG. 28N is a graph showing dose-dependent inhibition of viral RNA of ZIKV-infected hNPCs by niclosamide, temoporfin, and nitazoxanide as assessed by qRT-PCR analysis in accordance with the present disclosure.
Figure 28O:
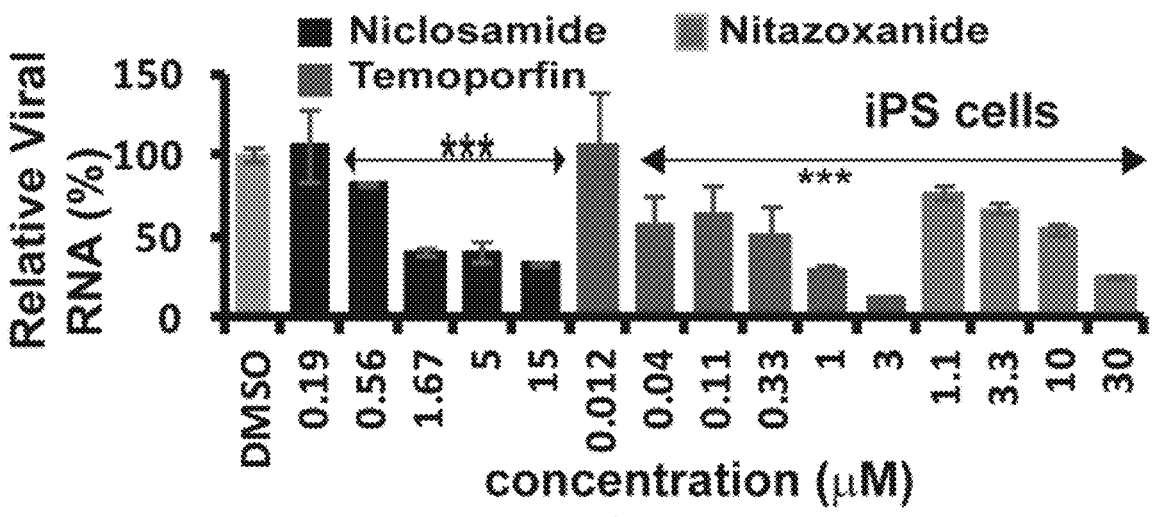
FIG. 28O is a graph showing dose-dependent inhibition of viral RNA of ZIKV-infected iPSC HDF9 by niclosamide, temoporfin, and nitazoxanide as assessed by qRT-PCR analysis in accordance with the present disclosure.
Figure 28P:
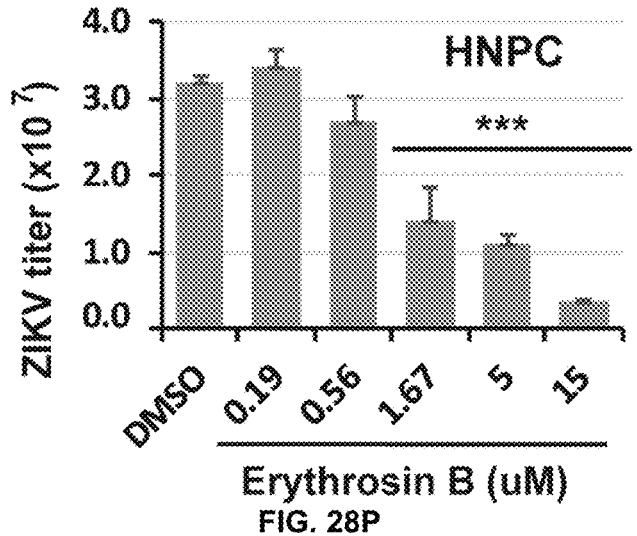
FIG. 28P is a graph showing dose-dependent inhibition of ZIKV by erythrosin B in hNPCs (***, p<0.01) as assessed by viral plaque reduction assay in accordance with the present disclosure.
Figure 28Q:
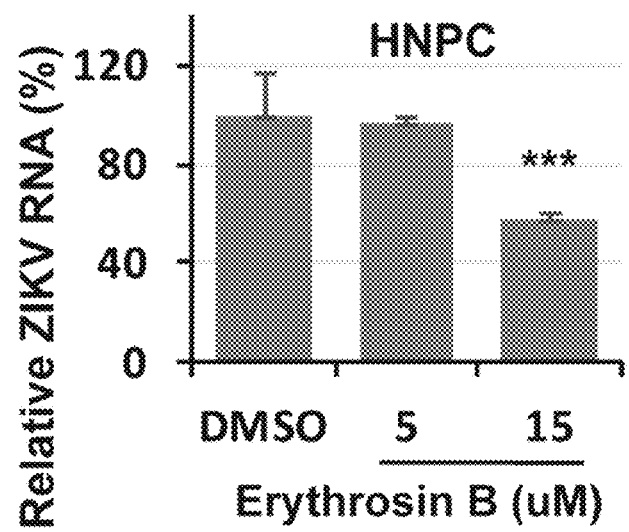
FIG. 28Q is a graph showing dose-dependent inhibition of viral RNA of ZIKV-infected hNPCs by erythrosin B as assessed by qRT-PCR analysis in accordance with the present disclosure.
Figure 28R:
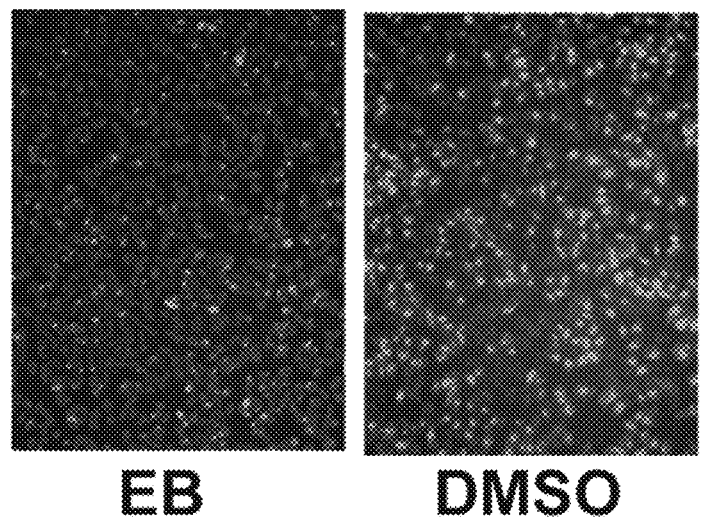
FIG. 28R shows immunofluorescence assay of inhibition of viral protein expression for ZIKV-infected hNPCs by 1.67 µM erythrosin B using pan-flavivirus anti-E 4G2 antibody (green) in accordance with the present disclosure. Cell nuclei are stained in blue.

Anti-Zika viral effects in for temoporfin, niclosamide, and nitazoxanide on ZIKA viral titers, protein, and RNA expression in iPSC-derived hNPCs are shown in FIGS. 28L (viral plaque reduction assay), 28M (IFA; temoporfin 1.0 µM, niclosamide 0.83 µM, nitazoxanide 3.3 M), and 28N (qRT- PCR). FIG. 28O shows the effects of temoporfin, niclosamide, and nitazoxanide on Zika viral RNA expression in ZIKV-infected iPSC HDF9 cells by qRT-PCR. Effects of erythrosin B on Zika viral titers and IFA (1.67 μM) in hNPCs are shown in FIGS. 28P-28R, respectively. All compounds drugs considerably reduced ZIKV titers according to plaque reduction assay, IFA, and qRT-PCR in hNPC and HDF9 iPSC.

Because it was possible that some reduction in viral titer could be the result of compound cytotoxicity, the viability of A549 cells in the presence of a range of compound concentrations was measured. Cytotoxicity for temoporfin and erythrosin B was measured by a MTT cell proliferation assay using the 3-(4,5-dimethylthiazol-2-yl)-2,5-diphenyl tetrazolium bromide method (ATCC). Cytotoxicity for niclosamide, nitazoxanide, and methylene blue was measured by a WST-8 cell proliferation assay (Dojindo Molecular Technologies, Inc.), according to manufacturer's protocol. Briefly, approximately $1 \times 10^5$ cells in 100 μl of media were seeded into 60 wells of a 96 well plate, while the remaining wells held media. Plates were held at RT for 1 hour and then incubated for 20-24 hours. The media was removed, and 100 μl of media containing decreasing concentrations of antiviral compound in 1% DMSO were added to the wells. All determinations were performed in triplicate. After 42 hours incubation at 37° C., MTT or WST-8 assays were performed according to manufactories' protocols. A microtiter plate reader (Ely808, BioTek Instruments, Inc.) with a 570 nm filter (MTT) or 450 nM (WST-8) was used to record absorbance. After adjusting the absorbance for background and comparing to untreated controls, the cytotoxic concentration $CC_{50}$ was calculated using a sigmoidal non-linear regression function to fit the dose-response curve using the ORIGIN Suite6.0 (Origin Lab, Wellesley Hills, Mass.).

Figure 29A:
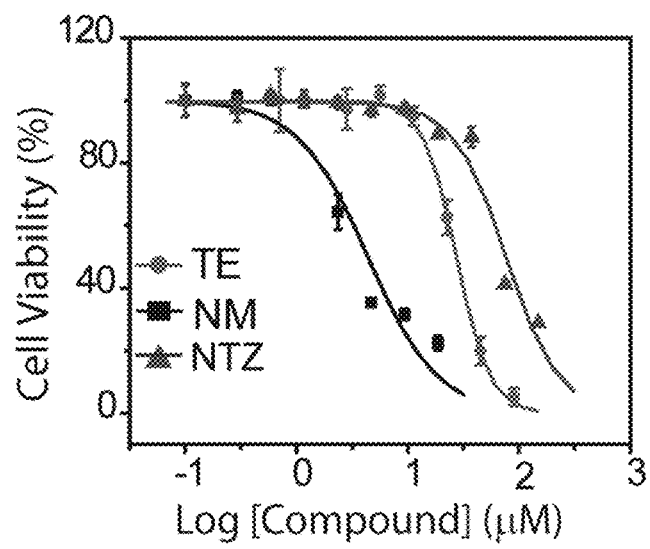
FIG. 29A, FIG. 29B, and FIG. 29C are graphs showing cell viability assays of A459 treated with temoporfin, niclosamide, nitazoxanide, erythrosin B, and methylene blue in accordance with the present disclosure. Viability in the presence of temoporfin and erythrosin B was measured by an MTT cell viability assay and, in the presence of niclosamide, nitazoxanide, and methylene blue, by a WST-8 assay.
Figure 29B:
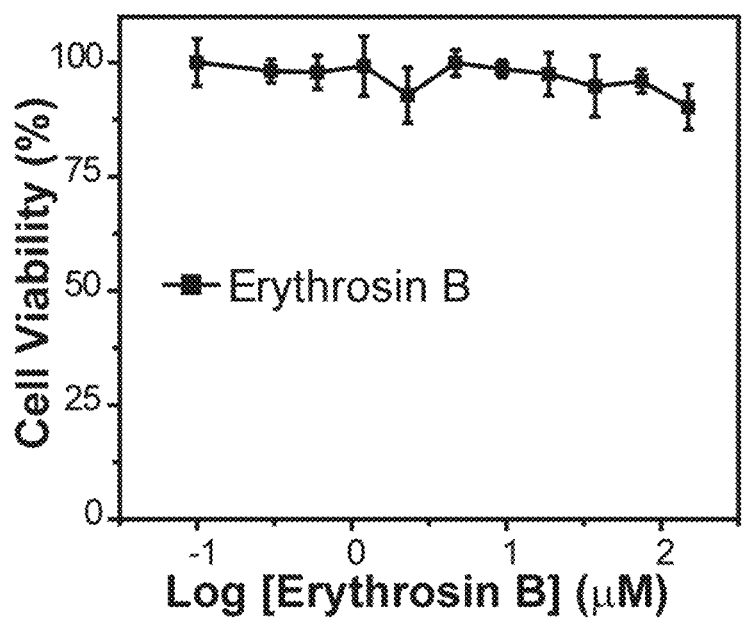
Figure 29C:
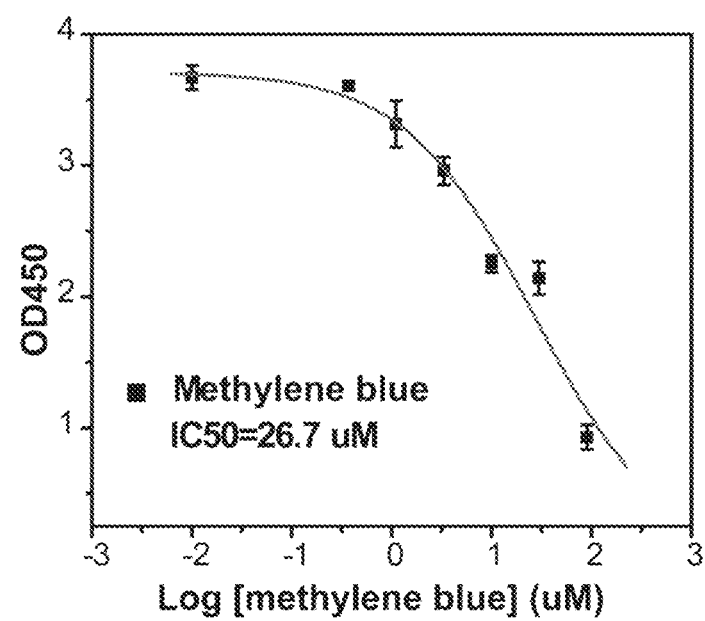

Cytotoxicity results for tizoxanide, niclosamide, and nitazoxanide are shown in FIG. 29A, for erythrosin B are shown in FIG. 29B, and for methylene blue are shown in FIG. 29C. Cytotoxicity results are also shown in Tables 1 and 3. $CC_{50}$ (the concentration of compound at which 50% cells are viable) for nitazoxanide, niclosamide, erythrosin B, and methylene blue were all larger than 100 μM and temoporfin has a $CC_{50}$ of 40.7 μM on A549 cells.

A therapeutic index (TI) was calculated for compounds as a ratio of $EC_{50}$ (concentration of inhibitor required to reduce virus growth by 50%) to $CC_{50}$ (concentration of inhibitor required to reduce cell viability by 50%). By this measure, a higher TI corresponds to higher antiflaviviral potency and lower cytotoxicity. As shown in Tables 1 and 3, several compounds had high TI values against multiple flaviviruses, indicating their potential utility as pharmaceutical compounds for broad spectrum antiflaviviral activity.

Temoporfin is a photosensitizer used in photodynamic therapy for the treatment of squamous cell carcinoma of the head and neck. Lorenz & Maier (2008), HNO 56, 402-409; O'Connor et al. (2009), Photochem Photobiol 85, 1053-1074. Methylene blue photoinactivation may also affect WNV infectivity. Papin et al. (2005), Antiviral Res 68, 84-87. An inhibition experiment was therefore performed in dark without exposure to light. Results are shown in Table 3. Temoporfin and methylene blue significantly reduced the titer of ZIKV in the absence of light exposure. The $EC_{50}$ efficacies for temoporfin to inhibit ZIKV with/without ambient light exposure were nearly the same. Temoporfin worked equally well under no light exposure for inhibitions of other flaviviruses. These results demonstrate that temoporfin and methylene blue do not require photoactivation to inhibit flavivirus titer.

Figure 30:
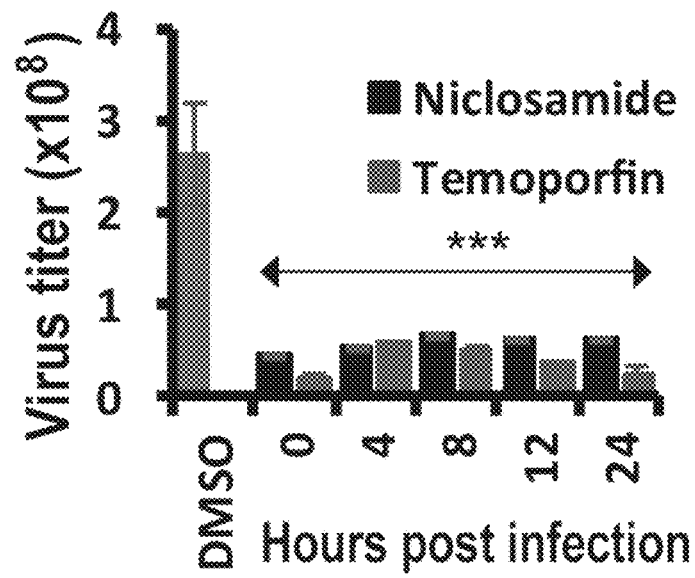
FIG. 30 is a graph showing a time-of-addition study of ZIKV inhibition in A549 cells by temoporfin (90 nM) and niclosamide (0.75 µM) in accordance with the present disclosure.

FIG. 30 shows the results of a time-of-addition experiment (viral plaque reduction assay) characterizing the mode of inhibition for niclosamide (0.75 μM) and temoporfin (90 nM). Additions of temoporfin or niclosamide at 24-hour post-infection were almost equally effective as additions at the time of infection, indicating that temoporfin and niclosamide are potent inhibitors for ZIKV during not only early stages of viral infection, but also in the late stages of viral replication.

Figure 31A:
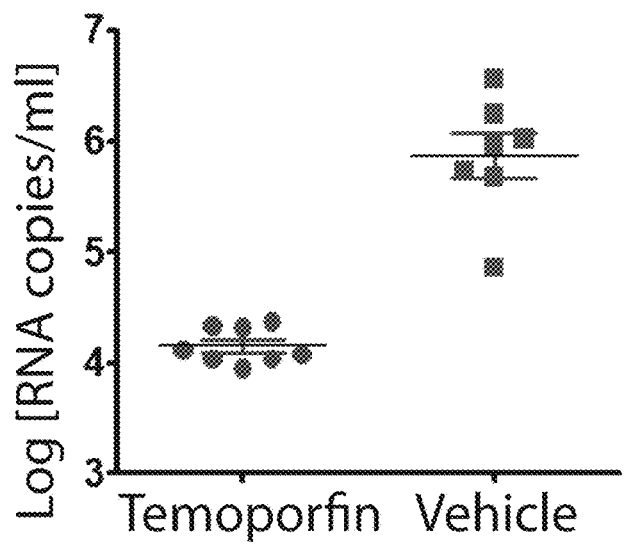
FIG. 31A and FIG. 31B are graphs demonstrating in vivo antiviral activity of temoporfin against Zika virus in accordance with the present disclosure. For FIG. 31A, viremia was detected by RT-qPCR on day 2 post-ZIKV infection in three-week old Balb/C mice. Difference between temoporfin (n=8) or vehicle (n=7) treatment was analyzed by using the unpaired, two-tailed T-test. For FIG. 31B, survival percentage for four-week old A129 mice infected with ZIKV and treated with temoporfin (n=12) or vehicle (n=10). Survival curves were compared using the Log-rank test.

In vivo anti-ZIKV potential of temoporfin using mouse models was also tested, in both a viremia model and a lethal A126 mouse model. For the viremia model in immunocompetent Balb/C mice, a group of three-week-old female Balb/c mice infected intraperitoneally (ip) with $2 \times 10^5$ PFU of ZIKV strain GZO1/2016 were intraperitoneally (ip) administered temoporfin at 0.02 mg/mice (n=8) or vehicle control (n=7) every day for 2 consecutive days post-infection (dpi). Viremia on day 2 post-infection (pi) was determined by RT-qPCR, and statistical analysis was performed using the unpaired, two-tailed t-test. Results, shown in FIG. 31A, demonstrate that temoporfin treatment significantly resulted in about 100-fold reduction in ZIKV-induced viremia in immunocompetent Balb/C mice compared to the vehicle control.

Figure 31B:
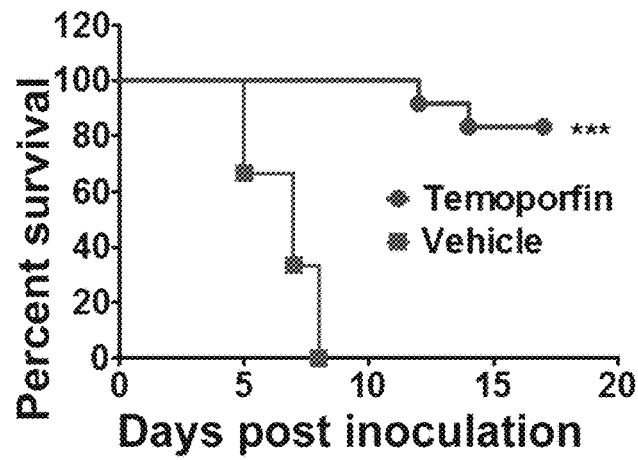

For the lethal A129 mice model, a group of four-week old A129 mice were infected intraperitoneally (ip) with $2 \times 10^5$ PFU of ZIKV GZO1/2016 strain. Then, the infected mice were ip administered with temoporfin at 1 mg/kg of body weight (n=12) or with vehicle control (n=10) every day for 5 consecutive days post-infection (dpi). Mice were observed daily for signs of illness and mortality. Survival curves were compared using the Log-rank test. All the ZIKV-infected animals treated with vehicle died with typical neurological symptoms including hind limb weakness and paralysis (FIG. 31B). Significantly, treatment with 1 mg/kg temoporfin for 5 days protected 83% of the infected animals. All survival mice did not show any neurological signs. Viremia was detected by RT-qPCR on day 2 post-ZIKV infection in three-week old Balb/C mice. These results confirm in vivo anti-viral efficacy.

Figure 32A:
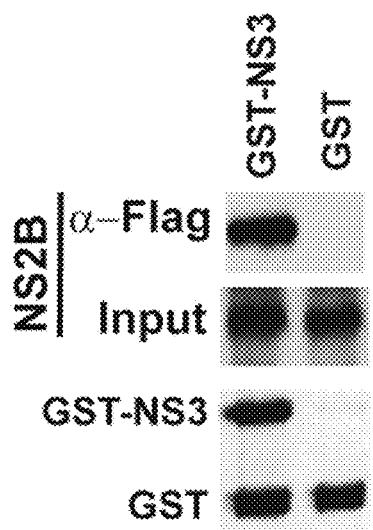
FIG. 32A shows the results of a GST pull-down assay. GST-NS3 or GST-tag (10 µg) was immobilized on Glutathione sepharose-4B affinity beads (GE HealthCare). FLAG-tagged NS2B (10 µg) was incubated with the beads for 2 hours, and subjected to western blotting, using anti-FLAG (Genscript) and anti-GST antibodies (GE HealthCare).
Figure 32B:
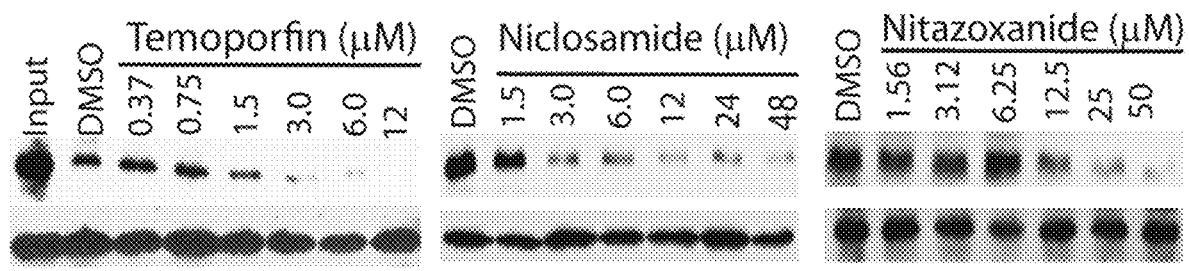
FIG. 32B shows dose-dependent inhibition of NS2B-NS3 interactions by drugs, using a GST pull-down assay, performed the same as in FIG. 32A, except that 2-fold dilution series of drugs were incubated with the GST-NS3 beads overnight prior to incubation with the FLAG-NS2B. Bottom panels showed normalized binding of FLAG-tag NS2B to GST-NS3. The binding of NS2B to NS3 in the absence of each drug (DMSO control) was set as 100%. The relative binding of NS2B to NS3 in the presence of each drug was normalized to the DMSO control.

GST-tagged ZIKV GST-NS3 protease domain and FLAG-tagged ZIKV NS2B cofactor were generated for competitive GST pull-down (PD) assay using immobilized GST-NS3 and FLAG-tagged NS2B. GST-NS3 or the GST-tag (10 μg) was immobilized on Glutathione sepharose-4B affinity beads (GE HealthCare). FLAG-tagged NS2B (10 μg) was incubated with the beads for 2 hours, and subjected to WB, using anti-FLAG (Genscript) and anti-GST antibodies (GE HealthCare). FIG. 32A shows WB results indicating that that FLAG-tagged NS2B could be specifically pulled down by GST-NS3 but not by the GST tag. Pre-incubation of temoporfin, niclosamide, or nitazoxanide with immobilized GST-NS3 beads significantly decreased the binding of the FLAG-NS2B to the GST-NS3, and did so in a dose-dependent manner. Results are shown in FIG. 32B. The assay was performed the same as in FIG. 32A, except that 2-fold dilution series of drugs were incubated with the GST-NS3 beads overnight prior to incubation with the FLAG-NS2B. Bottom panels showed normalized binding of FLAG-tag NS2B to GST-NS3. The binding of NS2B to NS3 in the absence of each drug (DMSO control) was set as 100%. The relative binding of NS2B to NS3 in the presence of each drug was normalized to the DMSO control. The results indicate that temoporfin, niclosamide and nitazoxanide each may specifically disrupt the interactions between the viral NS2B co-factor and the NS3 protease domain in vitro.

Figure 33:
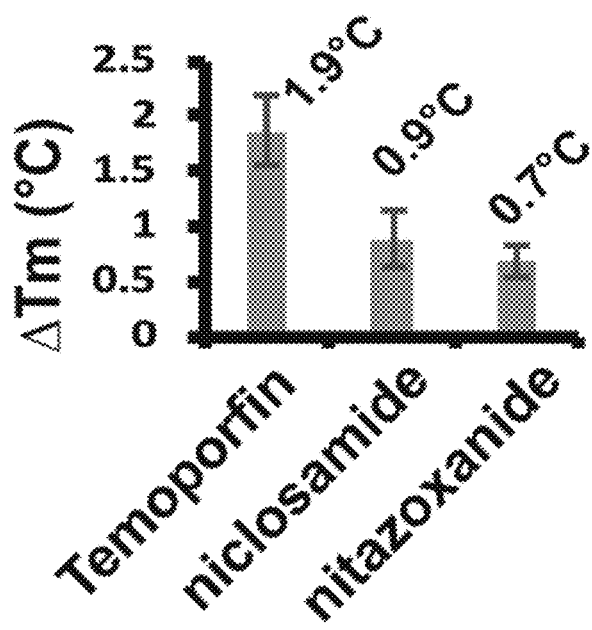
FIG. 33 is a graph showing results of a protein thermal-shift assay (PTSA) for binding of temoporfin, niclosamide, and nitazoxanide to MBP-NS3 protein, in accordance with the present disclosure. $\Delta T_m$ was defined as $T_{m\text{-}drug} - T_{m\text{-}DMSO}$.

Protein thermal shift assays (PTSA) were also performed to investigate binding of temoporfin, niclosamide, or nitazoxanide to NS3. PTSA was conducted using an Applied Biosystem 7500 Fast Real-Time PCR System (ThermoFisher Scientific) from 25 to 80° C. The DENV2 His-MBP-NS3 (final concentration of 2.5 µM in 1×PBS) was mixed with each compound to attain a 4.8 µM final concentration in 1.6% DMSO in the MicroAmp® Fast Optical 96-Well Reaction Plate (ThermoFisher Scientific). Thermal denaturation was monitored using SYPRO Orange (Life Technologies) according to manufacturer's manual. The denaturation of the proteins was monitored by following the increase of the fluorescence emitted by the probe that binds exposed hydrophobic regions of the denatured protein. The melting temperature ($T_m$) was calculated as the mid-log of the transition phase from the native to the denatured protein, using a Derivative model using the Protein Thermal Shift™ Software v1.0 (ThermoFisher Scientific). The reference unfolding temperature of proteins in 1.6% DMSO ($T_{m\text{-}DMSO}$) was subtracted from the values in the presence of each compounds ($T_{m\text{-}comp}$) to obtain thermal shifts, $\Delta T_m = T_{m\text{-}comp} - T_{m\text{-}DMSO}$. Compounds were considered to be binders when $\Delta T_m > 0.5°$ C. Treatment with temoporfin, niclosamide, or nitazoxanide led to increased $T_m$ for purified DENV2 MBP-NS3 protein, compared to the DMSO control (FIG. 33). These data indicate that temoporfin, niclosamide, or nitazoxanide may bind to flaviviral NS3 protein, resulting in stabilization of the NS3 conformation leading to $T_m$ increase.

Figure 34A:
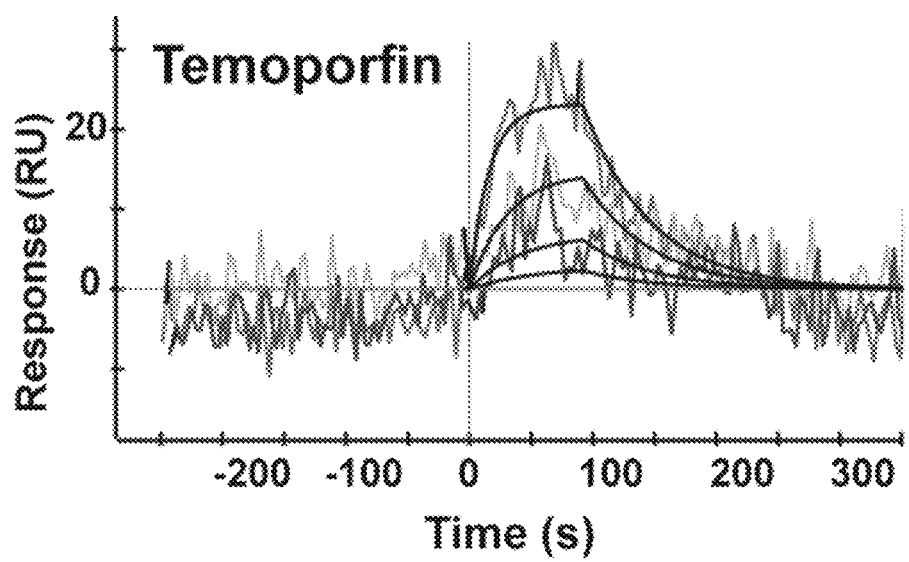
FIG. 34A, FIG. 34B, and FIG. 34C are surface plasmon resonance (SPR) sensograms of kinetic data for the binding of NS2B to refolded NS3 to determine the binding affinity between the identified drugs and the refolded NS3 protease domain, in accordance with the present disclosure. Refolded His-NS3 was coupled to a ProteOn™ GLH sensor chip (~15,000 RU). Concentrations used for the injected compounds ranged from 1 µM to 37 nM (temoporfin), from 9 µM to 333 nM (niclosamide), and from 10 µM to 370 nM (nitazoxanide), with 3-fold dilutions. Global fitting of data to a 1:1 binding model is shown in dark black.
Figure 34B:
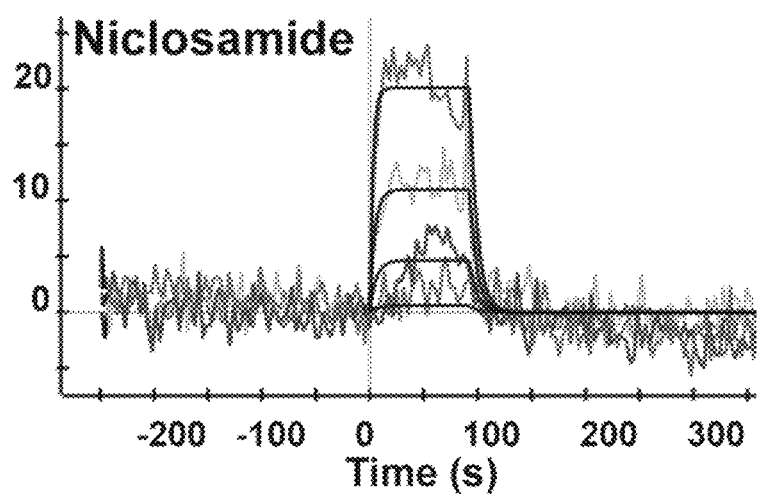
Figure 34C:
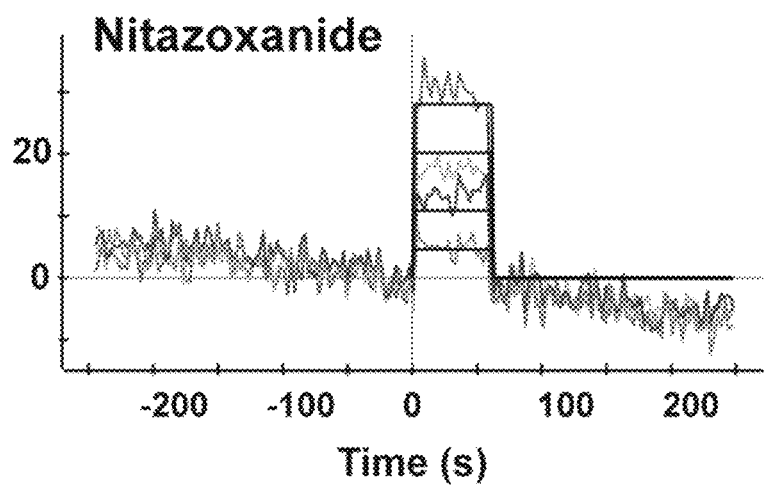

Surface plasmon resonance (SPR) was also performed to determine the binding affinity between temoporfin, niclosamide, or nitazoxanide and refolded NS3 protease domain. Affinity and kinetic analyses of the interactions between each drug and the His-NS3 protease domain were determined using a ProteOn XPR36 SPR instrument (Bio-Rad) at 25° C. Refolded His-NS3 was immobilized (~15,000 RU) onto a ProteOn™ GLH sensor chip (Bio-Rad). The concentrations used for the injected compounds ranged from 1 µM to 37 nM (temoporfin), from 9 µM to 333 nM (niclosamide), and from 10 µM to 370 nM (nitazoxanide), with 3-fold dilutions. A blank surface blocked by ethanolamine was used as the control surface. To minimize nonspecific binding, we carried out all of the binding experiments in a PBSTD buffer containing 1×PB, 0.005% surfactant P20, and 5% DMSO, at a flow rate of 100 µl/min. Association (ka) and dissociation (kd) rates, as well as the dissociation constant ($K_D$), were obtained by global fitting of the SPR data from multiple concentrations to a simple 1:1 Langmuir binding model, using the ProteOn Manager software suite (Bio-Rad). Results for temoporfin, niclosamide, and nitazoxanide are shown in FIGS. 34A-34C, respectively. Temoporfin, niclosamide, and nitazoxanide bound to the NS3 protease domain with low micromolar affinity, in the order of temoporfin (0.4 µM)>niclosamide (6.4 µM)>nitazoxanide (7.3 µM).

The ability of compounds to inhibit viral protein expression was also tested by WB, using GTX133309 ZIKV α-NS3 antibody (GeneTex, Inc.). Dose-dependent inhibition of ZIKV NS3 expression by temoporfin, niclosamide, and nitazoxanide is shown in FIGS. 35A-35F. WB (FIGS. 35A, 35C, and 35E) show that expression of ZIKV NS3 (~70 KDa) was significantly inhibited by temoporfin, niclosamide, and nitazoxanide in a dose-dependent manner. For samples treated with temoporfin, niclosamide, and nitazoxanide, an accumulation of high molecular weight (MW) protein (>>180 KDa) was also observed, which was absent in the DMSO controls. For temoporfin-treated samples (FIGS. 35A-35B), a dose-dependent increase of the high MW protein was seen at concentrations from 0.2 µM to 1.5 µM, and gradually declined from 3.0 µM to 6.0 µM. At low concentrations of temoporfin, a clear inverse relationship was observed between the accumulation of the high MW protein and the decrease of NS3 protein expression.

For samples treated with low concentrations of niclosamide (0.75 µM) (FIGS. 37C-D) and nitazoxanide (3.75 µM) (FIGS. 37E-F), a significant accumulation of high MW protein was also observed. For samples treated with drugs at higher concentrations (1.5 M and 7.5 µM for niclosamide and nitazoxanide, respectively), the accumulation of the high MW protein was less significant. At the highest drug concentrations, both NS3 expression and the high MW protein level could not be detected.

Figure 35A:
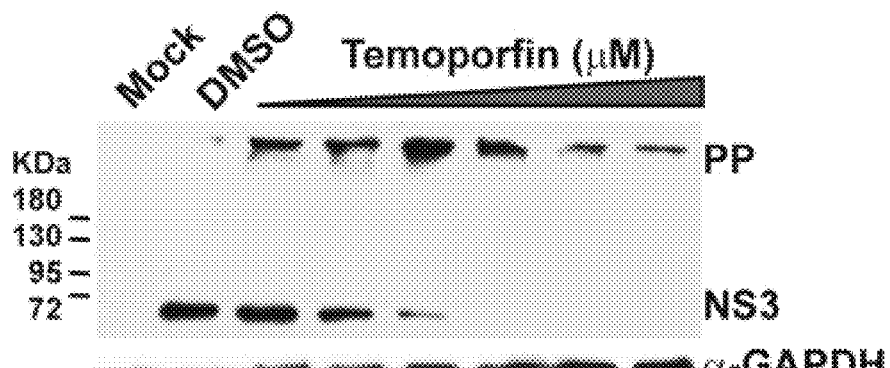
FIG. 35A, FIG. 35B, FIG. 35C, FIG. 35D, FIG. 35E, and FIG. 35F show western blot analysis of dose-dependent inhibition of ZIKV NS3 expression by temoporfin (FIGS. 35A and 35B), niclosamide (FIGS. 35C and 35D), and nitazoxanide (FIGS. 35E and 35F) using GTX133309 ZIKV α-NS3 antibody (GeneTex, Inc.) in accordance with the present disclosure. Experiment was performed at 48 hrs time point.
Figure 35B:
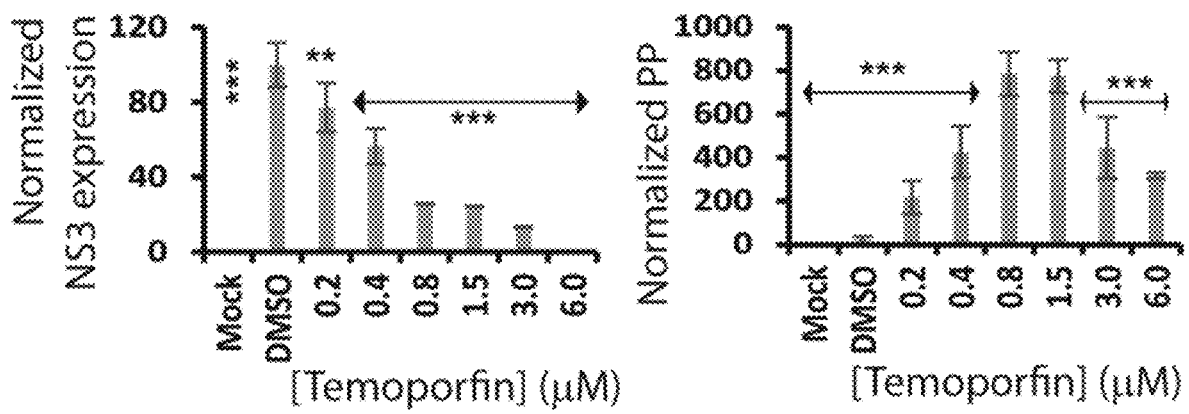
Figure 35C:
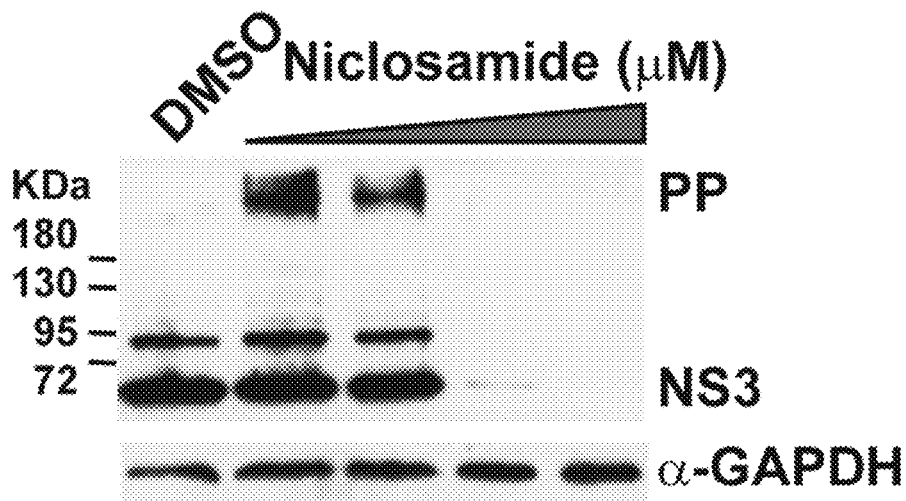
Figure 35D:
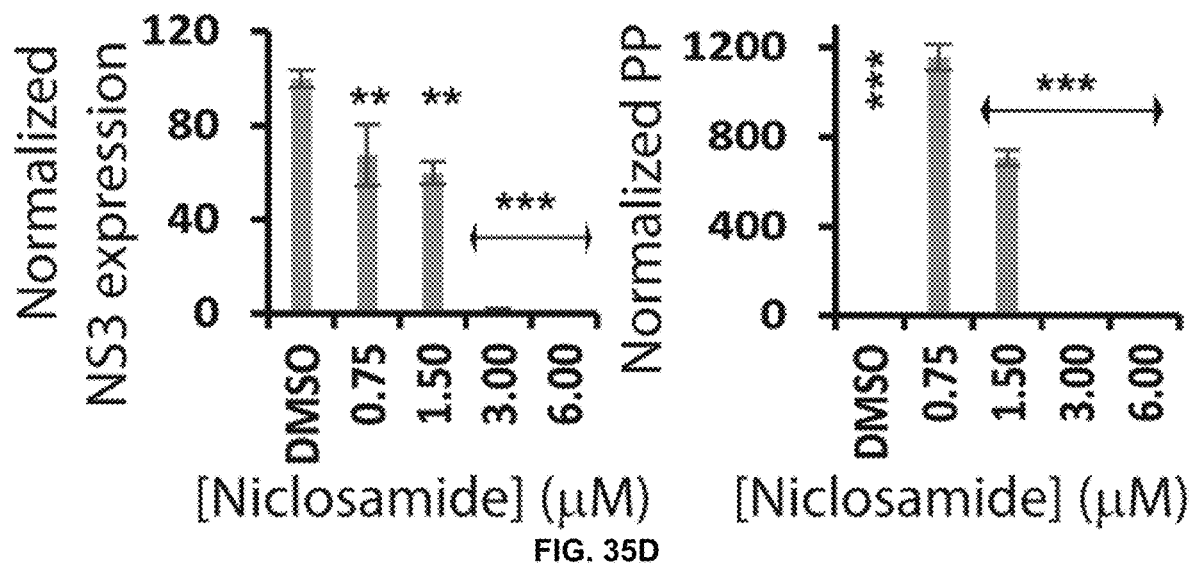
Figure 35E:
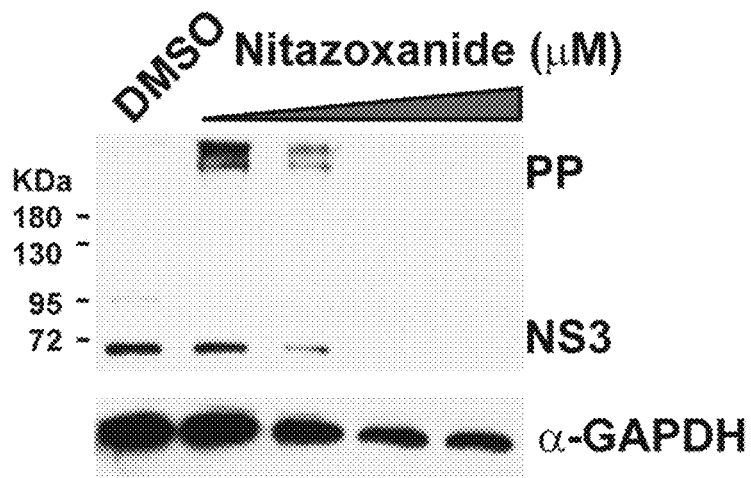
Figure 35F:
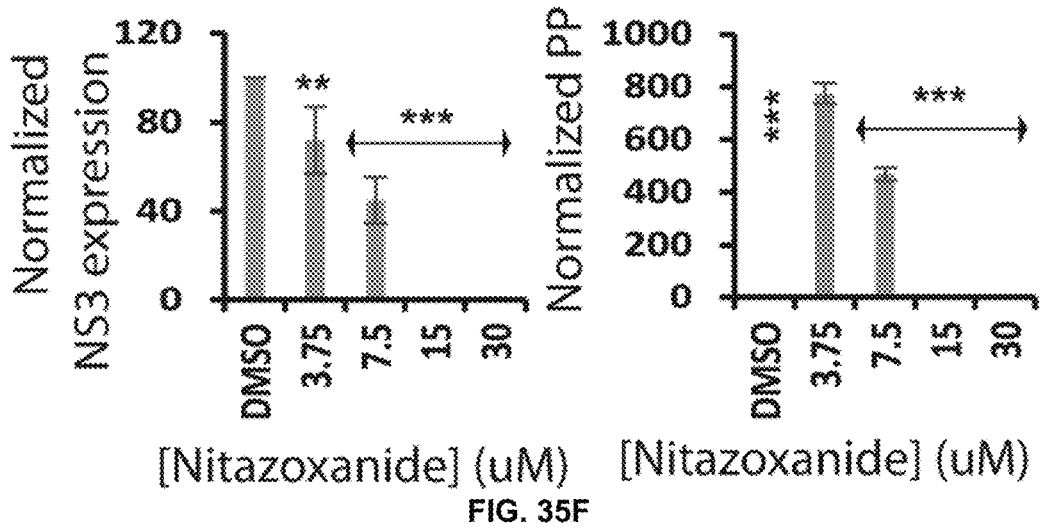
Figure 35G:
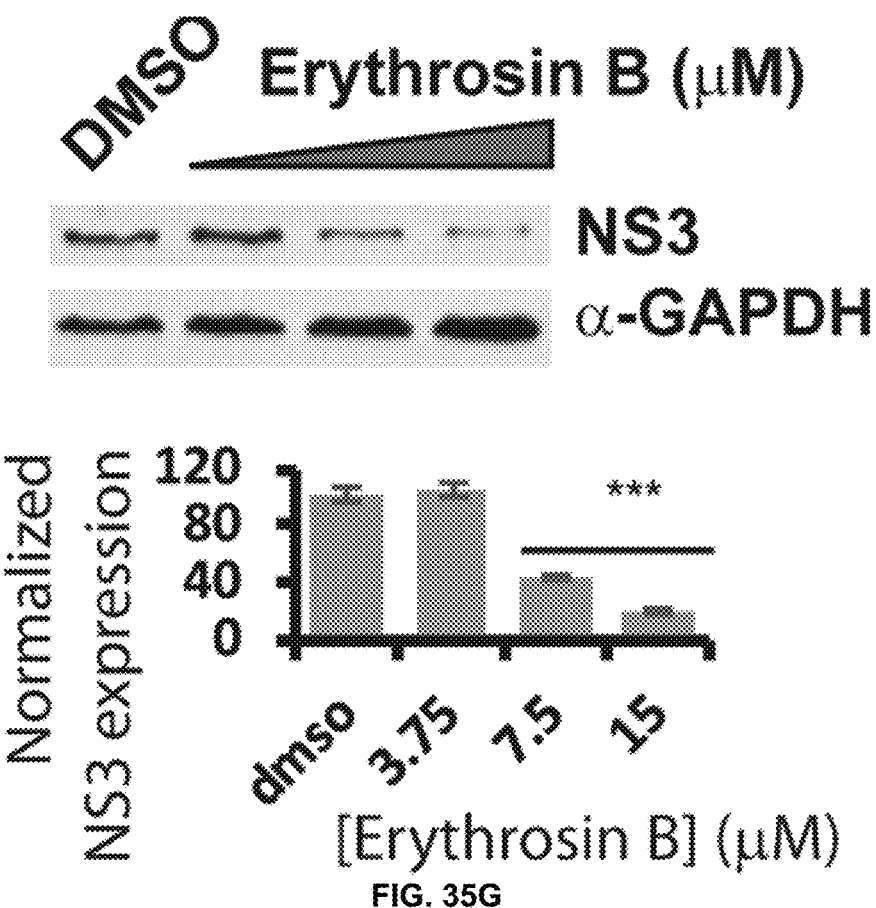
FIG. 35G shows western blot analysis of dose response inhibition of ZIKV NS3 expression by erythrosin B (upper panel). Lower panel, NS3 expression normalized to the GAPDH loading control. ***, p<0.01.

FIG. 35G shows WB analysis of dose response inhibition of ZIKV NS3 expression by erythrosin B (upper panel). Lower panel, NS3 expression normalized to the GAPDH loading control. The expression of ZIKV NS3 (~70 KDa) was significantly inhibited by erythrosin B in a dose-dependent manner.

To further characterize the high MW protein detected, we excised the protein bands, digested with trypsin, and performed mass spectrometry analysis. Peptides corresponding to the ZIKV capsid, envelope, NS3, and NS5 proteins were identified.

Protein band of interest on SDS-PAGE gel was manually excised. The pieces were dehydrated with acetonitrile for 10 min, vacuum dried, rehydrated with 5 mM triphosphine hydrochloride in 50 mM ammonium bicarbonate (pH 8.5) at 37° C. for 1 h, and then alkylated with 100 mM iodoacetamide in 50 mM ammonium bicarbonate (pH 8.5) at room temperature for 1 h. The pieces were washed twice with 50% acetonitrile, dehydrated with acetonitrile for 10 min, dried, and digested with a total of 25 ng of sequencing grade modified trypsin (Sigma-Aldrich) in 50 mM ammonium bicarbonate (pH 8.5) at 37° C. overnight. Following digestion, tryptic peptides were extracted three times with 50% acetonitrile containing 5% formic acid for 15 min each time while being vortexed. The extracted solutions were pooled and evaporated under vacuum prior to MS analysis.

Peptides were re-suspended in 60 µL of 0.1% vol/vol formic acid and separated on a CapLC system (Waters Co. Milford, Mass., USA) coupled to a QSTAR XL (ABSCIEX, Framingham Mass.). Peptides were desalted onto an Everest C18 (5 µm, 500 µm ID×15 mm, Grace, Deerfield, Ill.) with solvent A (97:3 $H_2O$:ACN with 0.1% vol/vol formic acid and 0.01% vol/vol TFA) at 40 µL/min. After a 6-min wash, peptides were separated on a Jupiter C18 (3 µm, 100 µm ID×150 mm, Phenomenex, Torrance, Calif.) using a 40-min linear gradient of 10% to 40% solvent B (85% ACN/10% isopropanol+0.1% vol/vol formic acid+0.0075% vol/vol TFA) at 250 nL/min. MS data acquisition was performed using Analyst QS 1.1 software (ABSciex) in positive ion mode for information dependent acquisition (IDA) analysis. The nanospray voltage was 2.1 kV used for all experiments in a positive ion mode. Nitrogen was used as the curtain (value of 20) with heated interface at 130° C. The declustering potential was set at 80 eV and Gas1 was 5 (arbitrary unit). In IDA analysis, after each survey scan from m/z 350 to m/z 1200, the three highest intensity ions above the predefined threshold 28 cps with multiple charge states (+2 and +3) were selected for tandem MS (MS/MS), with rolling collision energy applied for detected ions based on different charge states and m/z values. Each MS/MS acquisition was completed and switched back to survey scan when the precursor intensity fell below a predefined threshold or after a maximum of 65 s acquisition. After data acquisition, the individual MS/MS spectra acquired for each precursor within a single LC run were combined, smoothed, deisotoped using an Analyst "script" mascot.dll to create a peak list, and the peak list was saved to a file. Then the peak list file was used to query viral protein and contaminant data subsets using the MASCOT 2.5 from Matrix Science (London, UK) with the following parameters: peptide mass tolerance, 0.3 Da; MS/MS ion mass tolerance, 0.3 Da; allow up to two missed cleavage. Several variable modifications were applied, including methionine oxidation and cysteine carbamidomethylation. Only significant scores for the peptides defined by Mascot probability analysis (http://www-.matrixscience.com/help/scoring_help.html#PBM) greater than "identity" with 95% confidence were considered for the peptide identification.

Figure 36A:
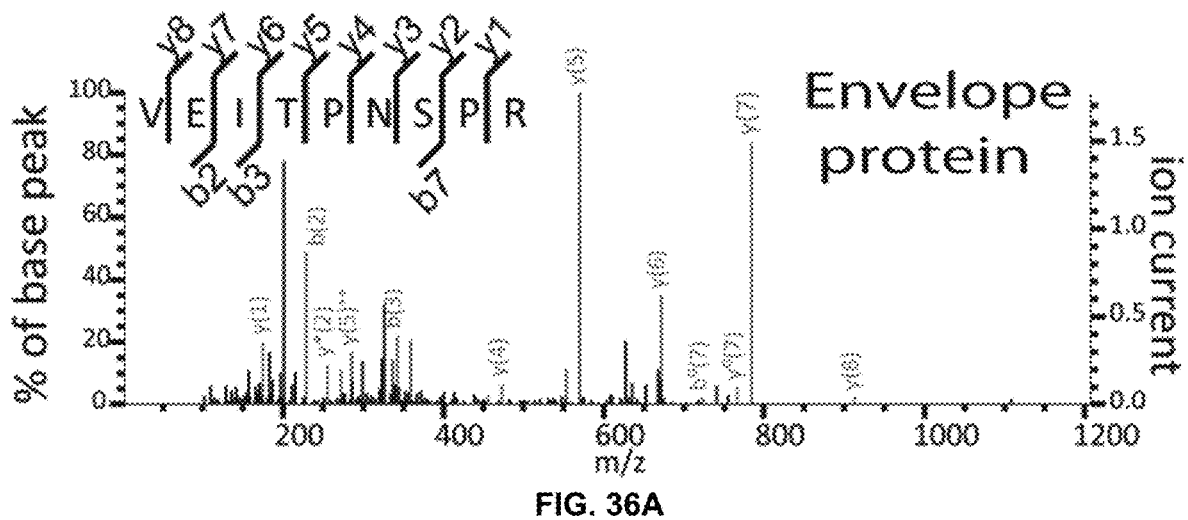
FIG. 36A, FIG. 36B, and FIG. 36C show tandem mass spectrometry (MS/MS) spectra obtained from the fragmentation of precursor ion at m/z corresponding to representative ZIKV peptides (Envelope protein, NS3, and NS5, respectively). Fragment ions corresponding to y- and b-ions were observed (red lines).
Figure 36B:
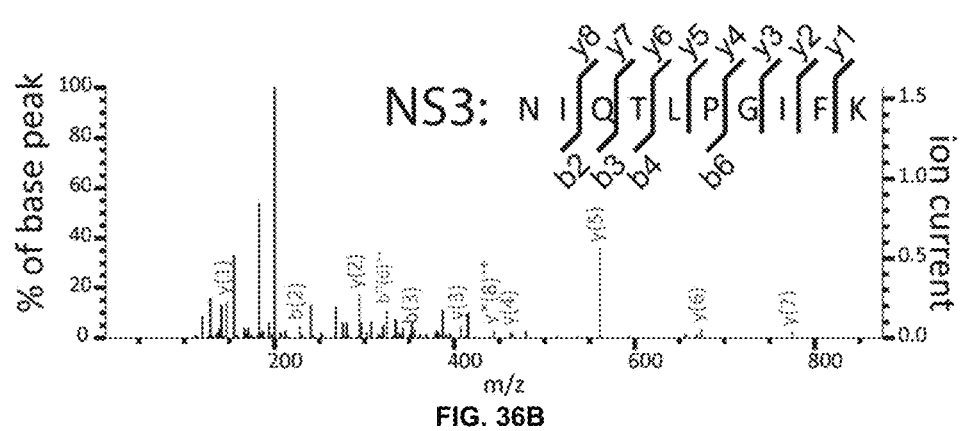
Figure 36C:
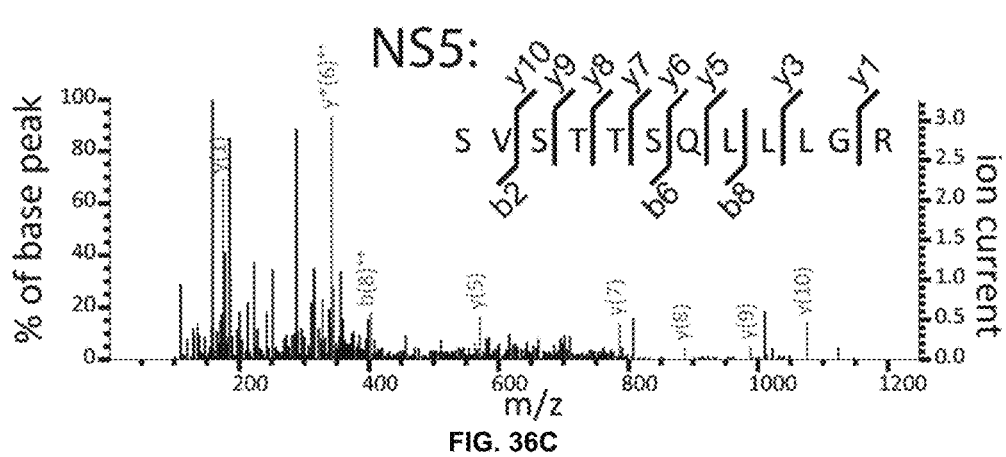

The mass spectrometry data, shown in FIGS. 36A (envelope protein), 36B (NS3) and 36C (NS5) unambiguously confirmed that the high MW protein was the unprocessed ZIKV polyprotein precursor (PP) (~3,391 amino acids). Unprocessed viral PP may accumulate due to inhibition of viral protease by lower concentrations of drugs. For samples treated with drugs at high concentrations, decreased accumulation or absence of PP may be because of the overall reduced expression of viral protein. Overall, PP accumulation in the presence of drugs indicated that PP processing by the viral protease was inhibited.

To explore the drugs' potential modes of actions, we docked temoporfin, niclosamide, nitazoxanide, and erythrosine B to the crystal structure of the ligand-bound NS3 proteases of DENV3 (PDB ID: 3U1I) and ZIKV (PDB ID: 5LC0) after removing the NS2B peptides. The NS2B-bound crystal structures of the DENV3 (PDB ID: 3U1I) were downloaded from RCSB PDB Bank. To prepare the NS3 protease structure for the mapping task, ligands and cofactors were removed, hydrogens were added, and crystal waters were removed. The SiteMap Calculation was run from the Schrödinger Maestro[45] SiteMap panel. The task of identifying top-ranked potential receptor binding site was specified and a fine grid spacing of 0.7 Å was selected. The OPLS_2005 force field was used for calculation. The result from the mapping was then incorporated into Maestro for visualization and evaluation.

The 3D structures for niclosamide, nitazoxanide, temoporfin, and erythrosin B were downloaded in SDF format from the ZINC 15 library. The NS2B-bound crystal structures of the Dengue NS3 protease (PDB ID: 3U1I) and of the Zika NS3 protease (PDB ID: 5LC0) were used as docking targets to predict the possible bound conformations of these compounds. The program Autodock Vina was used to dock molecules into two putative binding sites corresponding to two NS2B residues that bind to NS3: L51/M51 and V53/I53. The Cartesian coordinates of the CB atom of each of these residues were used as the center of the box used for docking in the respective structure. Ligand boxes extended 25 Å in each direction, and an exhaustiveness parameter of 16 was used for the docking.

In order to generate a more accurate ligand poses and accommodate movements of highly flexible residues on NS3 protease, an Induced Fit Docking (IFD) protocol of Schrödinger Small-Molecule Drug Discovery Suite was employed in a docking study. Crystal structures of DENV3 (PDB Code: 3U1I) and ZIKV (PDB Code: 5LC0) were used as docking templates. Only NS3 protease was kept from each structure and prepared with Protein Prepared Wizard. During this step, hydrogens were added, crystal waters were removed, partial charges was assigned using OPLS-2005 force field, and protonation states were assigned. 3D conformations of ligands were created using Schrödinger Maestro and prepared with LigPrep. A single, low-energy, 3D structure of each ligand was produced. An Induced Fit Docking protocol was run from Schrödinger Maestro using Induced Fit Docking panel. On NS3 chains of DENV3 and ZIKV, a center of box for docking was chosen on a centroid of a set of selected residues within the 2B53 pocket. Box size was set to 26 Å on each side. Selected side chains (R24, K26, and T59 of DENV3; M1026, S1060, and Y1023 of ZIKV) were temporarily removed (equivalent of being temporarily mutated to alanine) to create more space during initial IFD process and were restored after docking step. IFD procedure used reduced van der Waals radii scaling (0.7 for nonpolar receptor atoms and 0.5 for nonpolar ligand atoms) for a flexible docking. For each pose generated from initial Glide docking, a Prime structure prediction was then used to accommodate ligand by reorienting nearby side chains. Residues and ligand were then minimized. Receptor structures were optimized. Finally, each ligand was re-docked into structures within 30 kcal/mol, and within the top 20 structures using Glide XP mode. As a result, multiple docking poses were generated and ranked according to the IFD scores. Poses with lower values of IFD scores are more favorable for binding. Receptor-ligand complexes structures were imported into Schrödinger Maestro for visualization and analysis of binding site interactions.

Figure 37A:
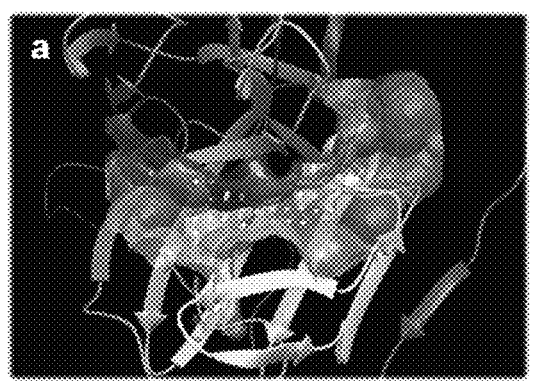
FIG. 37A shows a top-ranked site (gray surface presentation) for NS3pro (ribbon presentation) of DENV3 (PDB: 3U1I) from SiteMap calculation, located in the area containing 2B51 and 2B53 pockets. Hydrogen bond acceptor map is shown in red, hydrogen bond donor map in blue, and hydrophobic map in yellow. 88 site points are shown in white dots inside the pockets.
Figure 37B:
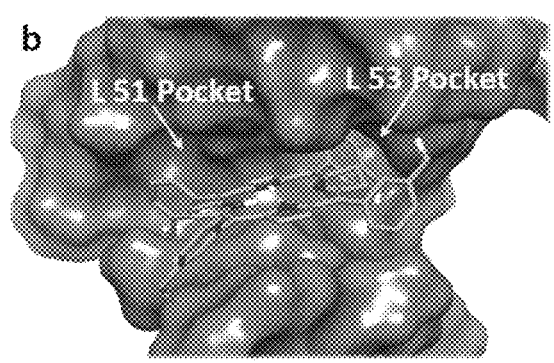
FIG. 37B shows a docking pose of temoporfin (green) docked into NS3pro of DENV3 (PDB: 3U1I) in surface presentation. 2B51 and 2B53 pockets are marked with yellow arrows.

First a SiteMap calculation on NS3pro of DENV3 was performed to identify potential pockets on NS3 for binding of these drugs. NS3 pockets holding NS2B residues 51 and 53 were ranked as a top site. Best SiteScore was (0.998) and best Druggability Score was (1.050). FIG. 37A shows a top-ranked site (gray surface presentation) for NS3pro (ribbon presentation) of DENV3 (PDB: 3U1I) from SiteMap calculation. It is located in an area containing 2B51 and 2B53 pockets. Hydrogen bond acceptor map is shown in red, hydrogen bond donor map in blue, and hydrophobic map in yellow. 88 site points are shown in white dots inside pockets. FIG. 37B shows a docking pose of Temoporfin (green) docked into NS3pro of DENV3 (PDB: 3U1I) in surface presentation. 2B51 and 2B53 pockets are marked with yellow arrows. Docking results also supported identification of 51/53 pockets as a top ranked-binding site. Therefore, following results are discussed based on docking poses to these sites.

Autodock Vina was then used to employ an identical docking procedure to dock temoporfin, niclosamide, nitazoxanide, and erythrosine B to pockets identified as above. Autodock Vina binding scores for nitazoxanide, niclosamide, and temoporfin were −7.2 kcal/mol, −7.5 kcal/mol, and −9.3 kcal/mol, respectively.

Figure 38A:
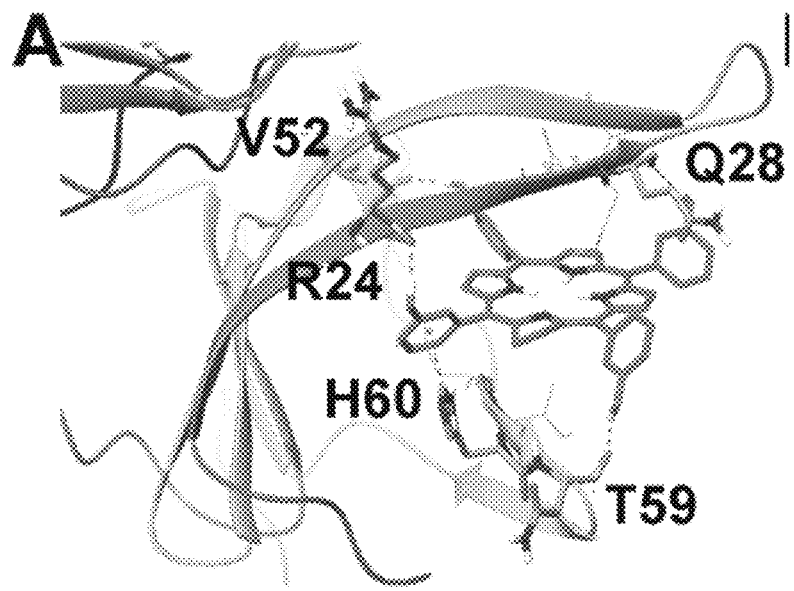
FIG. 38A and FIG. 38B show ribbon presentation of temoporfin (green) docked into NS3pro of DENV3 (PDB: 3U1I) (FIG. 38A) and ZIKV (PDB: 5LC0) (FIG. 38B). NS3pro β-strand hairpin loops with residues 25-36 (DENV3) or 1025-1036 (ZIKV) are shown in orange and the loops with residues 56-67 (DENV3) or 1056-1067 (ZIKV) are shown in yellow. Key interaction residues are highlighted in stick presentation. Hydrogen bonds are shown in purple dotted lines and π-π stacking is shown in blue dotted line.
Figure 38B:
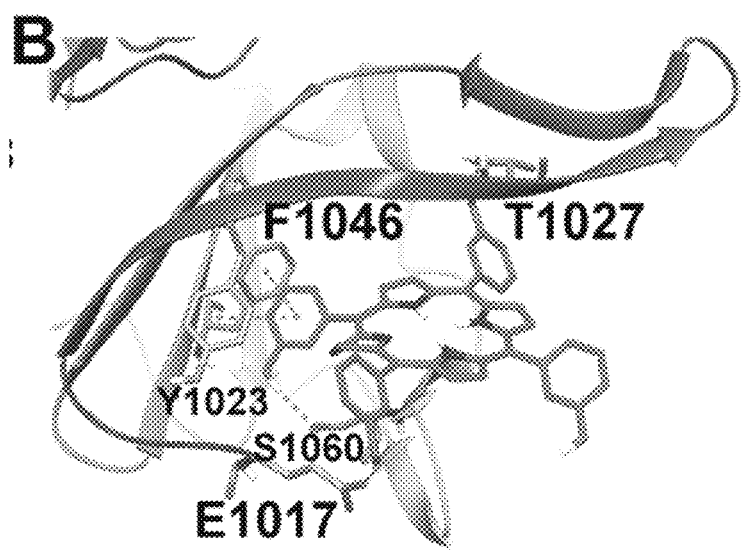

According to results from an Induced Fit Docking protocol, with 3U1I and 5LC0 as models, temoporfin, niclosamide, nitazoxanide, and erythrosine B were well docked into an NS3 pockets holding NS2B residues at positions 51 and 53, termed as 2B51 and 2B53 pockets, respectively. FIGS. 38A and 38B show ribbon presentation of temoporfin (green) docked into NS3pro of DENV3 (PDB: 3U1I) (38A) and ZIKV (PDB: 5LC0) (38B). Top-ranked site (gray surface presentation) for NS3pro (ribbon presentation) of DENV3 (PDB: 3U1I) from SiteMap calculation located in the area containing 2B51 and 2B53 pockets is shown in FIG. 38A. Hydrogen bond acceptor map is shown in red, hydrogen bond donor map in blue, and hydrophobic map in yellow. 88 site points are shown in white dots inside the pockets. FIG. 38B shows a docking pose of Temoporfin (green) docked into NS3pro of DENV3 (PDB: 3U1I) in surface presentation. The 2B51 and 2B53 pockets are marked with yellow arrows. Temoporfin may be tightly sandwiched between two NS3 hairpin loops 25-36 and 56-67. NS3 residues 24-28 may be lined up on one side of temoporfin, whereas the NS3 residues 58-61 form the other side of the channel. The bottom of the channel is formed by the NS3 residues 23, 25, 53 and 58. Two of the phenol groups of temoporfin are anchored into the 2B51 and 2B53 pockets as shown in the surface presentation of docking pose. The Induced Fit Docking also generated several possible binding poses demonstrating interactions, including hydrogen bonds and π stacking between ligand and NS3 residues R24, N27, Q28, K33, R54, T59, and H60. These highly flexible NS3 residues are exposed to solvent and likely adopt many different conformations in solution respectively.

Figure 38C:
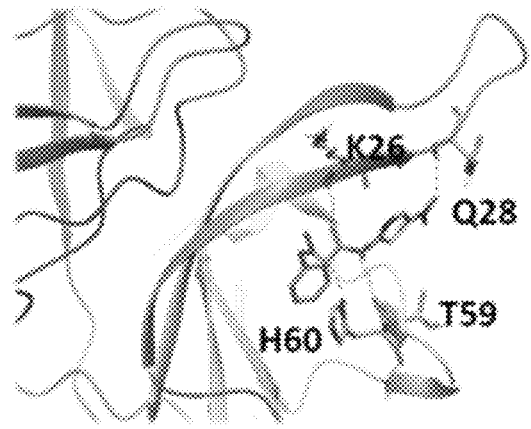
FIG. 38C shows ribbon presentation of nitazoxanide (green) docked into NS3pro of DENV3 (PDB: 3U1I). NS3pro hairpin loop with residues 25-36 is shown in orange and the loop with residues 56-67 is shown in yellow. Key interaction residues are highlighted in stick presentation. Hydrogen bonds and halogen bonds are shown in purple dotted lines, and n-n stacking is shown in blue dotted line.
Figure 38D:
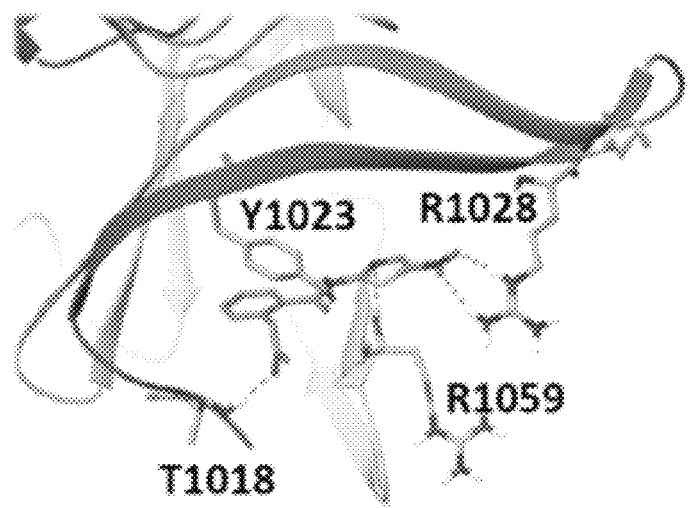
FIG. 38D shows ribbon presentation of nitazoxanide (green) docked into NS3pro of ZIKV (PDB: 5LC0). The corresponding NS3pro hairpin loop on ZIKV are shown in orange and yellow. Key interaction residues are highlighted in stick presentation. Hydrogen bonds and halogen bonds are also shown in purple dotted lines, and n-n stacking is shown in blue dotted lines.
Figure 38E:
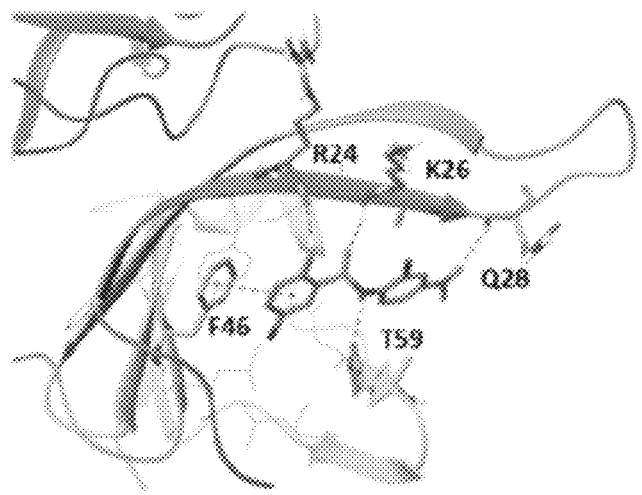
FIG. 38E shows ribbon presentation of niclosamide (green) docked into NS3pro of DENV3 (PDB: 3U1I).
Figure 38F:
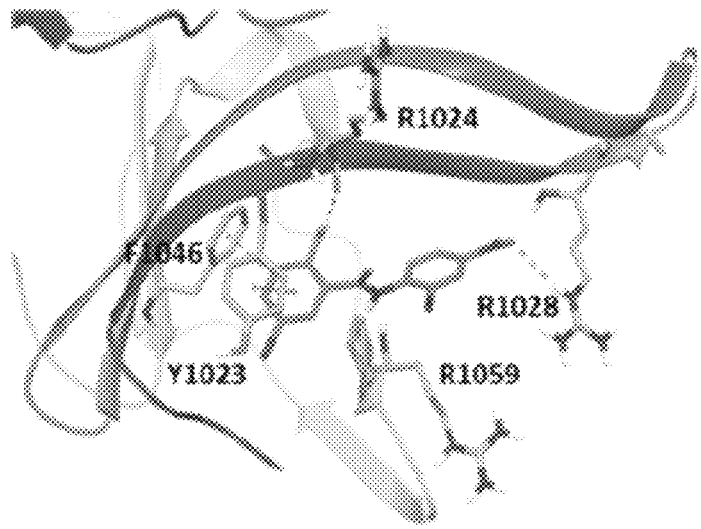
FIG. 38F shows ribbon presentation of niclosamide (green) docked into NS3pro of ZIKV (PDB:5LC0).

Docking result also show niclosamide and nitazoxanide may bind well into the 2B53 pocket in a similar fashion as temoporfin. FIGS. 38C-38F show induced fit docking of nitazoxanide (38C-D) and niclosamide (38E-F) to an NS2B 2B51 and 2B53 pockets on NS3pro. FIG. 38C shows ribbon presentation of nitazoxanide (green) docked into NS3pro of DENV3 (PDB: 3U1I). NS3pro β-strand hairpin loops with residues 25-36 (DENV3) or 1025-1036 (ZIKV) are shown in orange and the loops with residues 56-67 (DENV3) or 1056-1067 (ZIKV) are shown in yellow. Key interaction residues are highlighted in stick presentation. Hydrogen bonds and halogen bonds are shown in purple dotted lines, and π-π stacking is shown in blue dotted line. FIG. 38D shows ribbon presentation of nitazoxanide (green) docked into NS3pro of ZIKV (PDB: 5LC0). A corresponding NS3pro hairpin loop on ZIKV are shown in orange and yellow. Key interaction residues are highlighted in stick presentation. Hydrogen bonds and halogen bonds are also shown in purple dotted lines, and π-π stacking is shown in blue dotted lines. FIG. 38E shows ribbon presentation of niclosamide (green) docked into NS3pro of DENV3 (PDB: 3U1I. FIG. 38F shows ribbon presentation of niclosamide (green) docked into NS3pro of ZIKV (PDB: 5LC0).

Figure 38G:
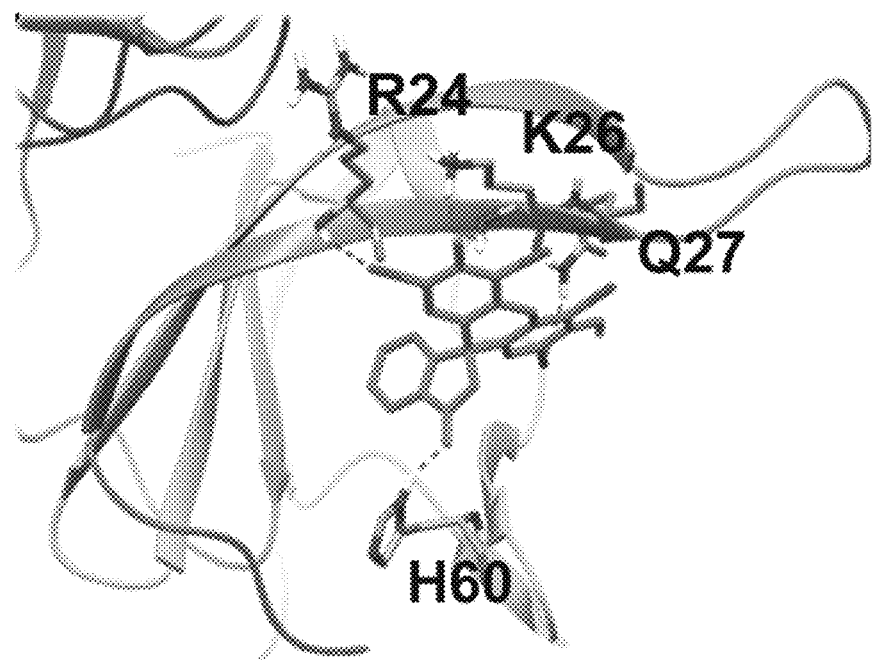
FIG. 38G shows ribbon presentation of erythrosin B (green) docked into NS3pro of DENV3 (PDB: 3U1I). NS3pro β-strand hairpin loop with residues 25-36 is shown in orange and the loop with residues 56-67 is shown in yellow. Key interaction residues R24, K26, Q27 and H60 are highlighted in stick presentation. Hydrogen bonds are shown in purple dotted lines and π-π stacking is shown in blue dotted line.
Figure 38H:
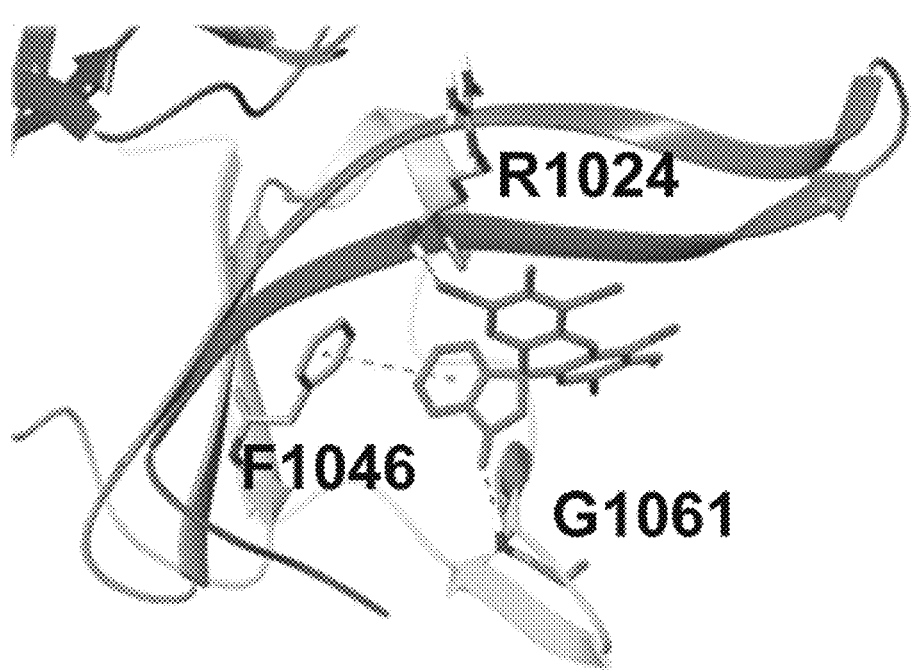
FIG. 38H shows ribbon presentation of erythrosin B (green) docked into NS3pro of ZIKV (PDB: 5LC0). The corresponding NS3pro 3-strand hairpin loop on ZIKV are shown in orange and yellow. Key interaction residues R1024, F1046, and G1061 are highlighted in stick presentation. Hydrogen bonds are also shown in purple dotted lines and π-π stacking is shown in blue dotted lines.

As shown in FIGS. 38G-H, erythrosin B may be well docked into the NS3 pockets holding the NS2B residues at positions 51 and 53, termed as 2B51 and 2B53 pockets, respectively. FIG. 38G shows ribbon presentation of erythrosin B (green) docked into NS3pro of DENV3 (PDB: 3U1I). NS3pro β-strand hairpin loop with residues 25-36 is shown in orange and the loop with residues 56-67 is shown in yellow. Key interaction residues R24, K26, Q27 and H60 are highlighted in stick presentation. Hydrogen bonds are shown in purple dotted lines and π-π stacking is shown in blue dotted line. FIG. 38G shows ribbon presentation of erythrosin B (green) docked into NS3pro of ZIKV (PDB: 5LC0). The corresponding NS3pro β-strand hairpin loop on ZIKV are shown in orange and yellow. Key interaction residues R1024, F1046, and G1061 are highlighted in stick presentation. Hydrogen bonds are also shown in purple dotted lines and π-π stacking is shown in blue dotted lines. The docking pose shows that EB can access the 2B51 and 2B53 pockets on NS3 protease and formed interactions with key residues of H60, K26, R24, Q27 and Q28 through hydrogen bonds, halogen bonds and π-π interactions.

These docked poses of the compounds support the supposition that this hydrophobic pocket in NS3, into which a part of NS2B binds, can reasonably lodge small molecules in the size range of these compounds.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be understood that the terms "comprise", "have", "include", and "contain" (and any related variants thereof) are open-ended linking verbs. As a result, a method, step, or device that "comprises", "has", "includes" or "contains" one or more steps or elements possesses those one or more steps or elements, but is not limited to possessing only those one or more steps or elements. The corresponding structures, materials, acts, and equivalents of all means or step plus function elements in the claims below, if any, are intended to include any structure, material, or act for performing the function in combination with other claimed elements as specifically claimed. The disclosure herein is illustrative and not intended to be exhaustive or limited to the invention in the form disclosed. Many modifications and variations will be apparent to those of ordinary skill in the art without departing from the scope and spirit of the invention. Embodiments are described to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method of inhibiting viral replication comprising:
contacting one or more cells that have been infected with a virus with an effective amount of a compound, wherein the compound is selected from

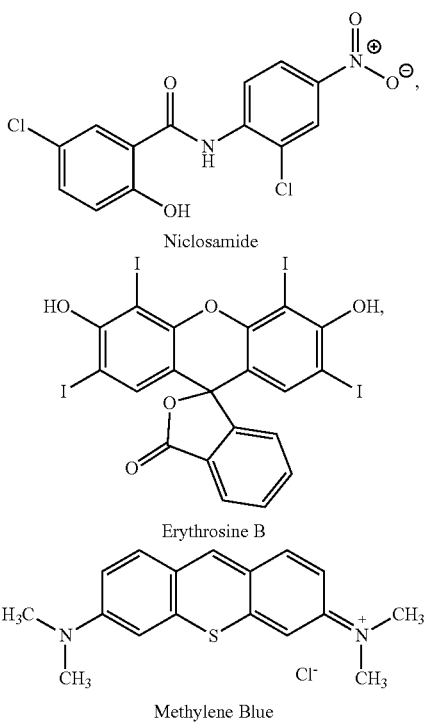

Niclosamide

Erythrosine B

Methylene Blue a pharmaceutically acceptable salt thereof, and any combination of two or more of the foregoing, and the virus comprises a flavivirus, and contacting one or more cells that have been infected with the virus comprises administering the compound to a subject, wherein
when the flavivirus is yellow fever virus, Japanese encephalitis virus or a Dengue virus, the compound does not comprise Niclosamide or a pharmaceutically acceptable salt thereof, and
when the compound comprises Methylene Blue or a pharmaceutically acceptable salt thereof, the method does not comprise photoactivation of the compound.

2. The method of claim 1, wherein the subject is a mammal.
3. The method of claim 1, wherein the subject is a human.
4. The method of claim 1, wherein the virus is Zika virus.
5. The method of claim 1, wherein the flavivirus is selected from Dengue virus serotype 1, Dengue virus serotype 2, Dengue virus serotype 3, Dengue virus serotype 4, yellow fever virus, West Nile virus, Zika virus, Japanese encephalitis virus, and any combination of two or more of the foregoing.
6. The method of claim 5, wherein the subject is a mammal.
7. The method of claim 5, wherein the subject is a human.
8. The method of claim 5, wherein the compound is Niclosamide.
9. The method of claim 5, wherein the compound is Erythrosine B.
10. The method of claim 5, wherein the compound is Methylene Blue.
11. The method of claim 1, wherein the compound is Niclosamide.
12. The method of claim 1, wherein the compound is Erythrosine B.
13. The method of claim 1, wherein the compound is Methylene Blue.
14. The method of claim 1, wherein the compound is Niclosamide and the virus is Zika virus.
15. The method of claim 1, wherein the compound is Erythrosine B and the virus is Zika virus.
16. The method of claim 1, wherein the compound is Methylene Blue and the virus is Zika virus.
17. A method of inhibiting viral replication comprising:
contacting one or more cells that have been infected with a virus with an effective amount of a compound, wherein the compound is selected from

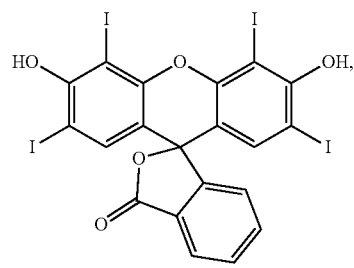

Erythrosine B

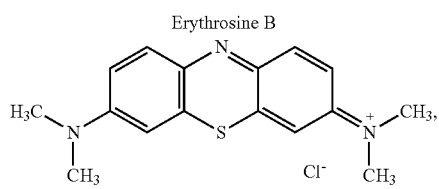

Methylene Blue a pharmaceutically acceptable salt thereof, and any combination of two or more of the foregoing, and
the virus comprises a flavivirus, and
contacting one or more cells that have been infected with a flavivirus comprises administering the compound to a subject, wherein
when the compound comprises Methylene Blue or a pharmaceutically acceptable salt thereof, the method does not comprise photoactivation of the compound.

18. The method of claim 17, wherein the subject is a mammal.
19. The method of claim 17, wherein the subject is a human.
20. A method of inhibiting viral replication comprising:
administering to a human subject an effective amount of a compound, wherein the compound is selected from

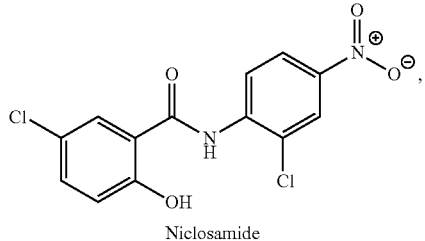

Niclosamide

-continued

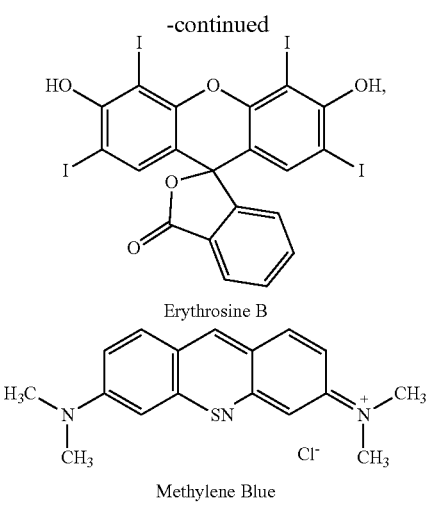

Erythrosine B

Methylene Blue a pharmaceutically acceptable salt thereof, and any combination of two or more of the foregoing, and the virus is selected from the group consisting of Dengue virus serotype 1, Dengue virus serotype 2, Dengue virus serotype 3, Dengue virus serotype 4, yellow fever virus, West Nile virus, Zika virus, Japanese encephalitis virus, and any combination of two or more of the foregoing, wherein when the flavivirus is selected from yellow fever virus, Japanese encephalitis virus, Dengue virus serotype 1, Dengue virus serotype 2, Dengue virus serotype 3, and Dengue virus serotype 4, the compound does not comprise Niclosamide or a pharmaceutically acceptable salt thereof, and when the compound comprises Methylene Blue or a pharmaceutically acceptable salt thereof, the method does not comprise photoactivation of the compound.

* * * * *

SEQUENCE LISTING

```
<160> NUMBER OF SEQ ID NOS: 29

<210> SEQ ID NO 1
<211> LENGTH: 179
<212> TYPE: PRT
<213> ORGANISM: Dengue virus type 2

<400> SEQUENCE: 1

Ala Gly Val Leu Trp Asp Val Pro Ser Pro Pro Met Gly Lys Ala
1               5                   10                  15

Glu Leu Glu Asp Gly Ala Tyr Arg Ile Lys Gln Lys Gly Ile Leu Gly
                20                  25                  30

Tyr Ser Gln Ile Gly Ala Gly Val Tyr Lys Glu Gly Thr Phe His Thr
            35                  40                  45
```

```
Met Trp His Val Thr Arg Gly Ala Val Leu Met His Lys Gly Lys Arg
 50                  55                  60

Ile Glu Pro Ser Trp Ala Asp Val Lys Asp Leu Ile Ser Tyr Gly
 65                  70                  75                  80

Gly Gly Trp Lys Leu Glu Gly Glu Trp Lys Gly Glu Glu Val Gln
                 85                  90                  95

Val Leu Ala Leu Glu Pro Gly Lys Asn Pro Arg Ala Val Gln Thr Lys
                100                 105                 110

Pro Gly Leu Phe Lys Thr Asn Ala Gly Thr Ile Gly Ala Val Ser Leu
                115                 120                 125

Asp Phe Ser Pro Gly Thr Ser Gly Ser Pro Ile Ile Asp Lys Lys Gly
                130                 135                 140

Lys Val Val Gly Leu Tyr Gly Asn Gly Val Val Thr Arg Ser Gly Ala
145                 150                 155                 160

Tyr Val Ser Ala Ile Ala Gln Thr Glu Lys Ser Ile Glu Asp Asn Pro
                165                 170                 175

Glu Ile Glu

<210> SEQ ID NO 2
<211> LENGTH: 180
<212> TYPE: PRT
<213> ORGANISM: Dengue virus type 1

<400> SEQUENCE: 2

Ser Gly Val Leu Trp Asp Thr Pro Ser Pro Glu Val Glu Arg Ala
 1               5                  10                  15

Val Leu Asp Asp Gly Ile Tyr Arg Ile Leu Gln Arg Gly Leu Leu Gly
                 20                  25                  30

Arg Ser Gln Val Gly Val Gly Val Phe Gln Glu Gly Val Phe His Thr
                 35                  40                  45

Met Trp His Val Thr Arg Gly Ala Val Leu Met Tyr Gln Gly Lys Arg
 50                  55                  60

Leu Glu Pro Ser Trp Ala Ser Val Lys Lys Asp Leu Ile Ser Tyr Gly
 65                  70                  75                  80

Gly Gly Trp Arg Phe Gln Gly Ser Trp Asn Ala Gly Glu Glu Val Gln
                 85                  90                  95

Val Ile Ala Val Glu Pro Gly Lys Asn Pro Lys Asn Val Gln Thr Ala
                100                 105                 110

Pro Gly Thr Phe Lys Thr Pro Glu Gly Glu Val Gly Ala Ile Ala Leu
                115                 120                 125

Asp Phe Lys Pro Gly Thr Ser Gly Ser Pro Ile Val Asn Arg Glu Gly
                130                 135                 140

Lys Ile Val Gly Leu Tyr Gly Asn Gly Val Val Thr Thr Ser Gly Thr
145                 150                 155                 160

Tyr Val Ser Ala Ile Ala Gln Ala Lys Ala Ser Gln Glu Gly Pro Leu
                165                 170                 175

Pro Glu Ile Glu
                180

<210> SEQ ID NO 3
<211> LENGTH: 180
<212> TYPE: PRT
<213> ORGANISM: Dengue virus type 3
```

```
<400> SEQUENCE: 3

Ser Gly Val Leu Trp Asp Val Pro Ser Pro Glu Thr Gln Lys Ala
1               5                   10                  15

Glu Leu Glu Glu Gly Val Tyr Arg Ile Lys Gln Gln Gly Ile Phe Gly
            20                  25                  30

Lys Thr Gln Val Gly Val Gly Val Gln Lys Glu Gly Val Phe His Thr
            35                  40                  45

Met Trp His Val Thr Arg Gly Ala Val Leu Thr His Asn Gly Lys Arg
    50                  55                  60

Leu Glu Pro Asn Trp Ala Ser Val Lys Lys Asp Leu Ile Ser Tyr Gly
65                  70                  75                  80

Gly Gly Trp Arg Leu Ser Ala Gln Trp Gln Lys Gly Glu Glu Val Gln
                85                  90                  95

Val Ile Ala Val Glu Pro Gly Lys Asn Pro Lys Asn Phe Gln Thr Thr
            100                 105                 110

Pro Gly Thr Phe Gln Thr Thr Thr Gly Glu Ile Gly Ala Ile Ala Leu
        115                 120                 125

Asp Phe Lys Pro Gly Thr Ser Gly Ser Pro Ile Ile Asn Arg Glu Gly
    130                 135                 140

Lys Val Val Gly Leu Tyr Gly Asn Gly Val Val Thr Lys Asn Gly Gly
145                 150                 155                 160

Tyr Val Ser Gly Ile Ala Gln Thr Asn Ala Glu Pro Asp Gly Pro Thr
                165                 170                 175

Pro Glu Leu Glu
            180

<210> SEQ ID NO 4
<211> LENGTH: 179
<212> TYPE: PRT
<213> ORGANISM: Dengue virus type 4

<400> SEQUENCE: 4

Ser Gly Ala Leu Trp Asp Val Pro Ser Pro Ala Thr Lys Lys Ala
1               5                   10                  15

Ala Leu Ser Glu Gly Val Tyr Arg Ile Met Gln Arg Gly Leu Phe Gly
            20                  25                  30

Lys Thr Gln Val Gly Val Gly Ile His Met Glu Gly Val Phe His Thr
            35                  40                  45

Met Trp His Val Thr Arg Gly Ser Val Ile Cys His Glu Thr Gly Arg
    50                  55                  60

Leu Glu Pro Ser Trp Ala Asp Val Arg Asn Asp Met Ile Ser Tyr Gly
65                  70                  75                  80

Gly Gly Trp Arg Leu Gly Asp Lys Trp Asp Lys Glu Glu Asp Val Gln
                85                  90                  95

Val Leu Ala Ile Glu Pro Gly Lys Asn Pro Lys His Val Gln Thr Lys
            100                 105                 110

Pro Gly Leu Phe Lys Thr Leu Thr Gly Glu Ile Gly Ala Val Thr Leu
        115                 120                 125

Asp Phe Lys Pro Gly Thr Ser Gly Ser Pro Ile Ile Asn Arg Lys Gly
    130                 135                 140

Lys Val Ile Gly Leu Tyr Gly Asn Gly Val Val Thr Lys Ser Gly Asp
145                 150                 155                 160
```

```
Tyr Val Ser Ala Ile Thr Gln Ala Glu Arg Ile Gly Glu Pro Asp Tyr
                165                 170                 175

Glu Val Asp

<210> SEQ ID NO 5
<211> LENGTH: 180
<212> TYPE: PRT
<213> ORGANISM: West Nile virus

<400> SEQUENCE: 5

Gly Gly Val Leu Trp Asp Thr Pro Ser Pro Lys Glu Tyr Lys Lys Gly
1               5                   10                  15

Asp Thr Thr Thr Gly Val Tyr Arg Ile Met Thr Arg Gly Leu Leu Gly
                20                  25                  30

Ser Tyr Gln Ala Gly Ala Gly Val Met Val Glu Gly Val Phe His Thr
            35                  40                  45

Leu Trp His Thr Thr Lys Gly Ala Ala Leu Met Ser Gly Glu Gly Arg
        50                  55                  60

Leu Asp Pro Tyr Trp Gly Ser Val Lys Glu Asp Arg Leu Cys Tyr Gly
65                  70                  75                  80

Gly Pro Trp Lys Leu Gln His Lys Trp Asn Gly Gln Asp Glu Val Gln
                85                  90                  95

Met Ile Val Val Glu Pro Gly Lys Asn Val Lys Asn Val Gln Thr Lys
                100                 105                 110

Pro Gly Val Phe Lys Thr Pro Glu Gly Glu Ile Gly Ala Val Thr Leu
            115                 120                 125

Asp Phe Pro Thr Gly Thr Ser Gly Ser Pro Ile Val Asp Lys Asn Gly
        130                 135                 140

Asp Val Ile Gly Leu Tyr Gly Asn Gly Val Ile Met Pro Asn Gly Ser
145                 150                 155                 160

Tyr Ile Ser Ala Ile Val Gln Gly Glu Arg Met Asp Glu Pro Ile Pro
                165                 170                 175

Ala Gly Phe Glu
            180

<210> SEQ ID NO 6
<211> LENGTH: 180
<212> TYPE: PRT
<213> ORGANISM: Japanese encephalitis virus

<400> SEQUENCE: 6

Gly Gly Val Phe Trp Asp Thr Pro Ser Pro Lys Pro Cys Ser Lys Gly
1               5                   10                  15

Asp Thr Thr Thr Gly Val Tyr Arg Ile Met Ala Arg Gly Ile Leu Gly
                20                  25                  30

Thr Tyr Gln Ala Gly Val Gly Val Met Tyr Glu Asn Val Phe His Thr
            35                  40                  45

Leu Trp His Thr Thr Arg Gly Ala Ala Ile Met Ser Gly Glu Gly Lys
        50                  55                  60

Leu Thr Pro Tyr Trp Gly Ser Val Lys Glu Asp Arg Ile Ala Tyr Gly
65                  70                  75                  80

Gly Pro Trp Arg Phe Asp Arg Lys Trp Asn Gly Thr Asp Asp Val Gln
                85                  90                  95

Val Ile Val Val Glu Pro Gly Lys Ala Ala Val Asn Ile Gln Thr Lys
                100                 105                 110
```

Pro Gly Val Phe Arg Thr Pro Phe Gly Glu Val Gly Ala Val Ser Leu
            115                 120                 125

Asp Tyr Pro Arg Gly Thr Ser Gly Ser Pro Ile Leu Asp Ser Asn Gly
130                 135                 140

Asp Ile Ile Gly Leu Tyr Gly Asn Gly Val Glu Leu Gly Asp Gly Ser
145                 150                 155                 160

Tyr Val Ser Ala Ile Val Gln Gly Asp Arg Gln Glu Pro Val Pro
                165                 170                 175

Glu Ala Tyr Thr
            180

<210> SEQ ID NO 7
<211> LENGTH: 180
<212> TYPE: PRT
<213> ORGANISM: St. Louis encephalitis virus

<400> SEQUENCE: 7

Gly Gly Ala Leu Trp Asp Val Pro Ser Pro Lys Val Tyr Pro Lys Cys
1               5                   10                  15

Glu Thr Lys Pro Gly Ile Tyr Arg Ile Met Thr Arg Gly Ile Leu Gly
            20                  25                  30

Thr Phe Gln Ala Gly Val Gly Val Met His Glu Gly Val Phe His Thr
        35                  40                  45

Met Trp His Ala Thr Glu Gly Ala Val Leu Arg Asn Gly Glu Gly Arg
    50                  55                  60

Leu Asp Pro Tyr Ala Gly Asp Val Arg Asn Asp Leu Ile Ser Tyr Gly
65                  70                  75                  80

Gly Pro Trp Lys Leu Ser Ala Thr Trp Asp Gly Thr Glu Glu Val Gln
                85                  90                  95

Met Ile Ala Val Ala Pro Gly Lys Pro Ala Ile Asn Val Gln Thr Thr
            100                 105                 110

Pro Gly Val Phe Lys Thr Pro Leu Gly Thr Ile Gly Ala Val Thr Leu
        115                 120                 125

Asp Phe Pro Lys Gly Thr Ser Gly Ser Pro Ile Ile Asn Lys Lys Gly
130                 135                 140

Glu Ile Ile Gly Leu Tyr Gly Asn Gly Val Leu Ile Gly Gln Gly Glu
145                 150                 155                 160

Tyr Val Ser Gly Ile Ile Gln Gly Glu Arg Thr Glu Glu Pro Ile Pro
                165                 170                 175

Asp Ala Tyr Asn
            180

<210> SEQ ID NO 8
<211> LENGTH: 180
<212> TYPE: PRT
<213> ORGANISM: Zika virus

<400> SEQUENCE: 8

Ser Gly Ala Leu Trp Asp Val Pro Ala Pro Lys Glu Val Lys Lys Gly
1               5                   10                  15

Glu Thr Thr Asp Gly Val Tyr Arg Val Met Thr Arg Arg Leu Leu Gly
            20                  25                  30

Ser Thr Gln Val Gly Val Gly Val Met Gln Glu Gly Val Phe His Thr
        35                  40                  45

Met Trp His Val Thr Lys Gly Ala Ala Leu Arg Ser Gly Glu Gly Arg
    50                  55                  60

```
Leu Asp Pro Tyr Trp Gly Asp Val Lys Gln Asp Leu Val Ser Tyr Cys
 65                  70                  75                  80

Gly Pro Trp Lys Leu Asp Ala Ala Trp Asp Gly Leu Ser Glu Val Gln
                 85                  90                  95

Leu Leu Ala Val Pro Gly Glu Arg Ala Arg Asn Ile Gln Thr Leu
                100                 105                 110

Pro Gly Ile Phe Lys Thr Lys Asp Gly Asp Ile Gly Ala Val Ala Leu
            115                 120                 125

Asp Tyr Pro Ala Gly Thr Ser Gly Ser Pro Ile Leu Asp Lys Cys Gly
        130                 135                 140

Arg Val Ile Gly Leu Tyr Gly Asn Gly Val Val Ile Lys Asn Gly Ser
145                 150                 155                 160

Tyr Val Ser Ala Ile Thr Gln Gly Lys Arg Glu Glu Glu Thr Pro Val
                165                 170                 175

Glu Cys Phe Glu
            180

<210> SEQ ID NO 9
<211> LENGTH: 183
<212> TYPE: PRT
<213> ORGANISM: Yellow fever virus

<400> SEQUENCE: 9

Ser Gly Asp Val Leu Trp Asp Ile Pro Thr Pro Lys Ile Ile Glu Glu
 1               5                  10                  15

Cys Glu His Leu Glu Asp Gly Ile Tyr Gly Ile Phe Gln Ser Thr Phe
                 20                  25                  30

Leu Gly Ala Ser Gln Arg Gly Val Gly Val Ala Gln Gly Gly Val Phe
                 35                  40                  45

His Thr Met Trp His Val Thr Arg Gly Ala Phe Leu Val Arg Asn Gly
             50                  55                  60

Lys Lys Leu Ile Pro Ser Trp Ala Ser Val Lys Glu Asp Leu Val Ala
 65                  70                  75                  80

Tyr Gly Gly Ser Trp Lys Leu Glu Gly Arg Trp Asp Gly Glu Glu Glu
                 85                  90                  95

Val Gln Leu Ile Ala Ala Val Pro Gly Lys Asn Val Val Asn Val Gln
                100                 105                 110

Thr Lys Pro Ser Leu Phe Lys Val Arg Asn Gly Gly Glu Ile Gly Ala
            115                 120                 125

Val Ala Leu Asp Tyr Pro Ser Gly Thr Ser Gly Ser Pro Ile Val Asn
        130                 135                 140

Arg Asn Gly Glu Val Ile Gly Leu Tyr Gly Asn Gly Ile Leu Val Gly
145                 150                 155                 160

Asp Asn Ser Phe Val Ser Ala Ile Ser Gln Thr Glu Val Lys Glu Glu
                165                 170                 175

Gly Lys Glu Glu Leu Gln Glu
            180

<210> SEQ ID NO 10
<211> LENGTH: 182
<212> TYPE: PRT
<213> ORGANISM: Tick-borne encephalitis virus
```

-continued

```
<400> SEQUENCE: 10

Ser Asp Leu Val Phe Ser Gly Gln Gly Gly Arg Glu Arg Gly Asp Arg
1               5                   10                  15

Pro Phe Glu Val Lys Asp Gly Val Tyr Arg Ile Phe Ser Pro Gly Leu
            20                  25                  30

Phe Trp Gly Gln Asn Gln Val Gly Val Gly Tyr Gly Ser Lys Gly Val
        35                  40                  45

Leu His Thr Met Trp His Val Thr Arg Gly Ala Ala Leu Ser Ile Asp
    50                  55                  60

Asp Ala Val Ala Gly Pro Tyr Trp Ala Asp Val Arg Glu Asp Val Val
65                  70                  75                  80

Cys Tyr Gly Gly Ala Trp Ser Leu Glu Glu Lys Trp Lys Gly Glu Thr
                85                  90                  95

Val Gln Val His Ala Phe Pro Pro Gly Arg Ala His Glu Val His Gln
            100                 105                 110

Cys Gln Pro Gly Glu Leu Ile Leu Asp Thr Gly Arg Lys Leu Gly Ala
        115                 120                 125

Ile Pro Ile Asp Leu Val Lys Gly Thr Ser Gly Ser Pro Ile Leu Asn
    130                 135                 140

Ala Gln Gly Val Val Gly Leu Tyr Gly Asn Gly Leu Lys Thr Asn
145                 150                 155                 160

Glu Thr Tyr Val Ser Ser Ile Ala Gln Gly Glu Ala Glu Lys Ser Arg
                165                 170                 175

Pro Asn Leu Pro Gln Ala
            180

<210> SEQ ID NO 11
<211> LENGTH: 182
<212> TYPE: PRT
<213> ORGANISM: Powassan virus

<400> SEQUENCE: 11

Thr Asp Leu Val Phe Ser Gly Gln Leu Pro Asp Gln Gly Glu Lys Arg
1               5                   10                  15

Ser Phe Asp Ile Lys Glu Gly Val Tyr Arg Ile Tyr Ala Pro Gly Leu
            20                  25                  30

Phe Trp Gly Tyr Arg Gln Ile Gly Val Gly Tyr Gly Thr Lys Gly Val
        35                  40                  45

Leu His Thr Met Trp His Val Thr Arg Gly Ala Ala Leu Ser Val Glu
    50                  55                  60

Gly Ala Thr Ser Gly Pro Tyr Trp Ala Asp Val Arg Glu Asp Val Val
65                  70                  75                  80

Cys Tyr Gly Gly Ala Trp Gly Leu Asp Lys Lys Trp Gly Gly Glu Val
                85                  90                  95

Val Gln Val His Ala Phe Pro Pro Asp Ser Gly His Lys Ile His Gln
            100                 105                 110

Cys Gln Pro Gly Lys Leu Asn Leu Glu Gly Gly Arg Val Leu Gly Ala
        115                 120                 125

Ile Pro Ile Asp Leu Pro Arg Gly Thr Ser Gly Ser Pro Ile Ile Asn
    130                 135                 140

Ala Gln Gly Asp Val Leu Gly Leu Tyr Gly Asn Gly Leu Lys Ser Asn
145                 150                 155                 160
```

Asp Val Tyr Ile Ser Ser Ile Ala Gln Gly Asn Val Glu Lys Ser Arg
            165                 170                 175

Pro Glu Met Pro Leu Ala
            180

<210> SEQ ID NO 12
<211> LENGTH: 45
<212> TYPE: DNA
<213> ORGANISM: Artificial Sequence
<220> FEATURE:
<223> OTHER INFORMATION: Laboratory-synthesized sequence

<400> SEQUENCE: 12
cagactaatg ccggatccca tatggctgga gtattgtggg atgtc            45

<210> SEQ ID NO 13
<211> LENGTH: 60
<212> TYPE: DNA
<213> ORGANISM: Artificial Sequence
<220> FEATURE:
<223> OTHER INFORMATION: Laboratory synthesized sequence

<400> SEQUENCE: 13
gtcgtgaaac agtacgtgat cttaagggtc actttcgaaa aatatcatct tcgatctctg    60

<210> SEQ ID NO 14
<211> LENGTH: 59
<212> TYPE: DNA
<213> ORGANISM: Artificial Sequence
<220> FEATURE:
<223> OTHER INFORMATION: Laboratory synthesized sequence

<400> SEQUENCE: 14
gatataccat gggcagcagc catcatcatc atcatcacga agacgccaaa aacataaag     59

<210> SEQ ID NO 15
<211> LENGTH: 35
<212> TYPE: DNA
<213> ORGANISM: Artificial Sequence
<220> FEATURE:
<223> OTHER INFORMATION: Laboratory synthesized sequence

<400> SEQUENCE: 15
ccatatggct agcgctggag tattgtggga tgtcc            35

<210> SEQ ID NO 16
<211> LENGTH: 43
<212> TYPE: DNA
<213> ORGANISM: Artificial Sequence
<220> FEATURE:
<223> OTHER INFORMATION: Laboratory synthesized sequence

<400> SEQUENCE: 16
gctcgaattc ggatccctat ccctttcgaa aaatatcatc ttc            43

<210> SEQ ID NO 17
<211> LENGTH: 60
<212> TYPE: DNA
<213> ORGANISM: Artificial Sequence
<220> FEATURE:
<223> OTHER INFORMATION: Laboratory synthesized sequence

<400> SEQUENCE: 17
cggcgctagc catatggctg ccgcgcggca ccaggccgct tccatccttg tcaatcaagg    60

```
<210> SEQ ID NO 18
<211> LENGTH: 45
<212> TYPE: DNA
<213> ORGANISM: Artificial Sequence
<220> FEATURE:
<223> OTHER INFORMATION: Laboratory synthesized sequence

<400> SEQUENCE: 18
gtcaaatggg aagatcaggc ataaatatca ggaagcagtc caatc            45

<210> SEQ ID NO 19
<211> LENGTH: 45
<212> TYPE: DNA
<213> ORGANISM: Artificial Sequence
<220> FEATURE:
<223> OTHER INFORMATION: Laboratory synthesized sequence

<400> SEQUENCE: 19
gattggactg cttcctgata tttatgcctg atcttcccat ttgac            45

<210> SEQ ID NO 20
<211> LENGTH: 42
<212> TYPE: DNA
<213> ORGANISM: Artificial Sequence
<220> FEATURE:
<223> OTHER INFORMATION: Laboratory synthesized sequence

<400> SEQUENCE: 20
ggtggtagcg gcggcggtgg ggaagacgcc aaaaacataa ag               42

<210> SEQ ID NO 21
<211> LENGTH: 44
<212> TYPE: DNA
<213> ORGANISM: Artificial Sequence
<220> FEATURE:
<223> OTHER INFORMATION: Laboratory synthesized sequence

<400> SEQUENCE: 21
gtcgacggag ctcgaattct catccatcct tgtcaatcaa ggcg             44

<210> SEQ ID NO 22
<211> LENGTH: 58
<212> TYPE: DNA
<213> ORGANISM: Artificial Sequence
<220> FEATURE:
<223> OTHER INFORMATION: Laboratory synthesized sequence

<400> SEQUENCE: 22
cgccgatgtc aaatgggaag gcggtggtag cggtggtgaa gacgccaaaa acataaag    58

<210> SEQ ID NO 23
<211> LENGTH: 44
<212> TYPE: DNA
<213> ORGANISM: Artificial Sequence
<220> FEATURE:
<223> OTHER INFORMATION: Laboratory synthesized sequence

<400> SEQUENCE: 23
gtcgacggag ctcgaattct catccatcct tgtcaatcaa ggcg             44

<210> SEQ ID NO 24
<211> LENGTH: 52
<212> TYPE: DNA
<213> ORGANISM: Artificial Sequence
<220> FEATURE:
<223> OTHER INFORMATION: Laboratory synthesized sequence
```

<400> SEQUENCE: 24
gttctgttcc agggtccact gggatcctcc ggttatgtaa acaatccgga ag         52

<210> SEQ ID NO 25
<211> LENGTH: 45
<212> TYPE: DNA
<213> ORGANISM: Artificial Sequence
<220> FEATURE:
<223> OTHER INFORMATION: Laboratory synthesized sequence

<400> SEQUENCE: 25
gggacatccc acaatactcc agccacggcg atctttccgc ccttc                 45

<210> SEQ ID NO 26
<211> LENGTH: 45
<212> TYPE: DNA
<213> ORGANISM: Artificial Sequence
<220> FEATURE:
<223> OTHER INFORMATION: Laboratory synthesized sequence

<400> SEQUENCE: 26
gaagggcgga aagatcgccg tggctggagt attgtgggat gtccc                 45

<210> SEQ ID NO 27
<211> LENGTH: 50
<212> TYPE: DNA
<213> ORGANISM: Artificial Sequence
<220> FEATURE:
<223> OTHER INFORMATION: Laboratory synthesized sequence

<400> SEQUENCE: 27
gtcacgatgc ggccgctcga gtcactttcg aaaaatatca tcttcgatct            50

<210> SEQ ID NO 28
<211> LENGTH: 50
<212> TYPE: DNA
<213> ORGANISM: Artificial Sequence
<220> FEATURE:
<223> OTHER INFORMATION: Laboratory synthesized sequence

<400> SEQUENCE: 28
caatccagag atcgaagatg atatttttc cggttatgta acaatccgg              50

<210> SEQ ID NO 29
<211> LENGTH: 23
<212> TYPE: DNA
<213> ORGANISM: Artificial Sequence
<220> FEATURE:
<223> OTHER INFORMATION: Laboratory synthesized sequence

<400> SEQUENCE: 29
ccgggagctg catgtgtcag agg                                         23